United States Patent
Schafer et al.

(10) Patent No.: US 9,857,359 B2
(45) Date of Patent: Jan. 2, 2018

(54) METHODS FOR DETERMINING DRUG EFFICACY USING CEREBLON-ASSOCIATED PROTEINS

(71) Applicant: CELGENE CORPORATION, Summit, NJ (US)

(72) Inventors: Peter H. Schafer, Belle Mead, NJ (US); Rajesh Chopra, Summit, NJ (US); Antonia Lopez-Girona, San Diego, CA (US); Laura Corral, La Jolla, CA (US); Maria Yinglin Wang, San Diego, CA (US); Pilgrim Jackson, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 13/931,642

(22) Filed: Jun. 28, 2013

(65) Prior Publication Data

US 2014/0162282 A1    Jun. 12, 2014

Related U.S. Application Data

(60) Provisional application No. 61/666,703, filed on Jun. 29, 2012, provisional application No. 61/696,752, filed on Sep. 4, 2012.

(51) Int. Cl.
   *G01N 33/53* (2006.01)
   *G01N 33/50* (2006.01)
   *G01N 33/574* (2006.01)

(52) U.S. Cl.
   CPC ..... *G01N 33/5052* (2013.01); *G01N 33/5023* (2013.01); *G01N 33/5047* (2013.01); *G01N 33/57426* (2013.01); *G01N 2800/101* (2013.01); *G01N 2800/104* (2013.01); *G01N 2800/52* (2013.01)

(58) Field of Classification Search
   CPC .............. G01N 33/5023; G01N 2800/52
   USPC ........................................................ 435/7.1
   See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,683,195 A | 7/1987 | Mullis et al. | |
| 4,810,643 A | 3/1989 | Souza | |
| 4,994,443 A | 2/1991 | Folkman et al. | |
| 4,999,291 A | 3/1991 | Souza | |
| 5,001,116 A | 3/1991 | Folkman et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,391,485 A | 2/1995 | Deeley et al. | |
| 5,393,870 A | 2/1995 | Deeley et al. | |
| 5,441,050 A | 8/1995 | Thurston et al. | |
| 5,573,758 A | 11/1996 | Adorante et al. | |
| 5,580,755 A | 12/1996 | Souza | |
| 5,582,823 A | 12/1996 | Souz | |
| 5,591,767 A | 1/1997 | Mohr et al. | |
| 5,593,990 A | 1/1997 | D'Amato | |
| 5,629,327 A * | 5/1997 | D'Amato | 514/323 |
| 5,635,517 A | 6/1997 | Muller et al. | |
| 5,639,476 A | 6/1997 | Oshlack et al. | |
| 5,674,533 A | 10/1997 | Santus et al. | |
| 5,698,579 A | 12/1997 | Muller et al. | |
| 5,712,291 A | 1/1998 | D'Amato | |
| 5,733,566 A | 3/1998 | Lewis | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,071,948 A | 6/2000 | D'Amato | |
| 6,114,355 A | 9/2000 | D'Amato | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,458,810 B1 | 10/2002 | Muller et al. | |
| 6,476,052 B1 | 11/2002 | Muller et al. | |

(Continued)

FOREIGN PATENT DOCUMENTS

| | | |
|---|---|---|
| EP | 1365033 A1 | 11/2003 |
| EP | 1757306 A1 | 2/2007 |
| EP | 2436387 | 4/2012 |
| JP | H11-504330 | 4/1994 |
| JP | 2000-500645 A | 1/2000 |
| JP | 2005-500854 A | 1/2005 |
| JP | 2011-168588 A | 9/2011 |
| WO | 93/18186 A1 | 9/1993 |
| WO | 97/14714 A1 | 4/1997 |
| WO | 98/03502 A1 | 1/1998 |

(Continued)

OTHER PUBLICATIONS

Kumar et al. Occurrence of Multiple Myeloma in Both Donor and Recipient After Bone Marrow Transplantation; Americn Journal of Hematology, vol. 71 (2002) pp. 227-228.*

Parman et al. Free Radical-Mediated Oxidative DNA Damage in the Mechanism of Thalidomide Teratogenicity; Nature Medicine, vol. 5, No. 5 (1999) pp. 582-585.*

(Continued)

*Primary Examiner* — Scott Long
*Assistant Examiner* — Paul Martin
(74) *Attorney, Agent, or Firm* — Jones Day

(57) ABSTRACT

Use of cereblon-associated proteins as biomarkers for clinical sensitivity to cancer, inflammatory diseases, and patient response to drug treatment.

15 Claims, 65 Drawing Sheets

(56) References Cited

U.S. PATENT DOCUMENTS

| | | | |
|---|---|---|---|
| 6,555,554 | B2 | 4/2003 | Muller et al. |
| 6,927,024 | B2 | 8/2005 | Dodge et al. |
| 7,091,353 | B2 | 8/2006 | Robarge et al. |
| 7,101,663 | B2 | 9/2006 | Godfrey et al. |
| 7,122,799 | B2 | 10/2006 | Hsieh et al. |
| 7,186,507 | B2 | 3/2007 | Bacallao et al. |
| 7,244,759 | B2 | 7/2007 | Muller et al. |
| 7,393,862 | B2 | 7/2008 | Zeldis |
| 7,468,363 | B2 | 12/2008 | Zeldis |
| 7,635,700 | B2 | 12/2009 | Muller et al. |
| 8,143,283 | B1 * | 3/2012 | D'Amato ............... 514/323 |
| 9,217,743 | B2 | 12/2015 | Handa |
| 2002/0045643 | A1 | 4/2002 | Muller et al. |
| 2003/0045552 | A1 | 3/2003 | Robarge et al. |
| 2003/0096841 | A1 | 5/2003 | Robarge et al. |
| 2004/0029832 | A1 | 2/2004 | Zeldis |
| 2004/0220144 | A1 | 11/2004 | Zeldis |
| 2006/0134767 | A1 | 6/2006 | Bouser-Doepener et al. |
| 2006/0188475 | A1 | 8/2006 | Xu et al. |
| 2006/0205787 | A1 | 9/2006 | Muller et al. |
| 2007/0015194 | A1 | 1/2007 | Shohat et al. |
| 2007/0049618 | A1 | 3/2007 | Muller et al. |
| 2007/0065888 | A1 | 3/2007 | Ring et al. |
| 2007/0128636 | A1 * | 6/2007 | Baker et al. ............... 435/6 |
| 2008/0051379 | A1 | 2/2008 | Lerner et al. |
| 2008/0280779 | A1 | 11/2008 | Shaughnessy et al. |
| 2009/0023149 | A1 | 1/2009 | Knudsen |
| 2009/0142297 | A1 | 6/2009 | Muller et al. |
| 2009/0148853 | A1 | 6/2009 | Schafer et al. |
| 2010/0021437 | A1 | 1/2010 | Isacson et al. |
| 2010/0190656 | A1 | 7/2010 | Li et al. |
| 2010/0284915 | A1 | 11/2010 | Dai et al. |
| 2011/0070218 | A1 | 3/2011 | Teichberg et al. |
| 2011/0196150 | A1 | 8/2011 | Man et al. |
| 2011/0200998 | A1 | 8/2011 | Weichselbaum et al. |
| 2011/0223157 | A1 | 9/2011 | Schafer et al. |
| 2012/0035347 | A1 | 2/2012 | Yver |
| 2012/0077741 | A1 | 3/2012 | Delfani et al. |
| 2012/0134969 | A1 | 5/2012 | Handa et al. |
| 2012/0192297 | A1 | 7/2012 | Handa et al. |
| 2012/0230983 | A1 | 9/2012 | Muller et al. |
| 2012/0322073 | A1 | 12/2012 | Lopez-Girona et al. |
| 2013/0177644 | A1 | 7/2013 | Zeldis |
| 2013/0302323 | A1 | 11/2013 | Zeldis |
| 2014/0045843 | A1 | 2/2014 | Schafer et al. |
| 2014/0051591 | A1 * | 2/2014 | O'Donnell et al. ............... 506/9 |
| 2014/0066480 | A1 * | 3/2014 | Stewart et al. ............... 514/323 |
| 2014/0162282 | A1 | 6/2014 | Schafer et al. |

FOREIGN PATENT DOCUMENTS

| | | |
|---|---|---|
| WO | 98/54170 A1 | 3/1998 |
| WO | 02/059106 A1 | 8/2002 |
| WO | 02/070747 A1 | 9/2002 |
| WO | 03/018836 A2 | 3/2003 |
| WO | WO 2007/108968 | 9/2007 |
| WO | WO 2009/075797 | 6/2009 |
| WO | 2010/137547 A1 | 12/2010 |
| WO | WO 2011/049043 A1 | 4/2011 |
| WO | 2012/125438 A1 | 9/2012 |
| WO | 2012/125459 A1 | 9/2012 |
| WO | 2012/125475 A1 | 9/2012 |
| WO | WO 2012/125405 | 9/2012 |
| WO | WO 2012/149299 | 11/2012 |
| WO | WO 2012/153187 | 11/2012 |
| WO | WO 2014/028445 A2 | 2/2014 |

OTHER PUBLICATIONS

Oliver et al. Immune Stimulation in Scleroderma Patients Treated With Thalidomide; Clinical Immunology, vol. 97, No. 2 (2000) pp. 109-120.*

Kiaei et al. Thalidomide and Lenalidomide Extend Survival in a Transgenic Mouse Model of Amyotrophic Lateral Sclerosis; Journal of Neuroscience, vol. 26, No. 9 (2006) pp. 2467-2473.*

Yan et al. Tumor Necrosis Factor Alpha Is a Potent Endogenous Mutagen That Promotes Cellular Transformation; Cancer Research, vol. 66, No. 24 (2006) pp. 11565-11570.*

Kotla et al. Mechanism of Action of Lenalidomide in Hematological Malignancies; Journal of Hematology and Oncology; vol. 2, No. 36 (2009) pp. 1-10.*

Distler et al. Angiogenesis and Vasculogenesis in Systemic Sclerosis; Rheumatology, vol. 45 (2006) pp. iii26-iii27.*

Aklilu et al., "Depletion of normal B cells with rituximab as an adjunct to IL-2 therapy for renal cell carcinoma and melanoma," Annals Oncology, 15:1109-1114 (2004).

Angerer et al., in Genetic Engineering: Principles and Methods, Setlow and Hollaender, Eds., Plenum Press, New York, vol. 7, pp. 43-65 (1985).

Angers et al., "Molecular architecture and assembly of the DDB1-CUL4A ubiquitin ligase machinery," Nature, 443:590-5934 (2006).

Anolik et al., "B cell reconstitution after rituximab treatment of lymphoma recapitulates B cell ontogeny," Clin. Immunol., 122:139-145 (2007).

Ausubel et al. (eds.), Short Protocols in Molecular Biology, Fifth Edition, John Wiley and Sons, New York, Chapter 11 (2002).

Bea et al., "Diffuse large B-cell lymphoma subgroups have distinct genetic profiles that influence tumor biology and improve gene-expression-based survival prediction," Blood, 106(9):3183-3190 (2005).

Bustin et al., "Real-time reverse transcription PCT (qRT-PCR) and its potential use in clinical diagnosis," Clin. Sci., 109:365-379 (2005).

Cairns et al., "Regulation of cancer cell metabolism," Nature Rev., 11:85-95 (2011).

Anonymous, Cancer: Principles & Practice of Oncology, Third Edition, J. B. Lippincott Co., Philadelphia, PA, pp. 1843-1847 (1989).

Cerny et al., "Advances in the treatment of non-Hodgkin's lymphoma," Ann. Oncol., 13 Suppl., 4:211-216 (2002).

Clarke et al., "Changing incidence of non-Hodgkin lymphomas in the United States," Cancer, 94(7):2015-2023 (2002).

Corral et al., "Immunomodulation by thalidomide and thalidomide analogues," Ann. Rheum. Dis., 58:(Suppl I) 1107 1113 (1999).

Gall et al., "Nucleic acid hybridization in cytological preparations," Methods Enzymol., 21:470-480 (1981).

Galustian et al., "Lenalidomide: a novel anticancer drug with multiple modalities," Expert Opin. Pharmacother., 10(1):125-133 (2009).

Genbank Accession No. NP_001166953; GI No. 291045198 (Nov. 24, 2013).

Genbank Accession No. NP_057386; GI No. 39545580 (Sep. 23, 2013).

Gladman et al., Kelley's Textbook of Rheumatology, 2 Vols. 6th Edition, W. B. Saunders Company, Chapter 71, pp. 1071-1073 (2001).

Gladman, "Current concepts in psoriatic arthritis," Curr. Opin. Rheumatol., 14(4):361-366 (2002).

Higgins et al., "A mutation in a novel ATP-dependent Lon protease gene in a kindred with mild mental retardation," Neurology 63:1927-1931 (2004).

Hohberger et al., "Cereblon is expressed in the retina and binds to voltage-gated chloride channels," FEBS Lett., 583:633-637 92009).

Ito et al., "Identification of a primary target of thalidomide teratogenicity," Science, 327(5971):1345-1350 (2010).

Jemal et al., "Cancer Statistics," CA Cancer J. Clin., 57:43-66 (2007).

Jo et al., "Identification and functional characterization of cereblon as a binding protein for large-conductance calcium-activated potassium channel in rat brain," J. Neurochem., 94:1212-1224 (2005).

Jones et al., "Pharmaceutical cocrystals: an emerging approach to physical property enhancement," MRS Bulletin 31:875-879 (2006).

Kabat et al., "Attempts to locate complementarity-determining residues in the variable positions of light and heavy chains," Ann. N.Y. Acad. Sci., 190:382-393 (1971).

(56) References Cited

OTHER PUBLICATIONS

Kallioniemi et al., "Comparative genomic hybridization for molecular cytogenetic analysis of solid tumors," Science 258:818-821 (1992).
Kamarch, "Fluorescence-activated cell sorting of hybrid and transfected cells," Methods Enzymol., 151:150-165 (1987).
Kim et al., "Use of absolute lymphocyte counts to predict response to chemotherapy and survival in diffuse large B-cell lymphoma," J. Clin. Oncology, ASCO Annual Meeting Proceedings Part I., 25(18S), Jun. 20 Supplement, p. 8082 (2007).
Kohler et al., "Continuous cultures of fused cells secreting antibody of predefined specificity," Nature, 256:495-497 (1975).
List et al., "The myelodysplastic syndromes: biology and implications for management," J. Clin. Oncol., 8:1424-1441 (1990).
Lowe et al., Drugs of the Future, 17(9):799-807 (1992).
Mardis et al., "Recurring mutations found by sequencing an acute myeloid leukemia genome," N. Engl. J. Med., 361 (11):1058-1066 (2009).
Marriott et al., "Immunotherapeutic and antitumor potential of thalidomide analogues," Expert Opin. Biol. Ther., 1(4):1-8 (2001).
Muller et al., "Structural modifications of thalidomide produce analogs with enhanced tumor necrosis factor inhibitory activity," J. Med. Chem., 39(17):3238-3240 (1996).
Muller et al., "Thalidomide analogs and PDE4 inhibition," Bioorg. & Med. Chem. Lett., 8:2669-2674 (1998).
Mullis et al., "Specific enzymatic amplification of DNA in vitro: the polymerase chain reaction," Cold Spring Harbor Symp. Quant. Biol., 51:263-273 (1986).
Ngo et al., "Oncogenically active MYD88 mutations in human lymphoma," Nature, 470(7332)115-119 (2011).
Parsons et al., "An integrated genomic analysis of human glioblastoma multiforme," Science, 321:1807-1812 (2008).
Paul (ed), Fundamental Immunology, Second Edition, Raven Press, New York, pp. 332-336 (1989).
Roitt et al., Immunology, Third Edition, Mosby, St. Louis, MO, 17.1-17.12 (1993).
Schultheiss et al., "Pharmaceutical cocrystals and their physicochemcial properties," Cryst. Growth Des., 9(6):2950-2967 (2009).
Shackelford et al., "The LKB1-AMPK Pathway: metabolism and growth control in tumour suppression," Nature Rev., 9:563-575 (2009).
Shan et al., "The role of cocrystals in pharmaceutical science," Drug Discov. Today, 13(9-10):440-446 (2008).
Stahnke et al., "Activation of apoptosis pathways in peripheral blood lymphocytes by in vivo chemotherapy," Blood, 98:3066-3073 (2001).
Taylor et al., "A transgenic mouse that expresses a diversity of human sequence heavy and light chain immunoglobulins," Nucleic Acids Res., 20(23):6287-6295 (1992).
The Merck Manual, 17th Edition, Merck & Company, West Point, PA, pp. 448, 944-952 (1999).
Trask, "An overview of pharmaceutical cocrystals as intellectual property," Mol. Pharm., 4(3):301-309 (2007).
Vishweshwar et al., "Pharmaceutical co-crystals," J. Pharm. Sci., 95(3):499-516 (2006).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Adapt, Paterson Institute for Cancer Research, probests for CRBN, printed Dec. 2, 2013.
Aizawa et al., "mRNA distribution of the thalidomide binding protein cereblon in adult mouse brain," Neurosci. Res., 69:343-347 (2011).
Akhurst, "Taking thalifomide out of rehab," Nature Med., 16(4):370-372 (2010).

Androutsellis-Theotokis et al., (2009) "Targeting neural precursors in the adult brain rescues injured dopamine neurons," Proc. Natl. Acad. Sci. U.S.A., 106 (32): 13570-5.
Basel-Vanagaite et al., "The CC2D1A, a member fo a new gene family with C2 domains, is involved in autosomal recessive non-syndromic mental retardation," J. Med. Genet., 43:203-210 (2006).
Basel-Vanagaite, "Genetics of autosomal recessive non-syndromic mental retardation: recent advances," Clin Genet. 72(3):167-74 (2007).
Basson, "Thalidomide's early effects," Nature Med., 16(4):372 (2010).
Becker et al. (2008) "Adult zebrafish as a model for successful central nervous system regeneration" Restorative Neurol. Neurosci. 26:71-80.
Bonnamain et al., (2012). "Neural stem/progenitor cells as promising candidates for regenerative therapy of the central nervous system," Frontiers in Cellular Neuroscience, 6: 17.
Boyd et al., "High expression levels of the mammalian target of rapamycin inhibitor DEPTOR are predictive of response to thalidomide in myeloma," Leukemia & Lymphoma, 51(11):2126-2129 (2010).
Bredesen et al., (2006) "Cell death in the nervous system," Nature, 443 (7113): 796-802.
Bruggermann et al., "Designer mice: the production of human antibody repertoires in transgenic animals," Year Immunol., 7:33-40 (1993).
Burington et al., "Tumor cell gene expression changes following short-term in vivo exposure to single agent chemotherapeutics are related to survival in multiple myeloma," Clin. Cancer Res., 14(15):4821-4829 (2008).
Carstensen, *Drug Stability: Principles & Practices*, Second Edition, Marcel Dekker, New York, NY, pp. 379-380 (1995).
Chang et al., "What is the functional role of the thalidomide binding protein cereblon," Int. J. Biochem Mol. Biol., 2(3):287-294 (2011).
Charoenfuprasert et al., "Identification of salt-inducible kinase 3 as a novel tumor antigen associated with tumorigenesis of ovarian cancer," Oncogene, 30: 3570-3584 (2011).
Chothia et al., "Structural determinants in the sequence of immunoglobulin variable domain," J. Mol. Biol., 278:457-479 (1998).
Chow et al. Pharmacological Research, "In vivo drug-response in patients with leukemic non-Hodgkin's lymphomas is associated with in vitro chemosensitivity and gene expression profiling," 53: 49-61 (2006).
Christian et al., "p62 (SQSTM1) and cyclic AMP phospodiesterase-4A4 (PDE4A4) locate to a novel, reversible protein aggregate with links to autophagy and proteasome degradation pathways," *Cellular Signaling*, 22:1576-1596 (2010).
Cuoco et al., "Microarray based analysis of an inherited terminal 3p26.3 deletion, containing only the CHL1 gene, from a normal father to his two affected children," Orphanet J Rare Dis., 6:12 (2011).
Dufour-Rainfray et al., "Fetal exposure to teratogens: evidence of genes involved in autism," Neurosci Biobehav Rev., (2011).
Emens et al., "Chemotherapy: friend of foe to cancer vaccines," Curr. Opin. Mol. Ther., 3(1):77-84 (2001).
International Searching Authority, "English Translation of International Preliminary Report on Patentability Issued in PCT/JP2010/058722 dated Dec. 15, 2011".
Ferraiuolo et al., "Microarray analysis of the cellular pathways involved in the adaptation to and progression of motor neuron injury in the SOD1 G93A mouse model of familial ALS," J. Neurosci., 27(34):9201-9219 (2007).
Fleisch et al. (2011) "Investigating regeneration and functional integration of CNS neurons: Lessons from zebrafish genetics and other fish species" Biochim. Biophys. Acta 1812:364-380.
Flemming, "Target indentification: Unravelling thalidomide teratogenicity," Nature Rev. Drug Discov., 9:361 (2010).
Folkman et al., "Angiogenesis inhibition and tumor regression caused by heparin or a heparin fragment in the presence of cortisone," Science, 221:719-725 (1983).
Fukuchi, "Ligand-dependent degradation of Smad3 by a ubiquitin ligase complex of ROC1 and associated proteins," Molecular Biology of the Cell, 12(5): 1059-1524 (2001).

(56) References Cited

OTHER PUBLICATIONS

Garshasbi et al., "A defect in the TUSC3 gene is associated with autosomal recessive mental retardation," *Am. J. Hum. Genetics*, 82:1158-1164 (2008).
Gupta D et al., "Adherence of Multiple Myeloma Cells to Bone Marrow Stromal Cells Up Regulates Vascular Endothelial Growth Factor Secretion: Therapeutic Applications," Leukemia, 2001, 15 (12): 1950-1961.
Heintel et al., "High Expression of the thalidomide-binding protein cereblon (CRBN) is associated with improved clinical response in patients with multiple myeloma treated with lenalidomide and dexamethasone," *53rd ASH Annual Meeting and Exposition*, Abstract 2879 (Dec. 10-13, 2011).
Hernandez et al., "Thalidomide modulates mycobacterium leprae-induced NF-κB pathway and lower cytokine response," *Eur. J. Pharmacol.*, 670:272-279 (2011).
Higgins et al., "Candidate genes for recessive non-syndromic mentalretardation on chromosome 3p (MRT2A)," *Clin. Genet.*, 65:496-500 (2004).
Higgins et al., "Dysregulation of large-conductance $Ca^{2+}$-activated $K^+$ channel expression in nonsyndromal mental retardation due to a cereblon p.R419X mutation," *Neurogenetics*, 9:219-223 (2008).
Higgins et al., "Temporal and spatial mouse brain expression of cereblon, an ionic channel regulator involved in human intelligence," *J. Neurogenetics*, 24:18-26 (2010).
International Search Report for PCT/JP2010/058722 dated Jun. 22, 2010.
International Searching Authority, "International Search Report for PCT/US2013/048510," (dated Jun. 12, 2014).
Ito et al., "Deciphering the mystery of thalidomide teratogenicity," *Congenital Anomalies*, 52:1-7 (2012).
Ito et al., "Teratogenic effects of thalidomide: molecular mechanisms," *Cell. Mol. Life Sci.*, 68(9):1569-1579 (2011).
Jakobovits et al., "Analysis of homozygous mutant chimeric mice: deletion of the immunoglobulin heavy-chain joining region blocks B-cell development and antibody production," *Proc. Natl. Acad. Sci., USA*, 90:2551-2555 (1993).
Jakobovits et al., "Germ-line transmission and expression of human-derived yeast artificial chromosome," *Nature*, 362(6417):255-258 (1993).
Jalkanen et al., "Cell surface proteoglycan of mouse mammary epithelial cells is shed by cleavage of its matrix-binding ectodomain from its membrane-associated domain," *J. Cell Biol.*, 105(6 Pt 2):3087-3096 (1987).
Jalkanen et al., "Heparan sulfate proteoglycans from mouse mammary epithelial cells: localization on the cell surface with a monoclonal antibody," *J. Cell Biol.*, 101(3):976-984 (1985).
Johansson, (2007) "Regeneration and plasticity in the brain and spinal cord," J Cereb Blood Flow Metab, 27:1417-1430.
Kantarci et al, "Identification of the genetic basis of nonsyndromic intellectual disability in large consanguineous families by exome sequencing," *Clin. Genet.*, 78(Suppl. 1):L03 (2010).
Kim et al., "Thalidomide: the tragedy of birth defects and the effective treatment of disease," *Toxicological Sci.*, 122(1):1-6 (2011).
Kishimoto et al. (2012) "Neuronal regeneration in zebrafish model of adult brain injury" Disease Models and Mechanisms 5:200-209.
Knobloch et al., Apoptosis induction by thalidomide: critical for limb teratogenicity but therapeutic, *Current Mol. Pharmacol.*, 4:26-61 (2011).
Lee et al., "Cereblon inhibits proteasome activity by binding to the 20S core proteasome subunit beta type 4," *Biochem. Biophys. Res. Comm.*, 427:618-622 (2012).
Lee et al., "Embryopathic effects of thalidomide and its hydrolysis products in rabbit embryo culture: evidence for a prostaglandin H synthase (PHS)-dependent, reactive oxygen species (ROS)-mediated mechanism," *FASEB J.*, 25:2468-2483 (2011).
Lee et al., "Induction of cereblon by NF-E2-related factor 2 in neuroblastoma cells exposed to hypoxia-reoxygenation," *Biochem. Biophys. Res. Comm.*, 399:711-715 (2010).

Lee et al., "Resistance of CD-1 and ogg1 DNA repair-deficient mice to thalidomide and hydrolysis product embryopathies in embryo culture," *Toxicological Sci.*, 122(1):146-156 (2011).
Lenz et al., "Molecular subtypes of diffuse large B-cell lymphoma arise by distinct genetic pathways," *Proc. Natl. Acad. Sci., USA*, 105(36):13520-13525 (2008).
Lenz et al., "Oncogenic CARD11 mutations in human diffuse large B cell lymphoma," *Science*, 319(5870):1676-1679 (2008).
Lopez-Girona et al., "Direct Binding with Cereblon Mediates the Antiproliferative and Immunomodulatory Action of Lenalidomide and Pomalidomide," Blood, 2011, 118 (21): 335.
Lopez-Girona et al., "Cereblon is direct protein target for immunomodulatory and antiproliferative acttivities of lenalidomide and pomalidomide," *Leukemia*, 26:2326-2335 (2012).
Lopez-Girona et al., "Direct binding with cereblon mediates the antiproliferative and immunomodulatory action of lenalidomide and pomalidomide," *53rd ASH Annual Meeting and Exposition*, 738, 22 pages (2011).
Lu et al., "MaxiK channel partners: Physiological Impact," Journal of Physiology, 570 (1): 65-72 (2006).
Magavi et al., (2000), "Induction of neurogenesis in the neocortex of adult mice," Nature, 405 (6789): 951-5.
Michalak et al., "Testis-derived microRNA profiles of African clawed frogs (*Xenopus*) and their sterile hybrids," Genomics, 91(2): 158-64 (2008).
Mitchell et al., "Physical activity-associated gene expression signature in nonhuman primate motor cortex," *Obesity*, 20:692-698 (2012).
Nakamura et al., "Freud-I/Akil, a Novel PDK1-interacting Protein, Functions as a Scaffold to Activate the PDK1/Akt Pathway in Epidermal Growth Factor Signaling," Mol. Cell. Biol., 28(19):5996-6009 (2008).
Nakatomi et al., (2002) "Regeneration of Hippocampal Pyramidal Neurons after Ischemic Brain Injury by Recruitment of Endogenous Neural Progenitors," Cell, 110 (4): 429-41.
Neben et al., "High plasma basic fibroblast growth factor concentration is associated with response to thalidomide in progressive multiple myeloma," *Clin. Cancer Res.*, 7(9):2675-2681 (2001).
Offidani et al., "Serum C-reactive protein at diagnosis and response to therapy is the most powerful factor predicting outcome of multiple myeloma treated with thalidomide/anthracycline-based therapy," *Clin. Lymphoma & Myeloma*, 8(5):294-299 (2008).
Penichet et al., "Antibody-cytokine fusion proteins for the therapy of cancer," *J. Immunol. Methods*, 284:91-101 (2001).
Plückthun, *The Pharmacology of Monoclonal Antibodies*, vol. 113, Springer Verlag, Berlin, pp. 269-315 (1994).
Pohjola et al., "Terminal 3p deletions in two families—correlation between molecular karyotype and phenotype," American Journal of Medical Genetics, Part (2): 441-6 (2010).
Rajadhyaksha et al., "Behavioral characterization of cereblon forebrain-specific conditional null mice: a model for human non-syndromic intellectual disability," *Behavioural Brain Res.*, 226:428-434 (2012).
Rajkumar, "Multiple myeloma: 2012 update on diagnosis, risk-stratification, and management," Am J Hematol., 87(1):78-88 (2012).
Rajpal et al., "A novel panel of protein biomarkers for predicting response to thalidomide-based therapy in newly diagnosed multiple myeloma patients," *Proteomics*, 11(8):1391-1402 (2011).
Rehmann et al., "The rise, fall and subsequent triumph of thalidomide: Lessons learned in drug development," Ther Adv Hematol., 2(5):291-308 (2011).
Ren et al., "Oncogenic CUL4A determines the response to thalidomide treatment in prostate cancer," *J. Mol. Med.*, 90(10):1121-1132 (2012).
Ripa et al., "A linear model for the pharmacokinetics of azithromycin in healthy volunteers," *Chemother.*, 42:402-409 (1996).
Schutt et al.. "Thalidomide in combination with dexamethasone for pretreated patients with multiple myeloma: serum level of soluble interleukin-2 receptor as a predictive factor for response rate and for survival," *Ann. Hematol.*, 84(9):594-600 (2005).

(56) References Cited

OTHER PUBLICATIONS

Sokka et al., "MRI-guieded gas bubble enhanced ultrasound heating in in vivo rabbit thigh," Phys. Med. Biol., 48:223-241 (2003).
Staudt, "Gene expression profiling of lymphoid malignancies," Ann. Rev. Med., 53:303-318 (2002).
Takada et al., "Protective effect of thalidomide against N-methyl-D-aspartate-induced retinal neurotoxicity," J Neurosci Res., 89(10):1596-604 (2011).
Taylor et al., "Protamine is an inhibitor of angiogenesis," Nature, 297:307-312 (1982).
Therasse et al., "New guidelines to evaluate the response to treatment in solid tumors," J. Natl. Cancer Inst., 92(3):205-216 (2000).
Thome et al., "Antigen receptor signaling to NF-κB via CARMA1, BCL10, and MALT1," Cold Spring Harb. Perspect. Biol., 2:a003004 (2010).
Tierney et al. (eds), Current Medical Diagnosis & Treatment 1998, 37th Edition, Appleton & Lange, Stamford, CT, p. 793 (1998).
Vallet et al., "Update on immunomodulatory drugs (IMiDs) in hematologic and solid malignancies," Expert Opinion on Pharmacotherapy, vol. 13, No. 4, pp. 473-494 (2012).
Willems, "Cognition genes on autosomes: The paradox," Clinical Genetics, 72(1): 9-12 (2007).
Wilson et al., "Novel disease targets and management approaches for diffuse large B-cell lymphoma," Leukemia & Lymphoma, 51(S1):1-10 (2010).
Wu et al., "Screening and indentification of host factors interacting with UL14 of herpes simplex virus 1," Med. Microbiol. Immunol., 200:203-208 (2011).
Wu, "Large-Conductance $Ca^{2+}$-Activated K+ Channels: Physiological Role and Pharmacology," Current medicinal Chemistry, 10(8): 649-661 (2003).
Xin el al., "Primary function analysis of human mental retardation related gene CRBN," Mol. Biol. Rep., 35:251-256 (2008).
Yamazaki et al., "In vivo formation of a glutathione conjugate derived from thalidomide in humanized uPA-NOG mice," Chem Res Toxicol., 24(3):287-9 (2011).
Yang et al., "Exploiting synthetic lethality for the therapy of ABC diffuse large B cell lymphoma," Cancer Cell, 21:723-737 (2012).
Zhang et al., "PI3K/Akt signaling pathway is required for neuroprotection of thalidomide on hypoxic-ischemic cortical neurons in vitro," Brain Research, 1357: 157-65 (2010).
Zhu et al., "Molecular mechanism of action of immune-modulaotry drugs thalidomide, lenalidomide and pomalidomide in multiple myeloma," Leukemia & Lymphoma, 1-5 (2012).
Zhu et al., "Cereblon expression is required for the antimyeloma activityof lenalidomide and pomalidomide," Blood, 118(18):4771-4779 (2011).
Abnova, "CRBN purified MaxPab mouse polyclonal antibody (B01P)," Retrieved online <http://www.abnova.com/products/products_detail.asp?catalog_id=H00051185-B01P>, retrieved on Mar. 25, 2015.
Altschul et al., "Gapped BLAST and PSI-BLAST: A new generation of protein database search programs," Nucleic Acid Res., 25(17):3389-3402 (1997).
Ando et al., "Efficient transfection strategy for the spatiotemporal control of gene expression in zebrafish," Mar. Biotechnol. (NY), 8(3):295-303 (2006).
Babin et al., "Zebrafish models of human motor neuron diseases: advantages and limitations," Prog. Neurobiol., 118:36-58 (2014).
Bartlett, "Regulation of neural stem cell differentiation in the forebrain," Immunol. Cell.Biol., 76(5):414-418 (1998).
Bisht et al., "Brain drug delivery system: a comprehensive review on recent experimental and clinical findings," IJPSR, 2(4):792-806 (2011).
Burchiel et al., Immunopharmacokinetics of Radiolabeled Antibodies and Their Fragments, Masson Publishing, Inc., Chapter 13 (1982).
Chamberlain et al., "Structure of the human Cereblon-DDB1-lenalidomide complex reveals basis for responsiveness to thalidomide analogs," Nature Struct. Mol. Biol., 21(9):803-809 (2014).

Garshasbi et al., "Two independent mutations in the ZC3H14 gene are associated with non-syndromic autosomal recessive mental retardation," Medizinische Genetik, 22(1): 83 (2010).
Hernandez-Ilizalitrurri et al., Higher Response to Lenalidomide in Relapsed/Refractory Diffuse Large B-Cell lymphoma in Nongerminal Center B-Cell Like Than in Germinal Center B-Cell Like Phenotype, Cancer, pp. 5058-5066 (2011).
Hsich et al., "Review: Critical issues in gene therapy for neurologic disease," Human Gene Ther., 13:579-604 (1998).
Ito et al., "Identification of a primary target of thalidomide teratogenicity," Science, 327:1-28 (2010).
Kim et al., Gene Expression Profiles for the Prediction of Progression-free Survival in Diffuse Large B Cell Lymphoma: Results of a DASL Assay, Annals of Hematology, 93 (3): 437-447 (2013).
Kobayashi et al., "Overexpression of the forebrain-specific homeobox gene six3 induces rostral forebrain enlargement in zebrafish," Development, 125:2973-2982 (1998).
Lee et al., "Cereblon binding modulates AMP-activated protein kinase function," Journal of Neurochemistry, 115(WE03-03): 74 (2010).
Lee et al., "Functional modulation of AMP-activated protein kinase by cereblon," Biochimica Biophysica Acta, 1813:448-455 (2011).
Ludwig et al., "IMWG consensus on maintenance therapy in multiple myeloma," Blood, 119(3): 3003-15 (2012).
Marks et al., "By-passing immunization, human antibodies from V-gene libraries displayed on phage," J. Mol. Biol., 222(3):581-597 (1991).
Mochida et al., "Genetic basis of developmental malformations of the cerebral cortex," Arch. Neurol., 61:637-640 (2004).
Patent Cooperation Treaty, International Search Report for application PCT/US2013/054663, dated Aug. 21, 2014.
Razek et al., "Disorders of cortical formation: MR imaging features," AJNR Am. J. Neuroradiol., 30:4-11 (2009).
Santana et al., "Can zebrafish be used as animal model to study Alzheimer's disease," Am. J. Neurodegener. Dis., 1(1):32-48 (2012).
Science Daily, "How many species on Earth? About 8.7 million, new estimate says," Retrieved online <http://www.sciencedaily.com/releases/2011/08/1108323180459.htm>, retrieved on Apr. 7, 2013.
Shestopalov et al., "Oligonucleotide-based tools for studying zebrafish development," Zebrafish, 7(1):31-40 (2010).
Stockdale, Medicine, vol. 3, Rubenstein and Federman, eds., Chapter 12, Section IV and Section X (1998).
Suzuki et al., "Stabe transgene expression from HSV amplicon ectors in the brain: potential involvement of immunoregulatory signals," Mol. Ther., 16(10):1727-1736 (2008).
Thomas et al., "Progess and problems with the use of viral vectors for gene," Nat. Rev. Genet., 4(5):346-358 (2003).
Vanhook, "Thalidomide Target Identified," Sci. Signal., vol. 3, Issue 113, p. ec82 (2010).
Abrahams et al., "Methods used in the structure determination of bovine mitochondrial F1 ATPase," Acta Crystallogr. D. Biol. Crystallogr., 52(Pt 1):30-42 (1996).
Aitipamula et al., "Polymorphs, salts, and cocrystals: what's in a name?," Cryst. Growth Des., 12:2147-2152 (2012).
Bedford et al., "Ubiquitin-like protein conjugation and the ubiquitin-proteasome system as drug targets," Drug Discovery, 10:29-46 (2011).
Bilal et al., "Generation of a 3D model for human cereblon using comparative modeling," J. Bioinformatics Sequence Analysis, 5(1):10-15 (2013).
Carter et al., Chemotherapy of Cancer, 2nd edition, John Wiley & Sons, New York, NY, pp. 361-367 (1981).
Chini et al., "The JAZ family of repressors is the missing link in jasmonate signalling," Nature, 448(7154):666-671 (2007).
De Graaff et al., "Matrix methods for solving protein substructures of chlorine and sulfur from anomalous data," Acta Crystallogr. D. Biol. Crystallogr., 57(Pt 12):1857-1862 (2001).
Duman et al., "Crystal structures of bacillus subtilis lon protease," J. Mol. Biol., 401(4):653-670 (2010).
Emsley et al., "Features and development of Coot," Acta Crystallogr. D. Biol. Crystallogr., 66(Pt 4):486-501 (2010).

(56) References Cited

OTHER PUBLICATIONS

Eve et al., "Single-agent lenalidomide in relapsed/refractory mantle cell lymphoma: results from a UK phase II study suggest activity and possible gender differences," *Br. J. Haematol.*, 159(2):154-163 (2012).
Gandhi et al., "Measuring cereblon as a biomarker of response or resistance to lenalidomide and pomalidomide requires use of standardized reagents and understanding of gene complexity," *Br. J. Haematol.*, 164(2):233-244 (2013).
Gerdes et al., "Emerging understanding of multiscale tumor heterogeneity," *Front. Oncol.*, 4:1-12 (2014).
Gura, "Systems for identifying new drugs are often faulty," *Science*, 278:1041-1042 (1997).
He et al., "DDB1 functions as a linker to recruit receptor WD40 proteins to CUL4-ROC1 ubiquitin ligases," *Genes Dev.*, 20(21):2949-2954 (2006).
Higa et al., "CUL4-DDB1 ubiquitin ligase interacts with multiple WD40-repeat proteins and regulates histone methylation," *Nat. Cell. Biol.*, 8(11):1277-1283 (2006).
Ito et al., "CRBN, a mental retardation-related protein, forms a novel E3 ubiquitin ligase complex with DDB1," Dai 80 Kai The Japanese Society Taikai, Dai 30 Kai The Molecular Biology Society of Japan Nenkai Godo Taikai Koen Yoshishu, pp. 4P-1011 (2007). English machine translation attached.
Kaiser, "First pass at cancer genome reveals complex landscape," *Science*, 313:1370 (2006).
Krontiris et al., *Internal Medicine*, 4th edition, Elsevier Science, Chapters 71-72, pp. 699-729 (1994).
Li et al., "A promiscuous alpha-helical motif anchors viral hijackers and substrate receptors to the CUL4-DDB1 ubiquitin ligase machinery," *Nat. Struct. Mol. Biol.*, 17(1):105-111 (2010).
Li et al., "The RIG-I-like receptor LGP2 recognizes the termini of double-stranded RNA," *J. Biol. Chem.*, 284(20):13881-13891 (2009).
Lopez-Girona et al., "Lenalidomide downregulates the cell survival factor, interferon regulatory factor-4, providing a potential mechanistic link for predicting response," *Br. J. Haematol.*,154(3):325-336 (2011).
Lu et al., "The structural basis of 5' triphosphate double-stranded RNA recognition by RIG-I C-terminal domain," *Structure*, 18(8):1032-1043 (2010).
Martiniani et al., "Biological activity of lenalidomide and its underlying therapeutic effects in multiple myeloma," *Adv. Hematol.*, 2012:842945 (2012).
McCoy et al., "Phaser crystallographic software," *J. Appl. Crystallogr.*,40(Pt 4):658-674 (2007).
Ménard et al., Cereblon (CRBN) splicing could influence response to IMiDs : A new PCR strategy to easily detect and semi-quantify loss of the IMiDs binding domain, *Blood*, 122(21):3107 (2013).
Murshudov et al., "REFMAC5 for the refinement of macromolecular crystal structures," *Acta Crystallogr. D. Biol. Crystallogr.*, 67(Pt 4):355-367 (2011).
Newman et al., "Assessment of the effectiveness of animal developmental toxicity testing for human safety," *Reprod. Toxicol.*, 7(4):359-390 (1993).
Otwinowski et al., "Processing of X-ray diffraction data collected in oscillation mode," *Methods Enzymol.*, 276:307-326 (1997).
Pannu et al., "Recent advances in the CRANK software suite for experimental phasing," *Acta Crystallogr. D.Biol. Crystallogr.*, 67(Pt 4):331-337 (2011).
Pannu et al., "The application of multivariate statistical techniques improves single-wavelength anomalous diffraction phasing," *Acta Crystallogr. D. Biol. Crystallogr.*, 60(Pt 1):22-27 (2004).
Petroski, "The ubiquitin system, disease, and drug discovery," *BMC Biochem.*, 9(Suppl. 1):S7 (2008).
Quach et al., "Mechanism of action of immunomodulatory drugs (IMiDS) in multiple myeloma," *Leukemia*, 24(1):22-32 (2010).
Ramsay et al., "Chronic lymphocytic leukemia cells induce defective LFA-1-directed T-cell motility by altering Rho GTPase signaling that is reversible with lenalidomide," *Blood*, 121(14):2704-2714 (2013).
Ramsay et al., "Multiple inhibitory ligands induce impaired T-cell immunologic synapse function in chronic lymphocytic leukemia that can be blocked with lenalidomide: establishing a reversible immune evasion mechanism in human cancer," *Blood*, 120(7):1412-1421 (2012).
Sheard et al., "Jasmonate perception by inositol-phosphate-potentiated COI1-JAZ co-receptor," *Nature*, 468(7322):400-405 (2010).
Tan et al., "Mechanism of auxin perception by the TIR1 ubiquitin ligase," *Nature*, 446(7136):640-645 (2007).
Thiel et al., "Small-molecule stabilization of protein-protein interactions: an underestimated concept in drug discovery?," *Angew Chem. Int. Ed. Engl.*, 51(9):2012-2018 (2012).
Vippagunta et al., "Crystalline solids," *Adv. Drug Del. Rev.*, 48:3-26 (2001).
Fink et al., "The novel mechanism of lenalidomide activity", retrieved from http://www.bloodjournal.org/content/bloodjournal/126/21/2366.full.pdf, 126(21):2366-2369 (2015).
Gandhi et al., "Immunomodulatory agents lenalidomide and pomalidomide co-stimulate T cells by inducing degradation of T cell repressors Ikaros and Aiolos via modulation of the E3 ubiquitin ligase complex CRL4(CRBN.)", Br J Haematol, 164(6):811-821 (2014).
Kronke et al., "Lenalidomide causes selective degradation of IKZF1 and IKZF3 in multiple myeloma cells", Science, 343(6168):301-305 (2014).

* cited by examiner

Cyno Monkey Study, Treatment Groups

| Group No. | No. of Males[a] | Test Material[c] | Dose Schedule | Dose Level (mg salt/kg) | Dose Conc. (mg salt/mL) |
|---|---|---|---|---|---|
| 1 | 5 | Vehicle[b] | QD | 0 | 0 |
| 2 | 5 | CPD 8 | QD | 0.81[f] | 0.162[f] |
| 3 | 5 | CPD 8 | Every other day[e] | 0.81[f] | 0.162[f] |
| 4 | 5 | CPD 8 | Days 1-4, 8-11, 15-18 and 22-25[f] | 0.81[f] | 0.162[f] |

Figure 6

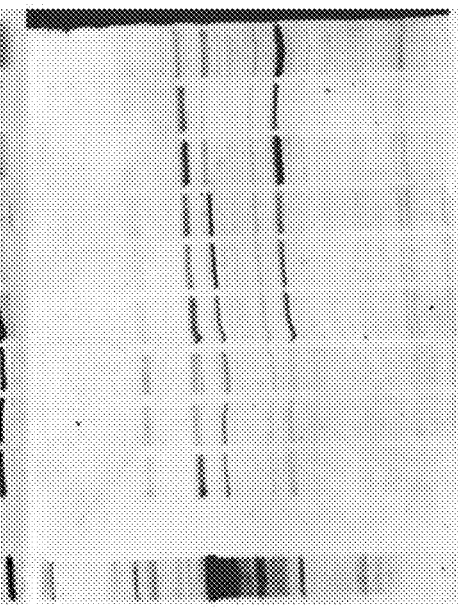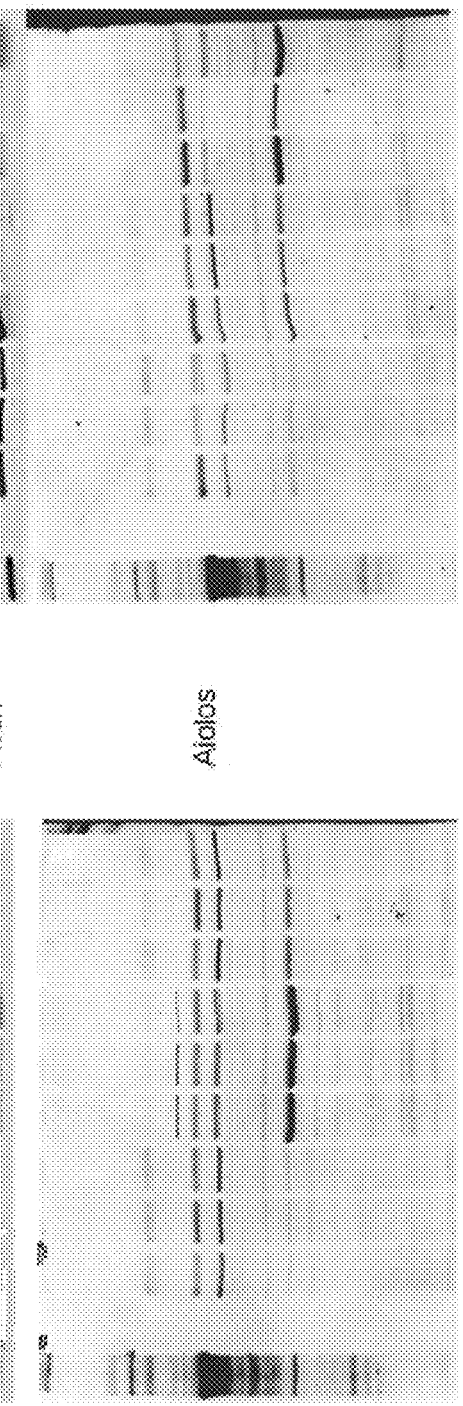
Figure 8

CPD B reduced aiolos 85 KD and increased aiolos 42 KD in several monkeys.

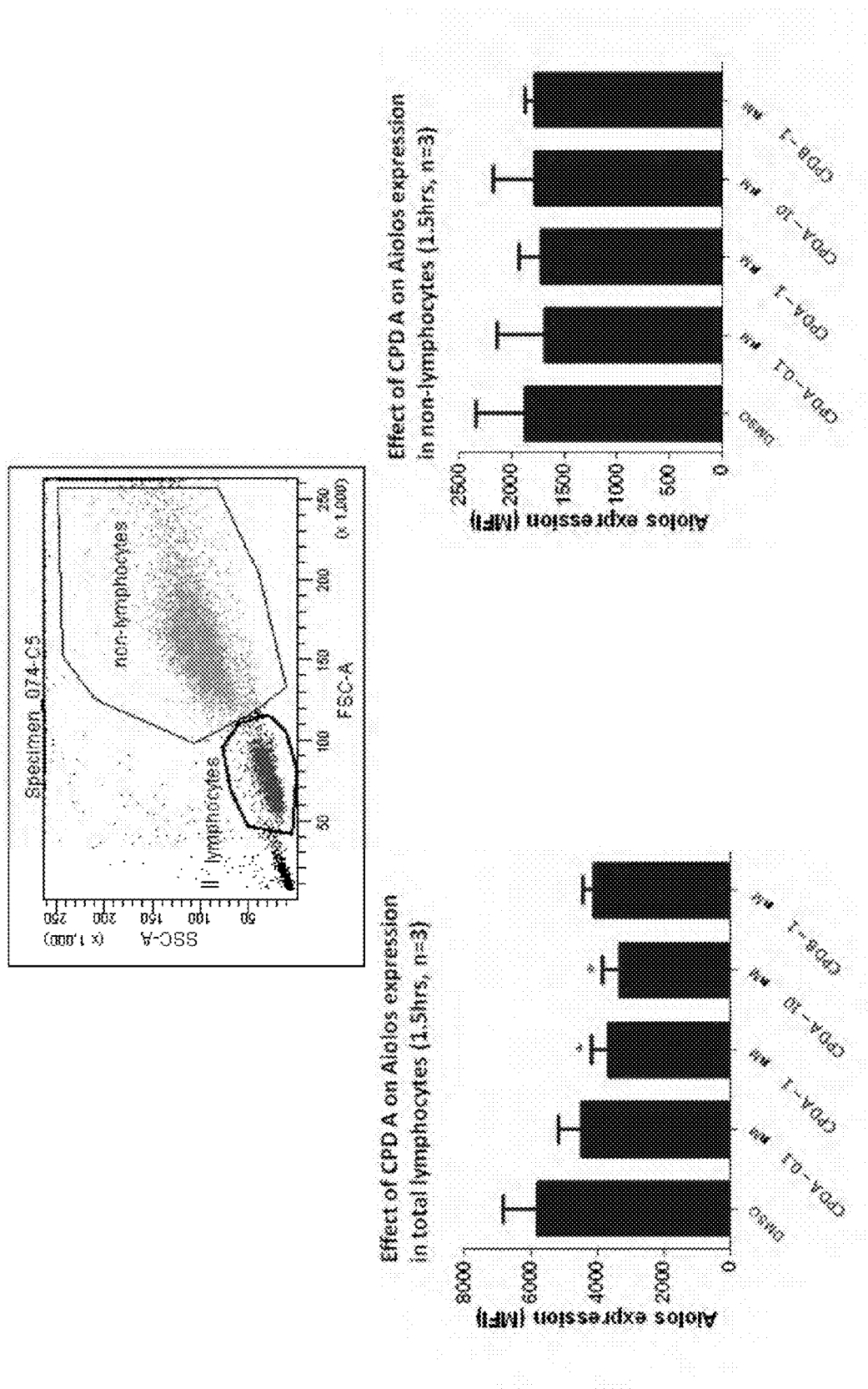

Figure 34B
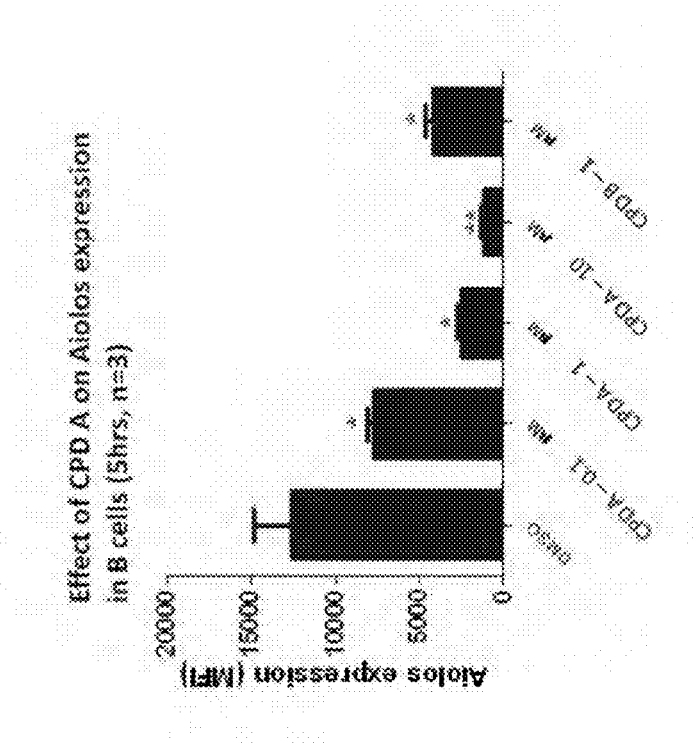
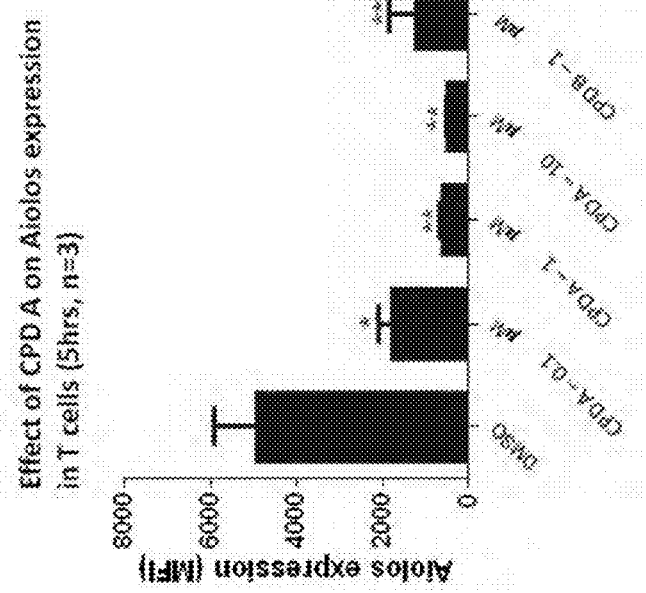

Figure 35A
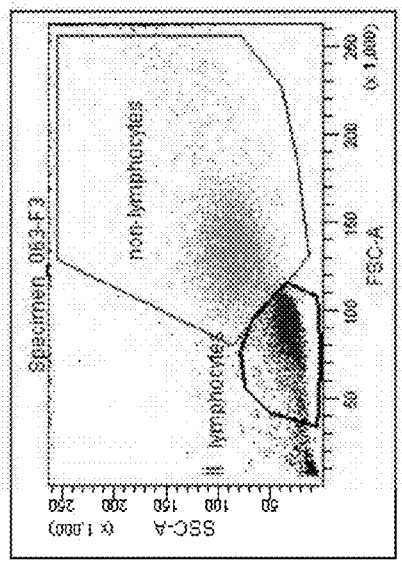
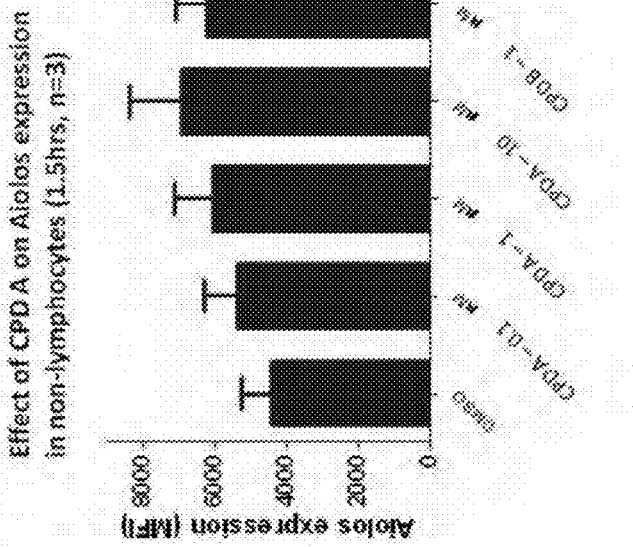
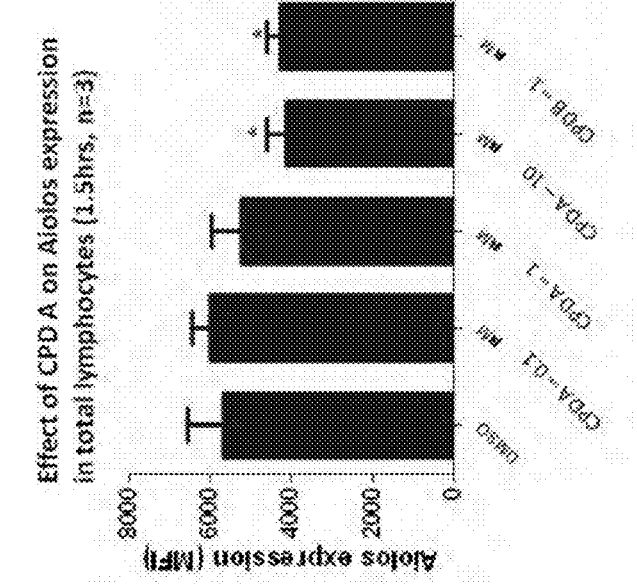

Figure 36A
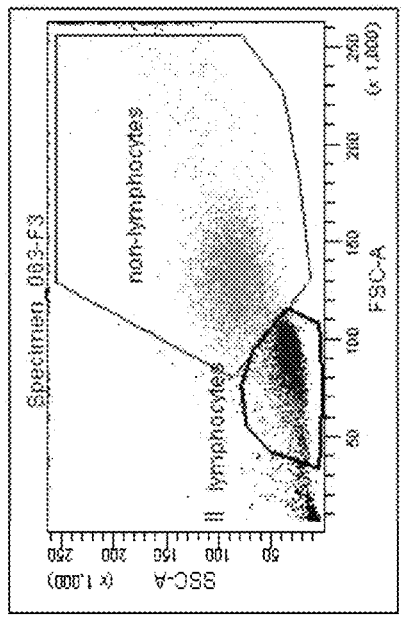
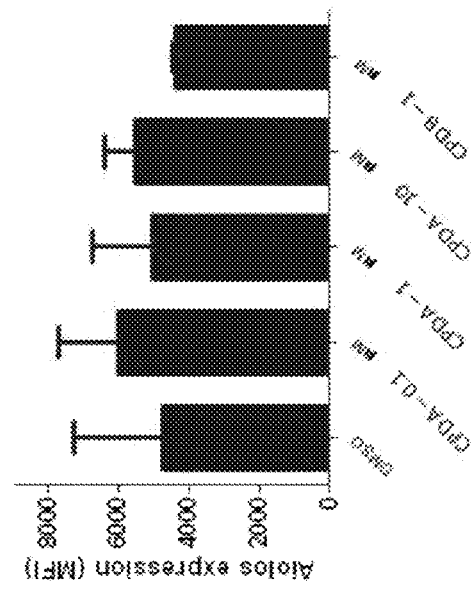
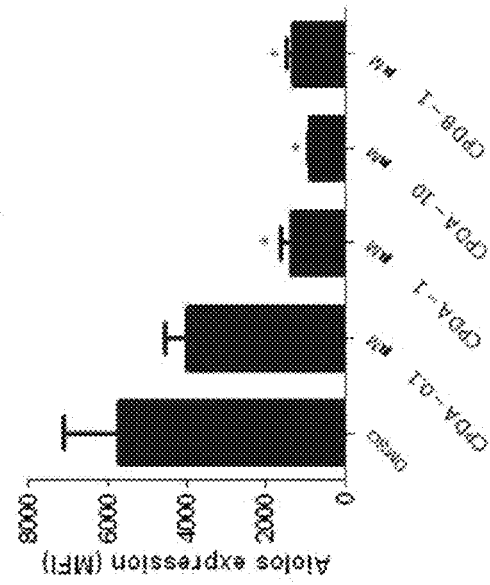

Figure 39 A, B, and C

Figure 42 A and B

Figure 43 A, B, C, and D

Figure 44 B and C
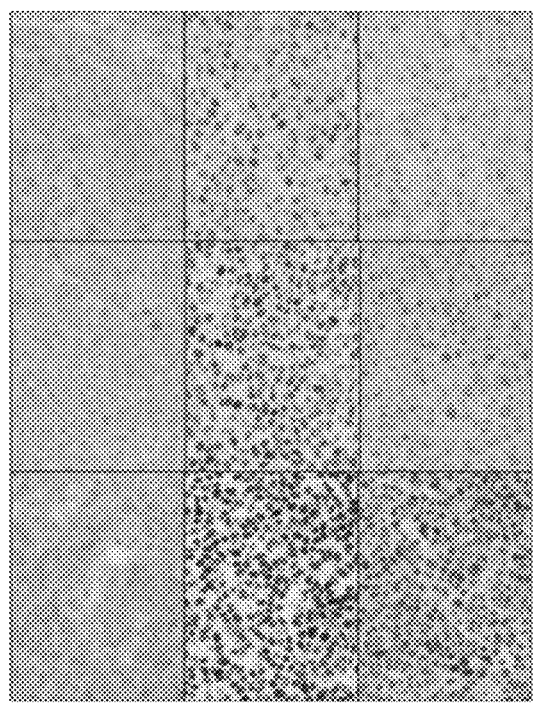
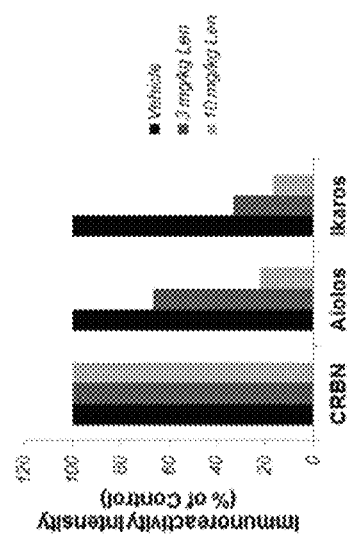

Figure 47 A and B

Figure 48 A and B

Figure 50 A, B, C, and D

Figure 51 A and B

Figure 53 A-G

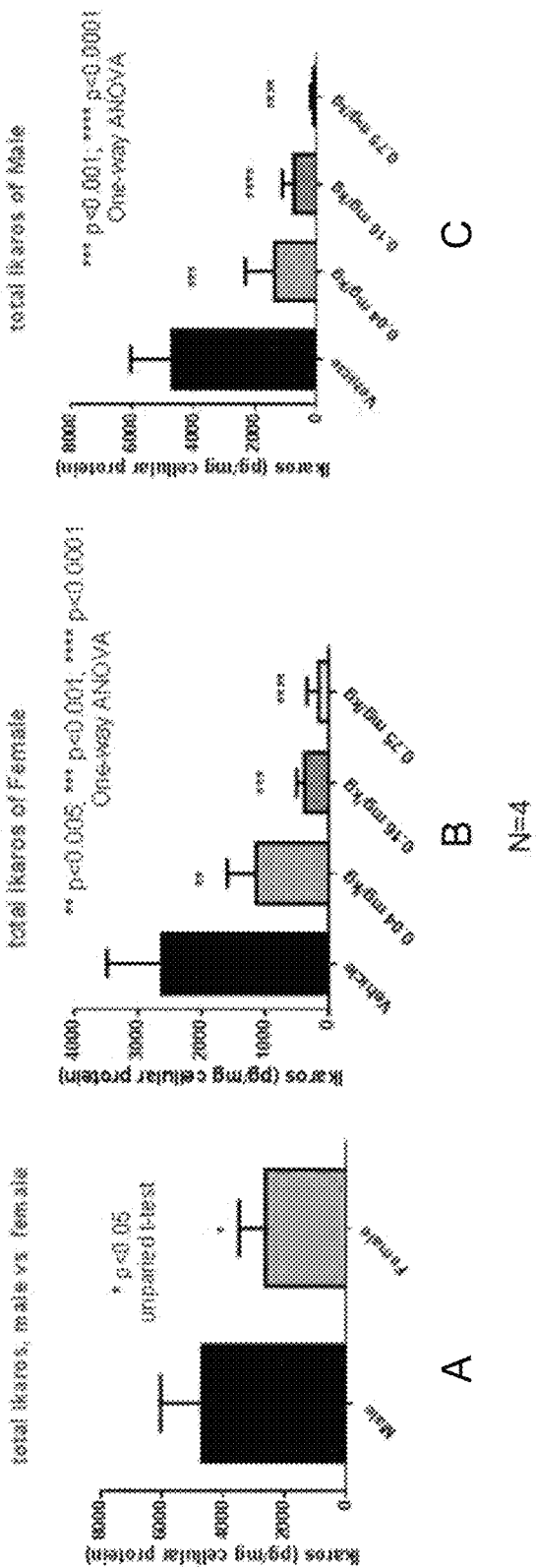
Figure 55 A, B, and C

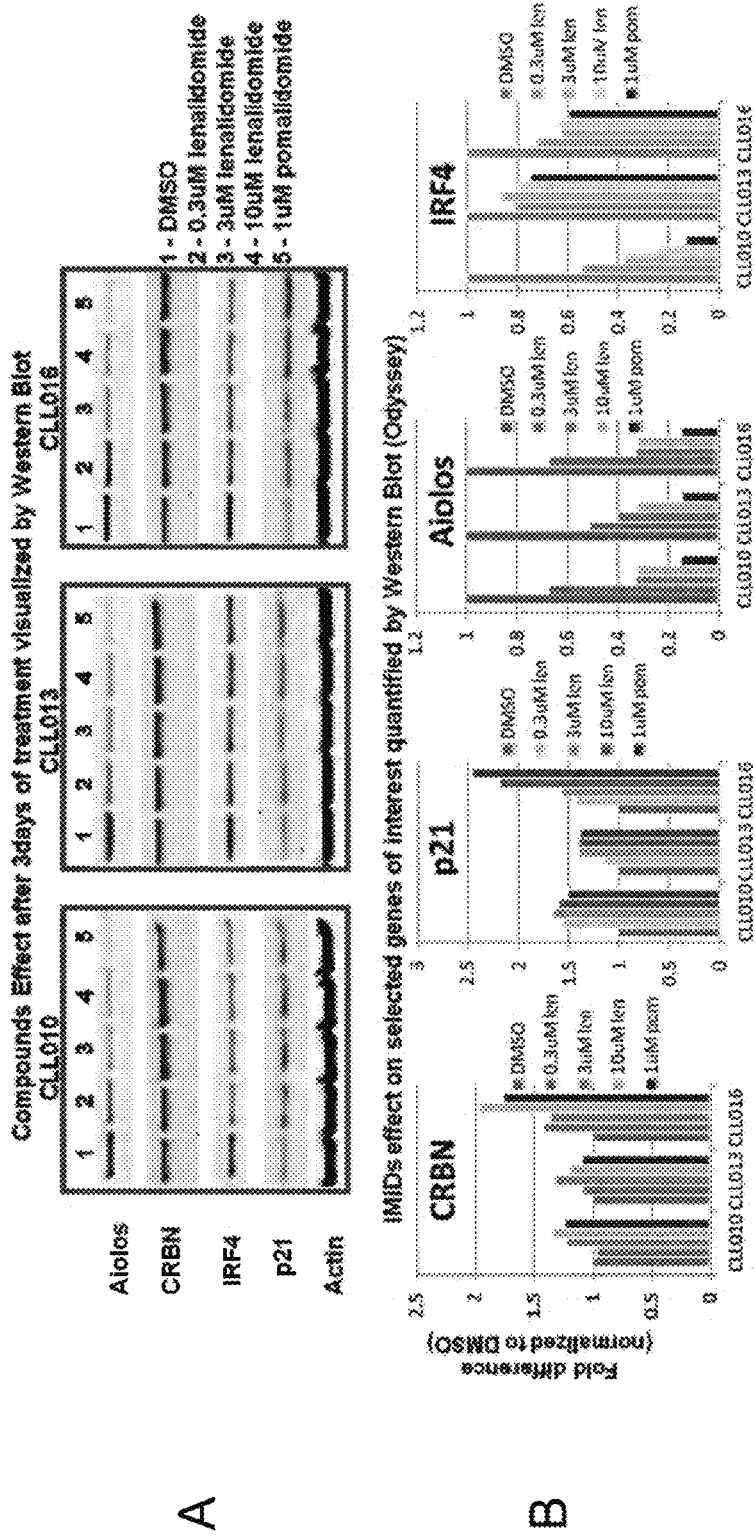
Figure 56 A and B

METHODS FOR DETERMINING DRUG EFFICACY USING CEREBLON-ASSOCIATED PROTEINS

1 CLAIM OF PRIORITY

Priority is claimed herein to U.S. Provisional Applications Nos. 61/666,703 and 61/696,752, both entitled "Methods for Determining Drug Efficacy Using Cereblon-Associated Proteins," filed Jun. 29, 2012, and Sep. 4, 2012, respectively. The above-referenced applications are incorporated by reference herein in their entirety.

2 FIELD

Provided herein are methods of determining the efficacy of an immunomodulatory compound. Also provided herein are methods of using cereblon-associated proteins as biomarkers for clinical sensitivity to cancer and inflammatory diseases, and patient response to drugs. Further provided are kits for carrying out the methods.

3 BACKGROUND

3.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., Immunology, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, blood and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma.

The diffuse large-B-cell lymphomas (DLBCL) can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference.

Although viruses reportedly cause several forms of leukemia in animals, causes of leukemia in humans are to a large extent unknown. *The Merck Manual*, 944-952 (17$^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17$^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloid leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual*, 949-952 (17$^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

Bone marrow stromal cells are well known to support CLL disease progression and resistance to chemotherapy. Disrupting the interactions between CLL cells and stromal cells is an additional target of CLL chemotherapy.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

Myelodysplastic syndrome (MDS) refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See The Merck Manual 953 (17th ed. 1999) and List et al., 1990, *J Clin. Oncol.* 8:1424. The treatment of MDS using immunomodulatory compounds is described in U.S. Patent Publication No. 2004/0220144, the entirety of which is hereby incorporated by reference.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., *Ann Oncol* 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. *Nature Rev.*, 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. The oncogenic transcription factor MYC has also been linked to tumor cell metabolism, specifically glycolysis. Id. MYC also promotes cell proliferation by glutamine metabolic pathways. Id.

AMP-activated protein kinase (AMPK) functions as a metabolic check point which tumor cells must overcome in order to proliferate. Id. Several mutations have been identified which suppress AMPK signaling in tumor cells. See Shackelford, D. B. & Shaw, R. J., *Nature Rev. Cancer*, 2009, 9: 563-575. STK11 has been identified as a tumor suppressor gene related to the role of AMPK. See Cairns, R. A., et al. *Nature Rev.*, 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.*, 2009, 361: 1058-1066; Parsons, D. W. et al., *Science*, 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, fibrosis, arthritis and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control and/or inhibit unwanted angiogenesis or inhibit the production of certain cytokines, including TNF-α, may be useful in the treatment and prevention of various diseases and conditions.

3.2 Inflammatory Diseases

Inflammation plays a fundamental role in host defenses and the progression of immune-mediated diseases. The inflammatory response is initiated in response to injury (e.g., trauma, ischemia, and foreign particles) and infection (e.g., bacterial or viral infection) by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury or infection.

Cytokines and prostaglandins control the inflammatory response, and are released in an ordered and self-limiting cascade into the blood or affected tissues. This release of cytokines and prostaglandins increases the blood flow to the area of injury or infection, and may result in redness and warmth. Some of these chemicals cause a leak of fluid into the tissues, resulting in swelling. This protective process may stimulate nerves and cause pain. These changes, when occurring for a limited period in the relevant area, work to the benefit of the body.

Tumor necrosis factor alpha (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-borne tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as psoriasis, rheumatoid arthritis, osteoarthritis, psoriatic arthritis, Crohn's disease, asthma, allergies or inflammatory bowel disease, are characterized by chronic inflammation. Inflammatory diseases such as arthritis, related arthritic conditions (e.g., osteoarthritis, rheumatoid arthritis, and psoriatic arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. Enhanced or unregulated TNF-α production plays a central role in the inflammatory response and the administration of their antagonists block chronic and acute responses in animal models of inflammatory disease.

Arthritis is a systemic autoimmune disease that can refer to a group of conditions involving damage to the joints of the body. There are over 100 different forms of arthritis. The most common form is osteoarthritis (degenerative joint disease) and other arthritis forms are rheumatoid arthritis, psoriatic arthritis, and related autoimmune diseases such as lupus and gout. Rheumatoid arthritis is characterized by a chronic inflammation of the joints. Both synovial tissue and fluid are invaded by inflammatory cells which lead to cytokine production. T cells and monocytes infiltrating the joints display an increased activation of Type 1 and 2 immune response markers.

Psoriatic arthritis is a chronic inflammatory arthritic condition affecting the skin, the joints, the insertion sites of tendons, ligaments, and fascia. Gladman, *Current Opinion in Rheumatology*, "Current concepts in psoriatic arthritis," 2002, 14:361-366, and Ruddy et al., *Rheumatology*, vol. 2, chapter 71, page 1071, 6th ed., 2001. Psoriatic arthritis is commonly associated with psoriasis. Id. Approximately 7% of patients with psoriasis develop psoriatic arthritis. The Merck Manual, 448 (17th ed., 1999). Psoriatic arthritis may appear in a variety of clinical patterns. There are five general patterns of psoriatic arthritis: arthritis of the distal interphalangeal joints, destructive arthritis, symmetric polyarthritis indistinguishable from rheumatoid arthritis, asymmetric oligoarthritis, and spondyloarthropathy. Ruddy et al., page 1073. Psoriasis appears to precede the onset of psoriatic arthritis in 60-80% of patients. Occasionally, arthritis and psoriasis appear simultaneously. Cutaneous eruptions may be preceded by the arthropathy.

Psoriasis is a chronic systemic autoimmune disease that appears on the skin. There are five types of psoriasis: plaque, guttate, inverse, pustular and erythrodermic. The most common form, plaque psoriasis, is commonly seen as red and white hues of scaly patches appearing on the top first layer of the epidermis. Some patients, though, have no dermatological symptoms. In plaque psoriasis, skin rapidly accumulates at these sites, which gives it a silvery-white appearance. Plaques frequently occur on the skin of the elbows and knees, but can affect any area, including the scalp, palms of hands and soles of feet, and genitals. In contrast to eczema, psoriasis is more likely to be found on the outer side of the joint. The disorder is a chronic recurring condition that varies in severity from minor localized patches to complete body coverage. Fingernails and toenails are frequently affected (psoriatic nail dystrophy) and can be seen as an isolated symptom. Psoriasis can also cause inflammation of the joints, which is known as psoriatic arthritis. In psoriasis, one hypothesis is that T cells become active, migrate to the dermis and trigger the release of cytokines, TNF-α in particular, which causes inflammation and the rapid proliferation of keratinocytes.

3.3 Cereblon

Cereblon (CRBN) is a 442-amino acid protein conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (CIC-2) in the retina with AMPK7 and DDB1. See Jo, S. et al., *J. Neurochem*, 2005, 94:1212-1224; Hohberger B. et al., *FEBS Lett*, 2009, 583:633-637; Angers S. et al., *Nature*, 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

Cereblon has recently been identified as a key molecular target that binds to thalidomide to cause birth defects. See Ito, T. et al., *Science*, 2010, 327:1345-1350. DDB1 was found to interact with CRBN and, thus, was indirectly associated with thalidomide. Moreover, thalidomide was able to inhibit auto-ubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A were both defective for thalidomide binding, with the double point mutant having the lowest thalidomide-binding activity. Id. A link between CRBN and the teratogenic effect of thalidomide was confirmed in animal models of zebra-fish and chick embryos. Id.

Whether binding to CRBN, the CRBN E3 ubiquitin-ligase complex, or one or more substrates of CRBN, is required for the beneficial effects of thalidomide and other drugs is yet to be established. Understanding these interactions with thalidomide and other drug targets will allow the definition of the molecular mechanisms of efficacy and/or toxicity and may lead to drugs with improved efficacy and toxicity profiles.

3.4 Compounds

A number of studies have been conducted with the aim of providing compounds that can safely and effectively be used to treat diseases associated with abnormal production of TNF-α. See, e.g., Marriott, J. B., et al., *Expert Opin. Biol. Ther.*, 2001, 1(4): 1-8; G. W. Muller, et al., *J Med Chem.*, 1996, 39(17): 3238-3240; and G. W. Muller, et al., *Bioorg & Med Chem Lett.*, 1998, 8: 2669-2674. Some studies have focused on a group of compounds selected for their capacity to potently inhibit TNF-α production by LPS stimulated PBMC. L. G. Corral, et al., *Ann. Rheum. Dis.*, 1999, 58:(Suppl I) 1107-1113. These compounds show not only potent inhibition of TNF-α but also marked inhibition of LPS induced monocyte IL1β and IL12 production. LPS induced IL6 is also inhibited by such compounds, albeit partially. These compounds are potent stimulators of LPS induced IL10. Id.

Compounds for the methods provided herein include, but are not limited to, the substituted 2-(2,6-dioxopiperidin-3-yl)phthalimides and substituted 2-(2,6-dioxopiperidin-3-yl)-1-oxoisoindoles described in U.S. Pat. Nos. 6,281,230 and 6,316,471, both to G. W. Muller, et al. Still other specific compounds disclosed herein belong to a class of isoindole-imides disclosed in U.S. Pat. Nos. 6,395,754, 6,555,554, 7,091,353, U.S. patent publication no. 2004/0029832, and International Publication No. WO 98/54170, each of which is incorporated herein by reference.

Thalidomide, lenalidomide and pomalidomide have shown remarkable responses in patients with multiple myeloma, lymphoma and other hematological diseases such as myelodysplastic syndrome. See Galustian C, et al., *Expert Opin Pharmacother.*, 2009, 10:125-133. These drugs display a broad spectrum of activity, including anti-angiogenic properties, modulation of pro-inflammatory cytokines, co-stimulation of T cells, increased NK cell toxicity, direct anti-tumor effects and modulation of stem cell differentiation.

For example, thalidomide and lenalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide may also be administered in combination with dexamethasone. U.S. Patent Publication No. 2004/0029832 A1, the disclosure of which is hereby incorporated in its entirety, discloses the treatment of multiple myeloma.

Another compound provided herein is 3-(5-amino-2-methyl-4-oxo-4H-quinazolin-3-yl)-piperidine-2,6-dione ("Compound A"), which has the following structure:

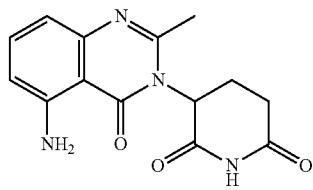

A or an enantiomer or a mixture of enantiomers thereof; or a pharmaceutically acceptable salt, solvate, hydrate, co-crystal, clathrate, or polymorph thereof.

Compound A can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional Pat. App. No. 61/451,995, filed Mar. 11, 2011, which is incorporated herein by reference in its entirety.

In certain embodiments, provided herein is 3-(4-((4-(morpholinomethyl)benzyl)oxy)-1-oxoisoindolin-2-yl)piperidine-2,6-dione. In one embodiment, provided herein is the (S) stereoisomer of 3-(4-((4-(morpholinomethyl)benzyl)oxy)-1-oxoisoindolin-2-yl)piperidine-2,6-dione ("Compound B"). Racemic 3-(4-((4-(morpholinomethyl)benzyl)oxy)-1-oxoisoindolin-2-yl)piperidine-2,6-dione, other 4'-arylmethoxy isoindoline compounds and methods of preparing the same have been reported in U.S. Patent Publication No. 2011/0196150, which is incorporated herein by reference in its entirety. Compound B has the following structure:

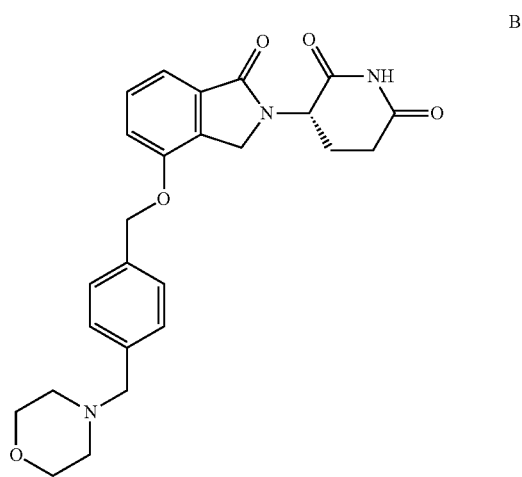 [SMILES: O=C1CC[C@H](N2Cc3c(OCc4ccc(CN5CCOCC5)cc4)cccc3C2=O)C(=O)N1]

B

The conventional methods of assessing the effects of immunomodulatory compounds require live cellular assays or lengthy clinical endpoints. These cellular tests are cumbersome and often require the use of various stimulants (e.g., lipopolysaccharide or anti-CD3 antibody). Indirect endpoints such as cytokine production are evaluated, which can be influenced via multiple pathways. Further, clinical efficacy of these compounds could not be correctly predicted, as it could only be measured in terms of patient response, which usually requires a minimum of several months of treatment. In view of the deficiencies of the conventional methods, there is a need to develop an efficient, sensitive and accurate method to detect, quantify and characterize the pharmacodynamic activity of immunomodulatory compounds.

4 SUMMARY OF THE INVENTION

In one embodiment, provided herein are methods of determining whether a compound is immunomodulatory, comprising: (a) contacting a first cell with the compound; (b)

obtaining a first sample from the first cell from step (a); (c) determining the level of a CRBN-associated protein in the first sample; and (d) comparing the level of the CRBN-associated protein from step (c) to the level of the same protein obtained from a reference sample, wherein a change in the level as compared to the reference is indicative of the efficacy of the compound as an immunomodulatory compound. In certain embodiments, the contacting in step (a) is performed in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In some embodiments, the cells are peripheral blood mononuclear cells, B cells, T cells, monocytes or granulocytes. In other embodiments, the cells are tumor or cancer cells, e.g., lymphoma, myeloma or leukemia. In one embodiment, the tumor or cancer cells are obtained from a cell line.

In certain embodiments, step (c) comprises: (i) contacting the proteins within the first sample from step (b) with a first antibody that immunospecifically binds to a CRBN-associated protein; (ii) contacting the proteins bound to the first antibody with a second antibody with a detectable label, wherein the second antibody immunospecifically binds to the CRBN-associated protein, and wherein the second antibody immunospecifically binds to a different epitope on the CRBN-associated protein than the first antibody; (iii) detecting the presence of second antibody bound to the proteins; and (iv) determining the amount of the CRBN-associated protein based on the amount of detectable label in the second antibody.

In certain embodiments, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding the CRBN-associated protein; and (iii) determining the RNA level of the CRBN-associated protein based on the amount of the amplified DNA.

In certain embodiments, the compound is immunomodulatory if the level (e.g., protein or RNA level) of the CRBN-associated protein as compared to the reference decreases. In certain embodiments, the compound is immunomodulatory if the level (e.g., protein or RNA level) of the CRBN-associated protein as compared to the reference increases. In one embodiment, the reference is prepared by using a second cell not contacted with the compound; wherein the second cell is of the same type as the first cell.

In another embodiment, provided herein are methods of assessing the efficacy of a compound in treating a disease or disorder, comprising: (a) administering a compound to a subject having the disease or disorder; (b) obtaining a first sample from the subject; (c) determining the level of a CRBN-associated protein in the first sample; and (d) comparing the level of the CRBN-associated protein from step (c) to the level of the same protein obtained from a reference sample, wherein a change in the level as compared to the reference is indicative of the efficacy of the compound in treating the disease or disorder. In certain embodiments, the disease or disorder is cancer (e.g., solid tumor or blood cancer as described in Section 5.2.3 below) or an inflammatory disease such as systemic lupus erythematosus, Sjogren syndrome, systemic sclerosis, other inflammatory or autoimmune diseases, or an inflammatory disease as described in Section 2.2 above. In certain embodiments, the disease or disorder is multiple myeloma, chronic lymphocytic leukemia, non-Hodgkins Lymphoma, mantle cell lymphoma, systemic lupus erythematosus, Sjogren syndrome, or systemic sclerosis. In some embodiments, the sample is obtained from a tumor biopsy, node biopsy, or a biopsy from bone marrow, spleen, liver, brain or breast.

In certain embodiment, step (c) comprises: (i) contacting the proteins within the first sample from step (b) with a first antibody that immunospecifically binds to a CRBN-associated protein; (ii) contacting the proteins bound to the first antibody with a second antibody with a detectable label, wherein the second antibody immunospecifically binds to the CRBN-associated protein, and wherein the second antibody immunospecifically binds to a different epitope on the CRBN-associated protein than the first antibody; (iii) detecting the presence of second antibody bound to the proteins; and (iv) determining the amount of the CRBN-associated protein based on the amount of detectable label in the second antibody.

In certain embodiment, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding the CRBN-associated protein; and (iii) determining the RNA level of the CRBN-associated protein based on the amount of the amplified DNA.

In certain embodiments, the compound is likely efficacious in treating the disease or disorder if the level (e.g., protein or RNA level) of the CRBN-associated protein as compared to the reference decreases. In certain embodiments, the compound is likely efficacious in treating the disease or disorder if the level (e.g., protein or RNA level) of the CRBN-associated protein as compared to the reference increases. In one embodiment, the reference is prepared by using a second sample obtained from the subject prior to administration of the compound to the subject; wherein the second sample is from the same source as the first sample. In another embodiment, the reference is prepared by using a second sample obtained from a healthy subject not having the disease or disorder; wherein the second sample is from the same source as the first sample.

In various embodiments of the methods provided herein, the compound is a compound provided in Section 5.3 below. In various embodiments of the methods provided herein, the immunomodulatory compound is thalidomide, lenalidomide, pomalidomide, 3-(5-amino-2-methyl-4-oxo-4H-quinazolin-3-yl)-piperidine-2,6-dione or 3-(4-((4-(morpholinomethyl)benzyl)oxy)-1-oxoisoindolin-2-yl)piperidine-2,6-dione, a stereoisomer thereof, or a pharmaceutically acceptable salt, solvate, hydrate, co-crystal, clathrate, or polymorph thereof. In one embodiment, the compound decreases the level (e.g., protein or RNA level) of the CRBN-associated protein as compared to the reference. In another embodiment, the compound increases the level (e.g., protein or RNA level) of the CRBN-associated protein as compared to the reference.

In various embodiments of the methods provided herein, the CRBN-associated protein is DNA damage-binding protein 1 (DDB1); Polyadenylate-binding protein 1 (PABPC1); Heterogeneous nuclear ribonucleoprotein R (HNRNPR); ribosomal protein L19 (RPL19); Synaptotagmin-binding, cytoplasmic RNA-interacting protein (SYNCRIP); H2A histone family, member X (H2AFX); heat shock 70 kDa protein 8 (HSPA8); aldolase A, fructose-bisphosphate (ALDOA); histone cluster 1, H2aa (H1ST1H2AA); heat shock 70 kDa protein 1A (HSPA1A); X-ray repair cross-complementing protein 6 (XRCC6); ribosomal protein L12 (RPL12); ribosomal protein 18A (RPL18A); ribosomal protein L4 (RPL4); heterogeneous nuclear ribonucleoprotein A2/B1 (HNRNPA2B1); heterogeneous nuclear ribonucleoprotein C (HNRNPC); ribosomal protein S2 (RPS2); SEC24 family member C (SEC24C); ribosomal protein L9 (RPL9); ubiquitin specific peptidase 15 (USP15); SEC24 family, member A (SEC24A); CTP synthase (CTPS); ATP-binding cassette, sub-family E (OABP) member 1 (ABCE1); eukaryotic translation elongation factor 1 alpha 1 (EEF1A1); importin 5 (IPO5); cleavage and polyadenylation specific factor 6 (CPSF6); potassium voltage-gated channel beta member 2 (KCNAB2); chromosome 7 open reading frame 42 (C7ORF42); structural maintenance of chromosomes 4 (SMC4); guanine nucleotide binding protein (G protein), beta polypeptide 3 (GNB3); H2A histone family, member Z (H2AFZ); histone cluster 1, H1c (HIST1H1C); histone cluster 1, H1d (HIST1H1D); histone cluster 1, H1e (HIST1H1E); actin, beta (ACTB); casein kinase 2, alpha 1 polypeptide (CSNK2A1); cereblon (CRBN); DEAD (Asp-Glu-Ala-Asp) box polypeptide 21 (DDX21); DEAH (Asp-Glu-Ala-His) box polypeptide 9 (DHX9); DnaJ (Hsp40) homolog, subfamily C, member 1 (DNAJC1); GTPase activating protein (SH3 domain) binding protein 1 (G3BP1); heat shock 70 kDa protein 1B (HSPA1B); insulin-like growth factor 2 mRNA binding protein 2 (IGF2BP2); ribosomal protein L10a (RPL10A); ribosomal protein L13a (RPL13A); ribosomal protein L14 (RPL14); ribosomal protein L15 (RPL15); ribosomal protein L21 (RPL21); RPL3; ribosomal protein L30 (RPL30); ribosomal protein L7 (RPL7); ribosomal protein L7a (RPL7A); ribosomal protein, large, P1 (RPLP1); ribosomal protein, large, P2 (RPLP2); myosin, heavy chain 10, non-muscle (MYH10); interleukin enhancer binding factor 3, 90 kDa (ILF3); nucleolin (NCL); ribosomal protein S13 (RPS13); ribosomal protein S16 (RPS16); ribosomal protein S19 (RPS19); ribosomal protein S6 (RPS6); staphylococcal nuclease and tudor domain containing 1 (SND1); eukaryotic translation initiation factor 2, subunit 2 beta, 38 kDa (EIF2S2); heterogeneous nuclear ribonucleoprotein H2 (H') (HNRNPH2); ubiquitin B (UBB); eukaryotic translation elongation factor 1 gamma (EEF1G); transducin (beta)-like 1 X-linked receptor 1 (TBL1XR1); nascent polypeptide-associated complex alpha subunit (NACA); eukaryotic translation initiation factor 4A, isoform 1 (EIF4A1); fatty acid synthase (FASN); phosphoribosyl pyrophosphate amidotransferase (PPAT); GTPase activating protein (SH3 domain) binding protein 2 (G3BP2); tubulin, alpha 1a (TUBA1A); ubiquitin associated protein 2-like (UBAP2L); minichromosome maintenance complex component 2 (MCM2); UDP-N-acteylglucosamine pyrophosphorylase 1 (UAP1); tubulin, alpha 1c (TUBA1C); eukaryotic translation initiation factor 2, subunit 1 alpha, 35 kDa (EIF2S1); eukaryotic translation initiation factor 3, subunit J (EIF3J); protein kinase, DNA-activated, catalytic polypeptide (PRKDC); minichromosome maintenance complex component 7 (MCM7); ribosomal protein L11 (RPL11); tubulin, alpha 1b (TUBA1B); signal transducer and activator of transcription 3 (STAT3); peptidyl-tRNA hydrolase 2 (PTRH2); poly(A) binding protein, cytoplasmic 4 (PABPC4); protein tyrosine phosphatase, receptor type, C (PTPRC); microtubule-actin crosslinking factor 1 (MACF1); ubiquitin-conjugating enzyme E2O (UBE2O); deoxyuridine triphosphatase (DUT); guanine nucleotide binding protein (G protein), beta polypeptide 2-like 1 (GNB2L1); nucleoporin 88 kDa (NUP88); H2A histone family, member J (H2AFJ); Sec23 homolog B (S. cerevisiae) (SEC23B); pyridoxal (pyridoxine, vitamin B6) kinase (PDXK); ATP citrate lyase (ACLY); AT rich interactive domain 1A (SWI-like) (ARID1A); glucan (1,4-alpha-), branching enzyme 1 (GBE1); heat shock 70 kDa protein 9 (mortalin) (HSPA9); DEAD (Asp-Glu-Ala-Asp) box polypeptide 17 (DDX17); far upstream element (FUSE) binding protein 1 (FUBP1); F-box protein 21 (FBXO21); Ewing sarcoma breakpoint region 1 (EWSR1); interferon, gamma-inducible protein 16 (IFI16); tyrosine 3-monooxygenase/ tryptophan 5-monooxygenase activation protein, epsilon polypeptide (YWHAE); ubiquitin A-52 residue ribosomal protein fusion product 1 (UBA52); COP9 constitutive photomorphogenic homolog subunit 6 (Arabidopsis) (COPSE); GNAS complex locus (GNAS); ubiquitin-conjugating enzyme E2Q family member 1 (UBE2Q1); fermitin family member 3 (FERMT3); nucleosome assembly protein 1-like 2 (NAP1L2); tumor protein D52 (TPD52); VAMP (vesicle-associated membrane protein)-associated protein A, 33 kDa (VAPA); eukaryotic translation elongation factor 1 alpha-like 3 (EEF1AL3); DNA-damage-inducible transcript 4 (DDIT4); neural precursor cell expressed, developmentally down-regulated 8 (NEDD8); histone cluster 1, H1a (HIST1H1A); histone cluster 1, H1b (HIST1H1B); pericentriolar material 1 (PCM1) ikaros zinc finger protein 1 (IKZF1, Ikaros) or ikaros zinc finger protein 3 (IKZF3, Aiolos).

In one embodiment of the methods provided herein, the CRBN-associated protein is IKZF3 (also known as "Aiolos"). In another embodiment of the methods provided herein, the CRBN-associated protein is IKZF3 having a molecular weight of 58 kDa. In another embodiment of the methods provided herein, the CRBN-associated protein is IKZF3 having a molecular weight of 42 kDa. In another embodiment, the compounds provided herein down-regulate Aiolos expression (e.g., protein or gene expression). In another embodiment, the compound is pomalidomide and Aiolos expression (e.g., protein or gene expression) is down-regulated. In another embodiment, the compound is lenalidomide and Aiolos expression (e.g., protein or gene expression) is down-regulated. In another embodiment, the compound is 3-(5-amino-2-methyl-4-oxo-4H-quinazolin-3-yl)-piperidine-2,6-dione and Aiolos expression (e.g., protein or gene expression) is down-regulated. In another embodiment, the compound is 3-(4-((4-(morpholinomethyl)benzyl)oxy)-1-oxoisoindolin-2-yl)piperidine-2,6-dione and Aiolos expression (e.g., protein or gene expression) is down-regulated. In another embodiment, the compound is the (S) stereoisomer of 3-(4-((4-(morpholinomethyl)benzyl)oxy)-1-oxoisoindolin-2-yl)piperidine-2,6-dione and Aiolos expression (e.g., protein or gene expression) is down-regulated.

In another embodiment of the methods provided herein, the CRBN-associated protein is IKZF1 (also known as "Ikaros"). In another embodiment, the compounds provided herein down-regulate Ikaros expression (e.g., protein or gene expression). In another embodiment, the compound is pomalidomide and Ikaros expression (e.g., protein or gene expression) is down-regulated. In another embodiment, the compound is lenalidomide and Ikaros expression (e.g., protein or gene expression) is down-regulated. In another embodiment, the compound is 3-(5-amino-2-methyl-4-oxo-4H-quinazolin-3-yl)-piperidine-2,6-dione and Ikaros expression (e.g., protein or gene expression) is down-regulated. In another embodiment, the compound is 3-(4-((4-(morpholinomethyl)benzyl)oxy)-1-oxoisoindolin-2-yl)piperidine-2,6-dione and Ikaros expression (e.g., protein or gene expression) is down-regulated. In another embodiment, the compound is the (S) stereoisomer of 3-(4-((4-(morpholinomethyl)benzyl)oxy)-1-oxoisoindolin-2-yl)piperidine-2,6-dione and Ikaros expression (e.g., protein or gene expression) is down-regulated.

In another embodiment, provided herein are kits for carrying out the methods provided herein.

5 BRIEF DESCRIPTION OF THE FIGURES

Figure 5:
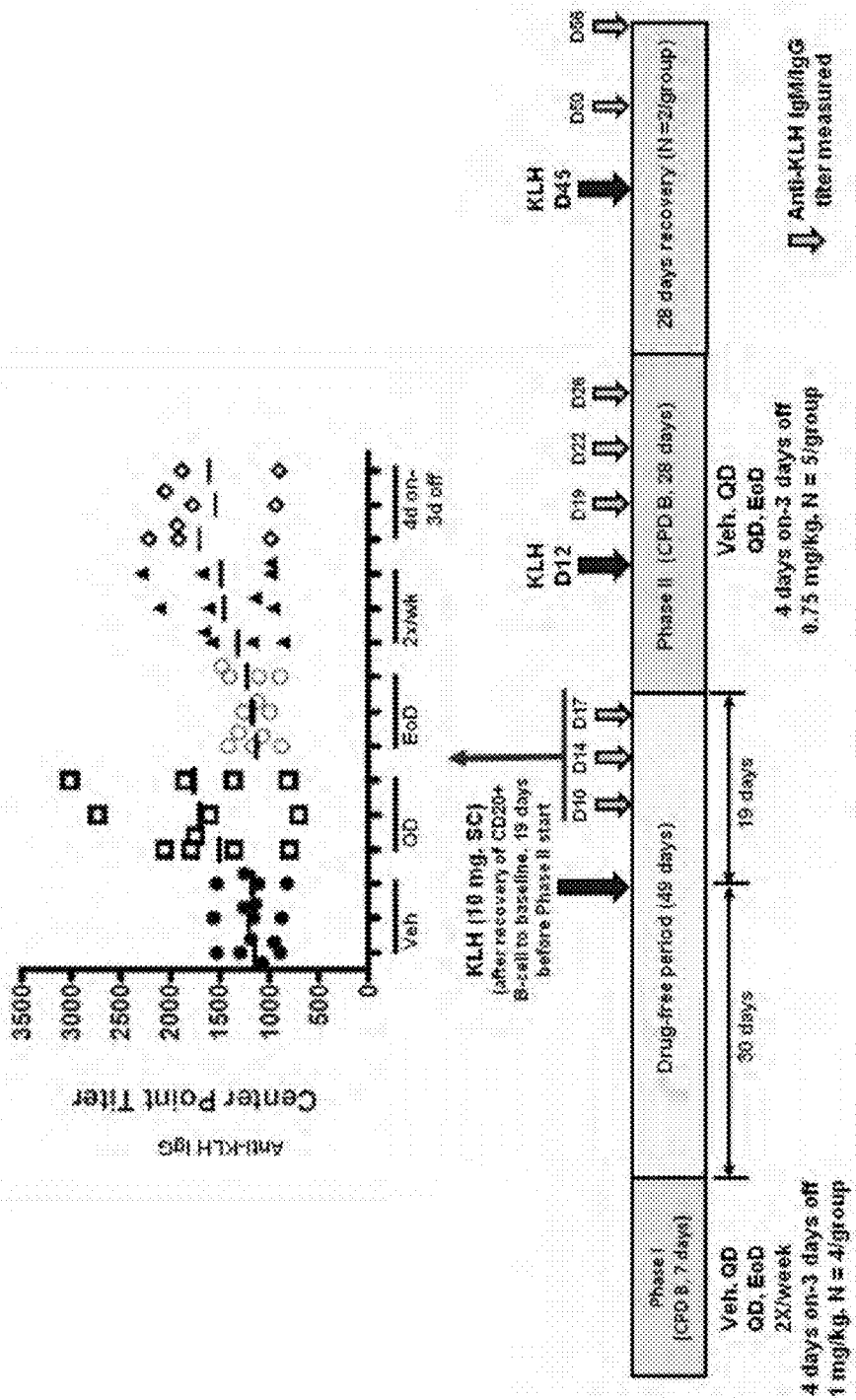

FIG. 5 shows Compound B in monkey T-dependent antibody response (TDAR) dose scheduling study. The Top panel shows the titer of various treatments, Vehicle, QD, EoD, 2×/wk and 4 d on/3 d off. The Bottom schematic depicts the dose scheduling.

FIG. 6 shows treatment groups 1-4 in the Cyno Monkey Study.

Figure 7:
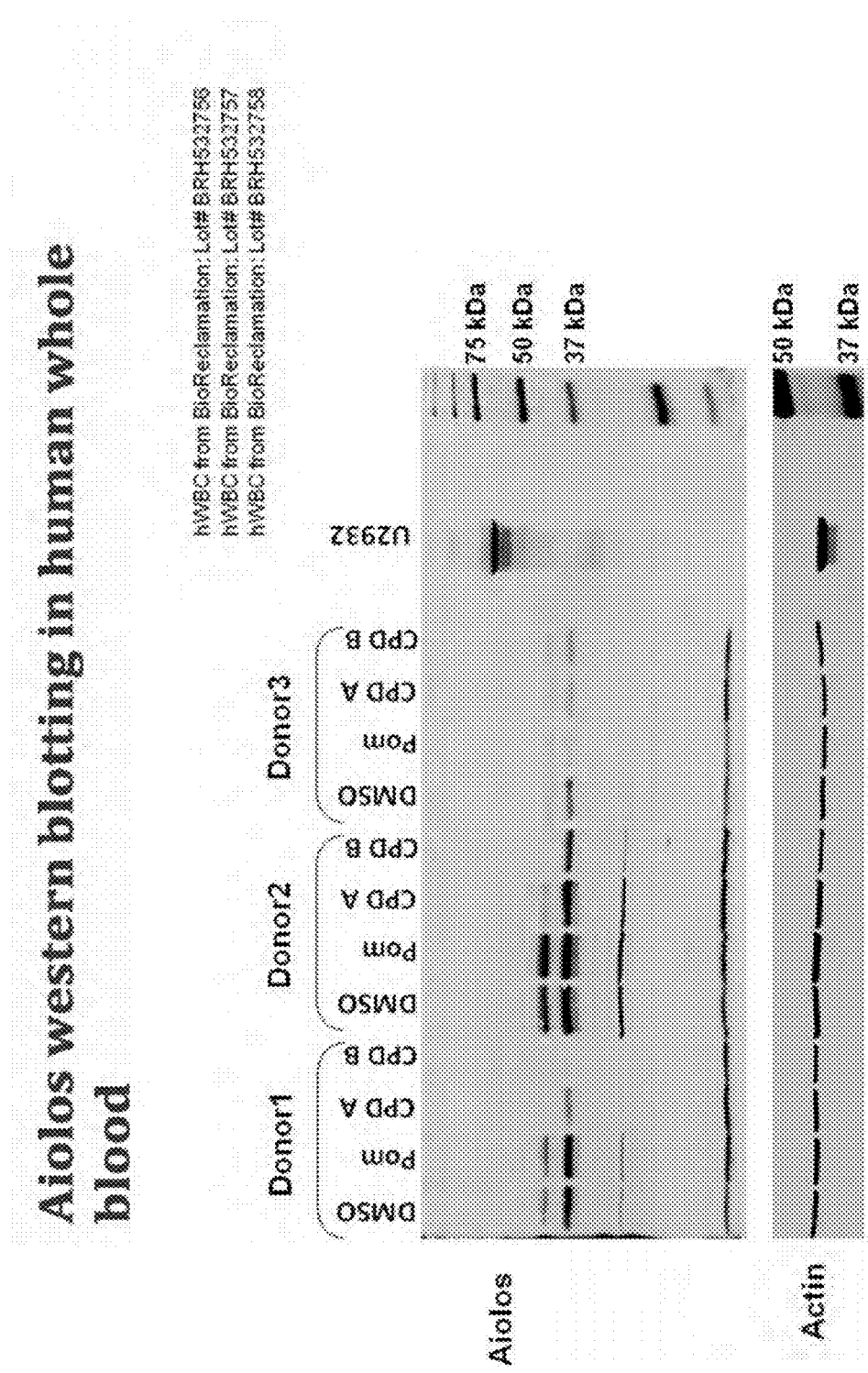

FIG. 7 shows Aiolos Western blotting in human whole blood. Whole blood samples were treated with compounds or DMSO at 250 nM for 18 h and then subjected to PBMC preparation and IB.

FIG. 8 shows Aiolos Western blotting in monkey PBMCs. Mauritius Monkey PBMCs were treated with DMSO or Compound B at 2 nM and 200 nM. The Left panel is treatment at 0 hours and the Right panel is treatment at 18 hours.

Figure 9:
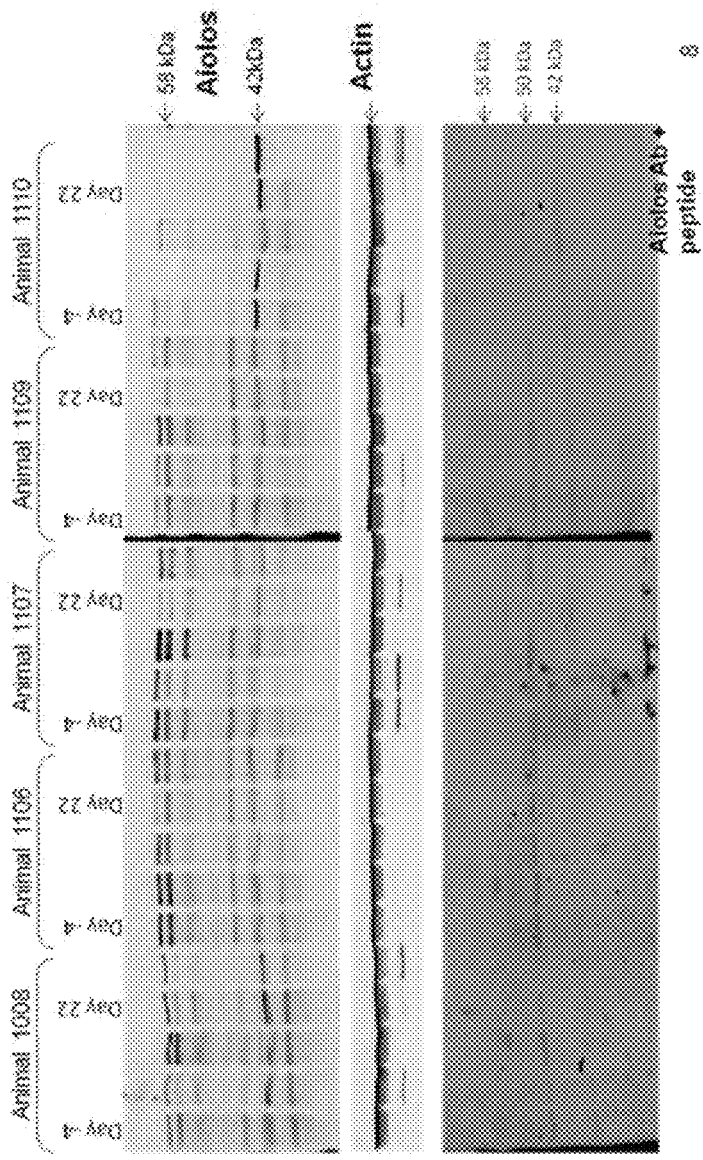

FIG. 9 shows Aiolos Western blotting in the Cyno Monkey Study, Group 1, vehicle control.

Figure 10:
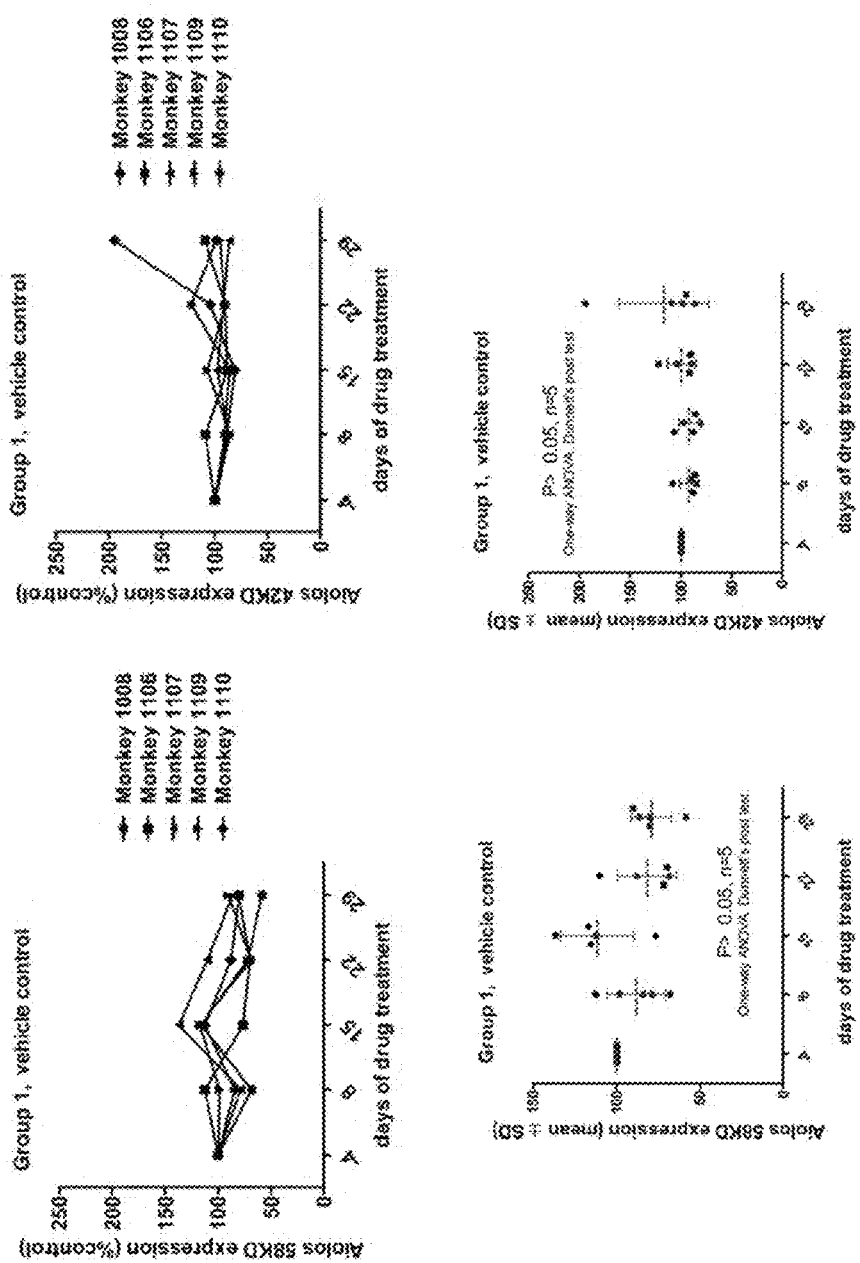

FIG. 10 shows graphical representations of Aiolos 58 kD (Left panels) and 42 kD expression (Right panels) in the Cyno Monkey Study, Group 1, vehicle control.

Figure 11:
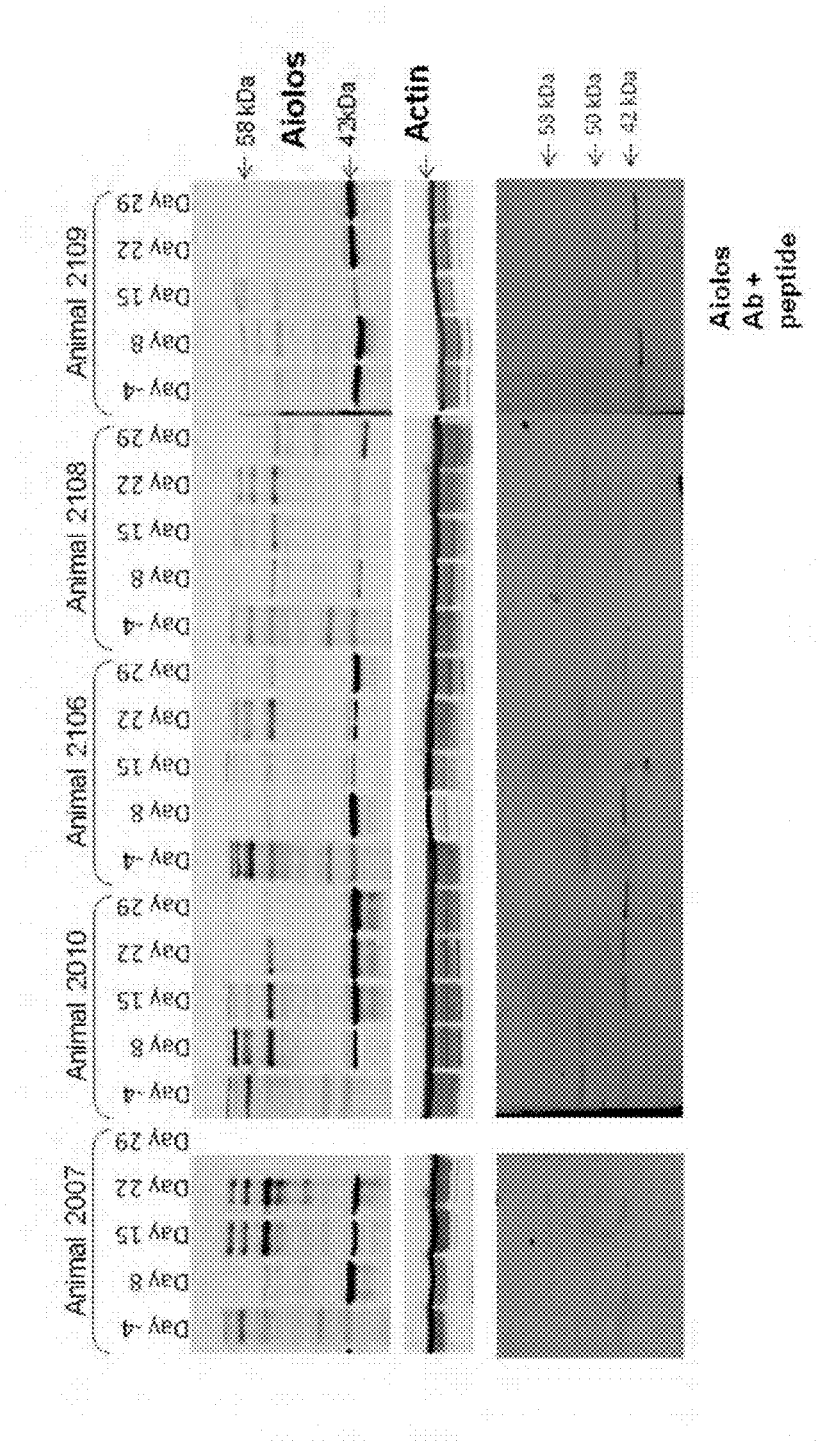

FIG. 11 shows Aiolos Western blotting in the Cyno Monkey Study, Group 2, Compound B QD dosing. Compound B reduced Aiolos 58 kD and increased Aiolos 42 kD in several monkeys.

Figure 12:
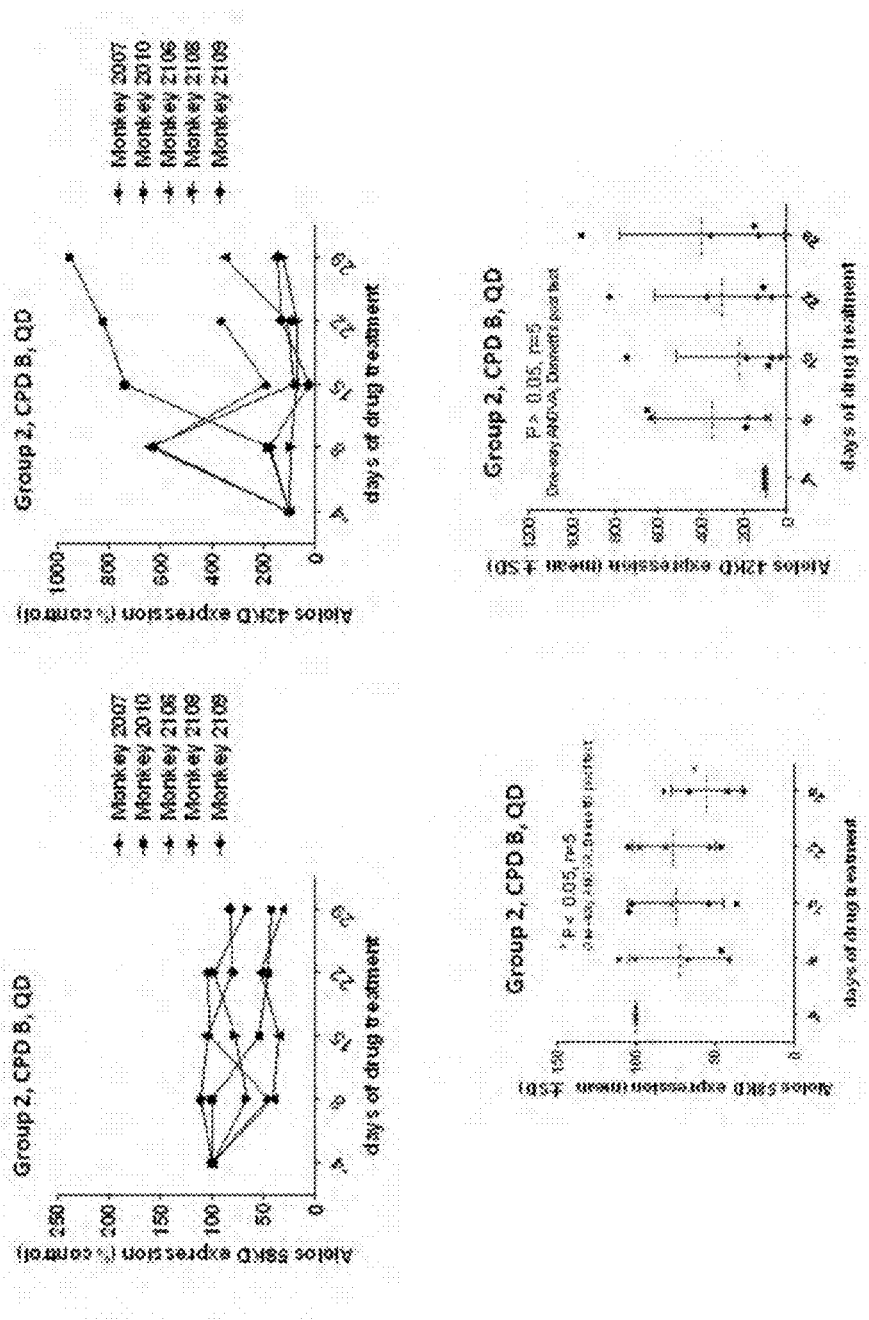

FIG. 12 shows graphical representations of Aiolos 58 kD (Left panels) and 42 kD expression (Right panels) in the Cyno Monkey Study, Group 2, Compound B QD dosing.

Figure 13:
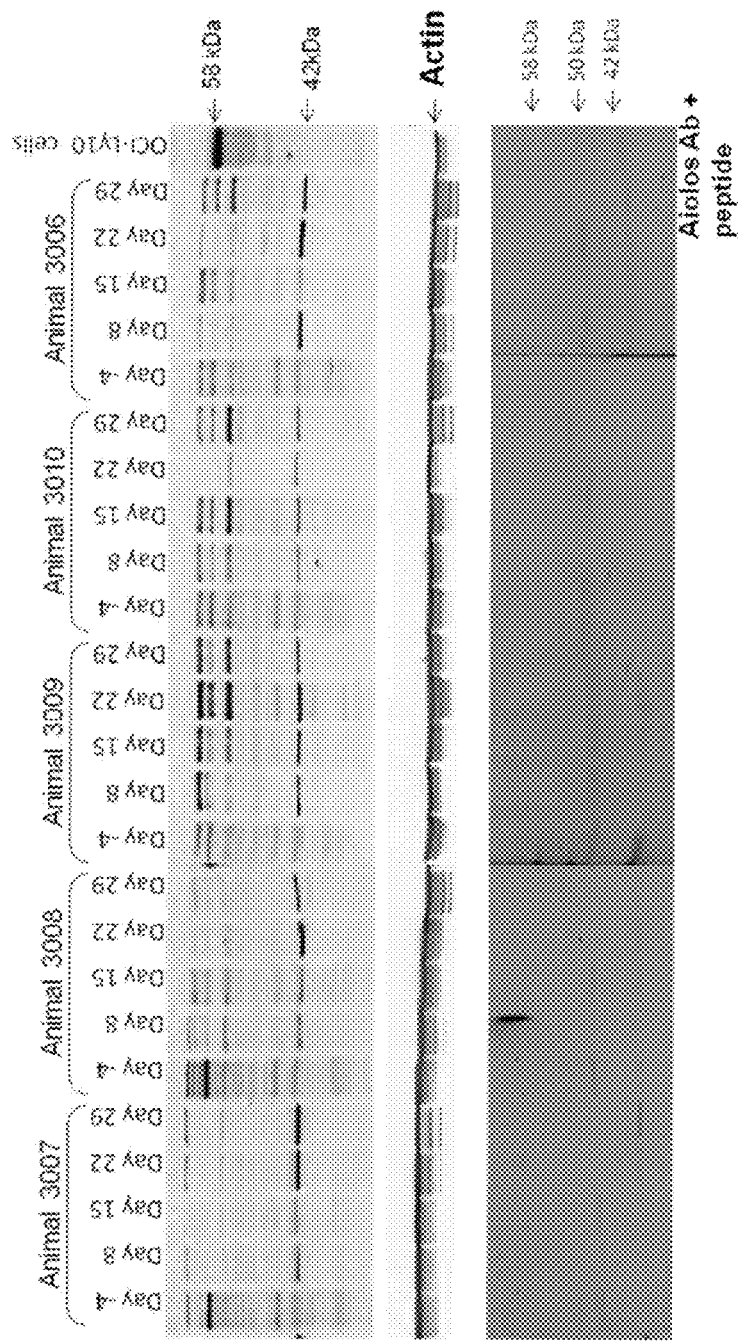

FIG. 13 shows Aiolos Western blotting in the Cyno Monkey Study, Group 3, Compound B Q2D dosing. Compound B reduced Aiolos 58 kD and increased Aiolos 42 kD in several monkeys.

Figure 14:
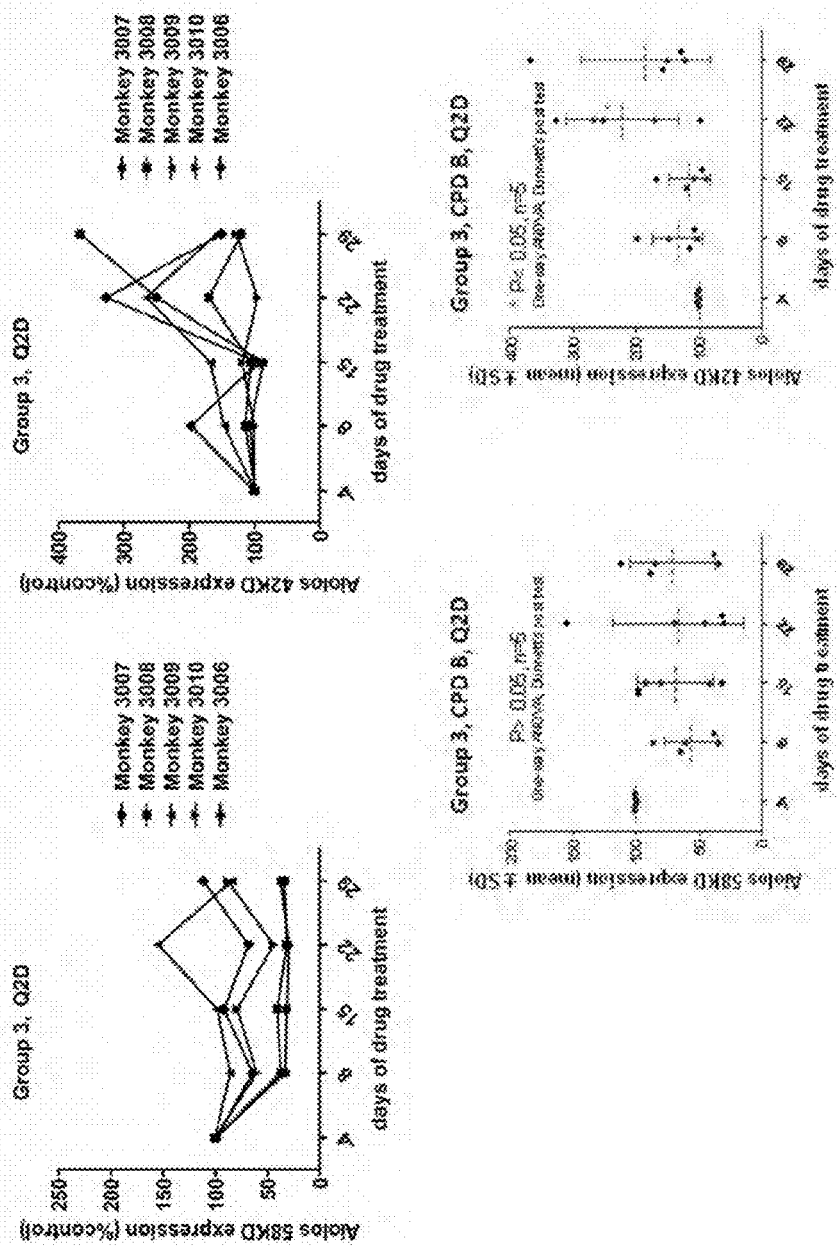

FIG. 14 shows graphical representations of Aiolos 58 kD (Left panels) and 42 kD expression (Right panels) in the Cyno Monkey Study, Group 3, Compound B Q2D dosing.

Figure 15:
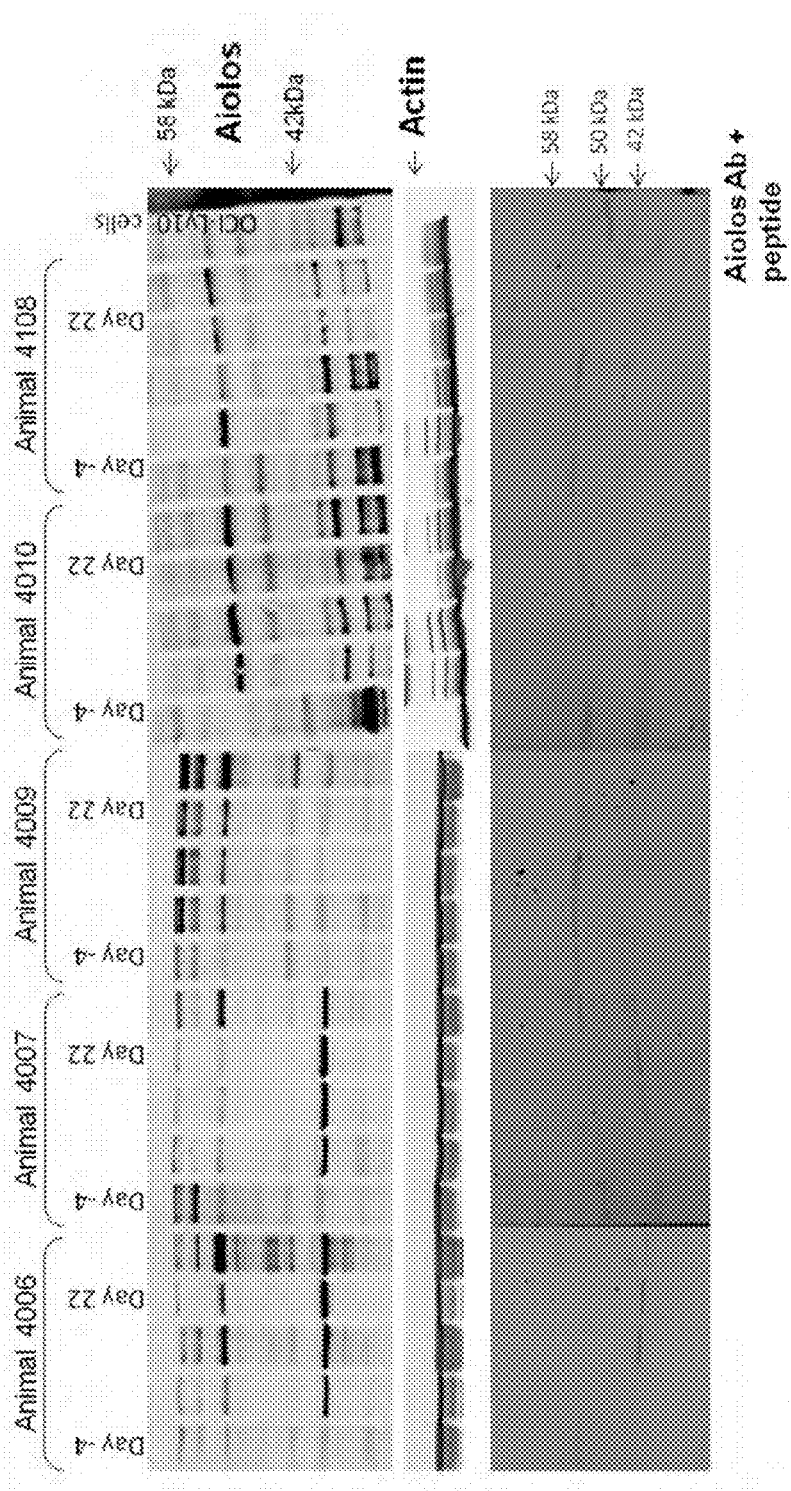

FIG. 15 shows Aiolos Western blotting in the Cyno Monkey Study, Group 4, Compound B 4 day/week dosing. Compound B reduced Aiolos 58 kD and increased Aiolos 42 kD in several monkeys.

Figure 16:
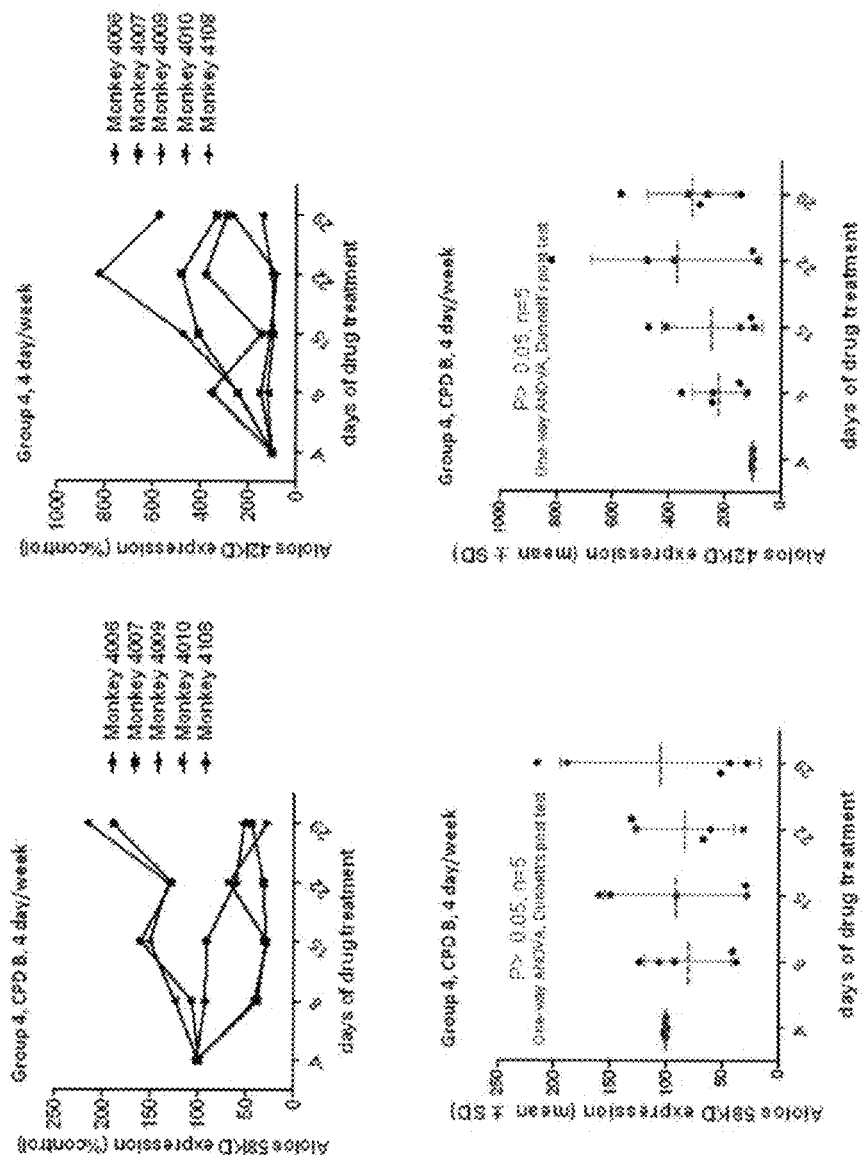

FIG. 16 shows graphical representations of Aiolos 58 kD (Left panels) and 42 kD expression (Right panels) in the Cyno Monkey Study, Group 4, Compound B 4 day/week dosing.

Figure 17:
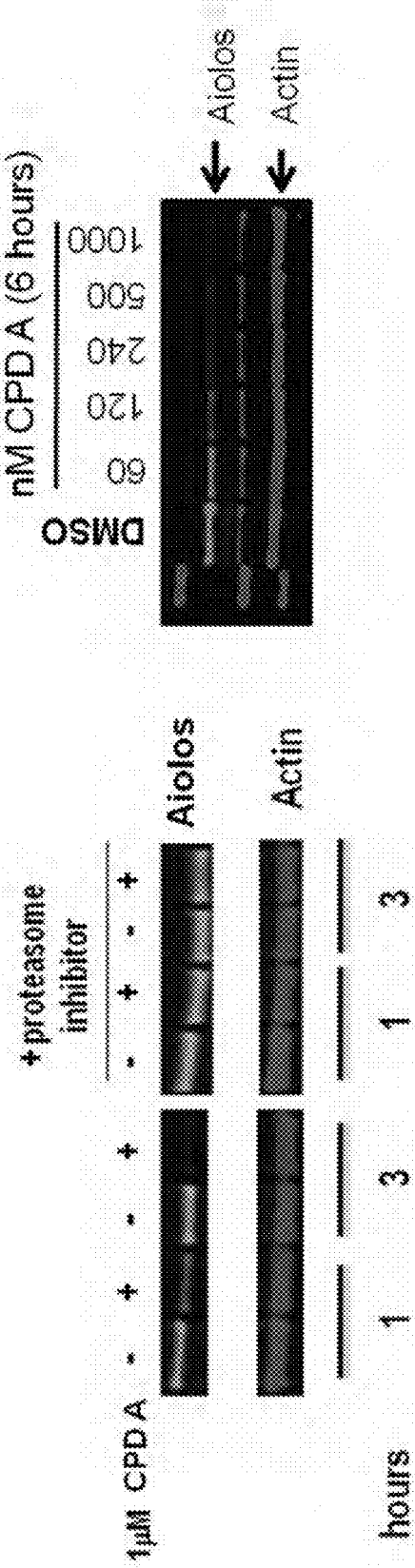

FIG. 17 shows that immunomodulatory derivatives of thalidomide (IMiD compounds) regulate transcription factor Aiolos via degradation in T cells. Compound A inhibits Aiolos protein expression in a concentration-dependent manner at clinically relevant concentrations.

Figure 18:
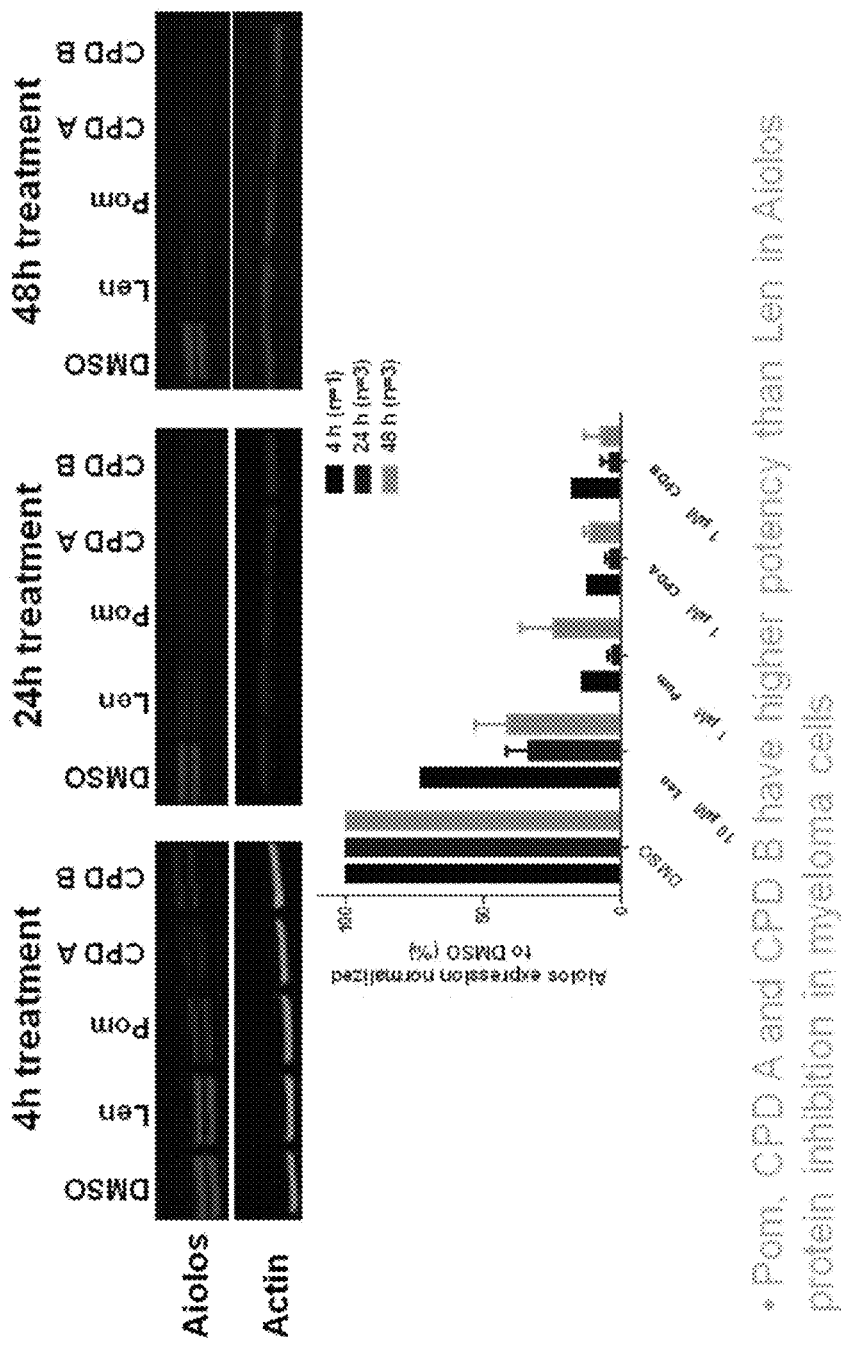

FIG. 18 shows differential effect of IMiDs on Aiolos protein. The effect appears to correlate with compound's anti-proliferative activity in Myeloma cells. Pom, Compound A and Compound B have higher potency than Len in Aiolos protein inhibition in myeloma cells.

Figure 19:
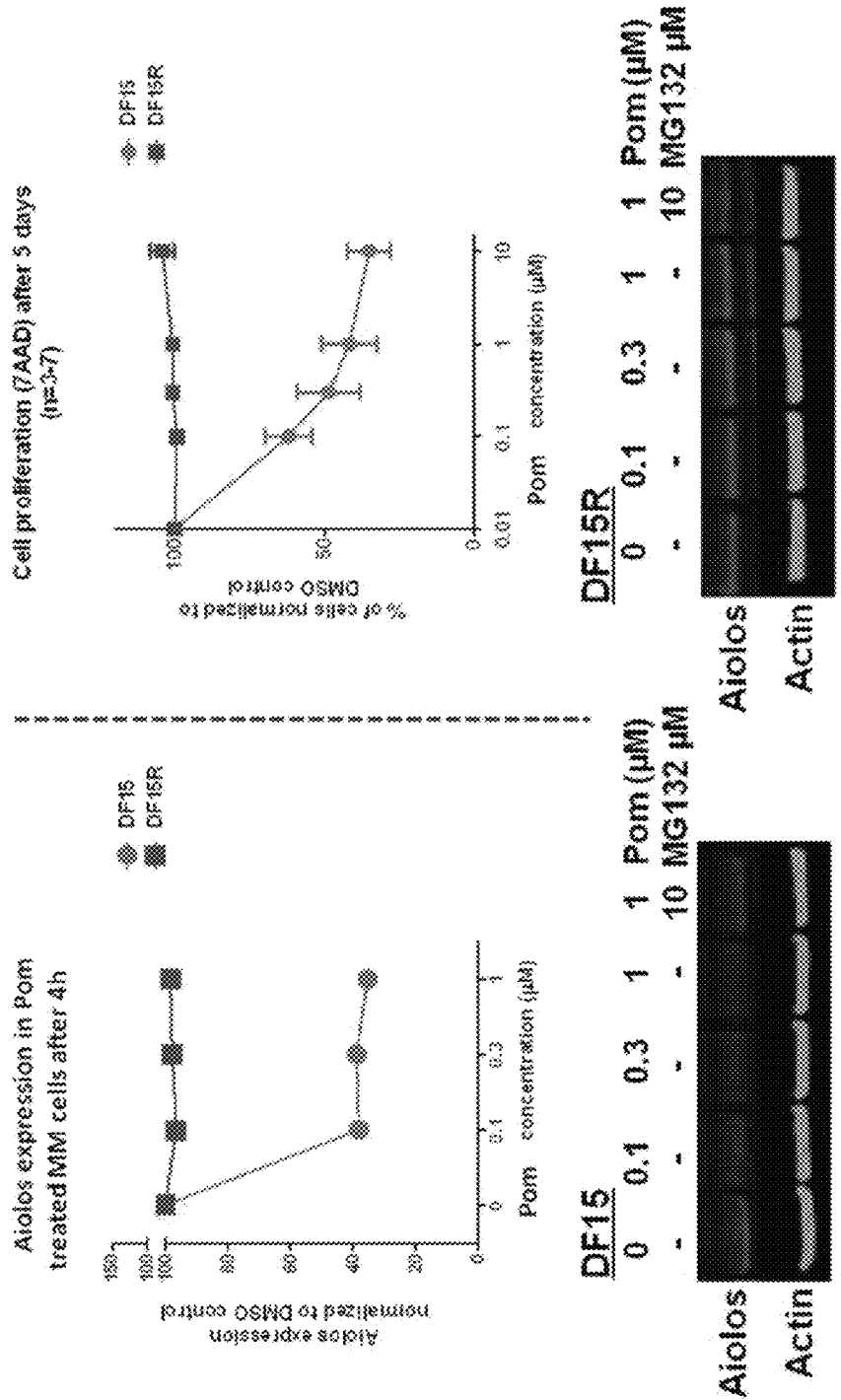

FIG. 19 shows the regulation of Aiolos by IMiDs. The regulation is abrogated in cell lines with low CRBN expression. The Left panel shows dose response with pomalidomide at 4 hours. The Right panel shows cell proliferation after 5 days (n=3-7).

Figure 20:
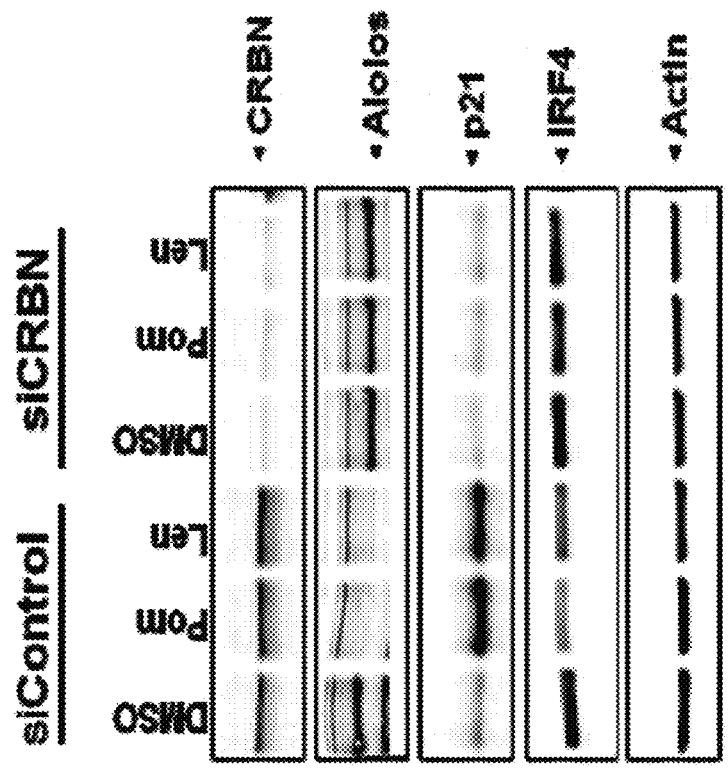

FIG. 20 shows that loss of CRBN protein prevents down-regulation of Aiolos by lenalidomide and pomalidomide. Decrease of Aiolos expression by lanalidomide or pomalidomide requires CRBN protein.

Figure 21:
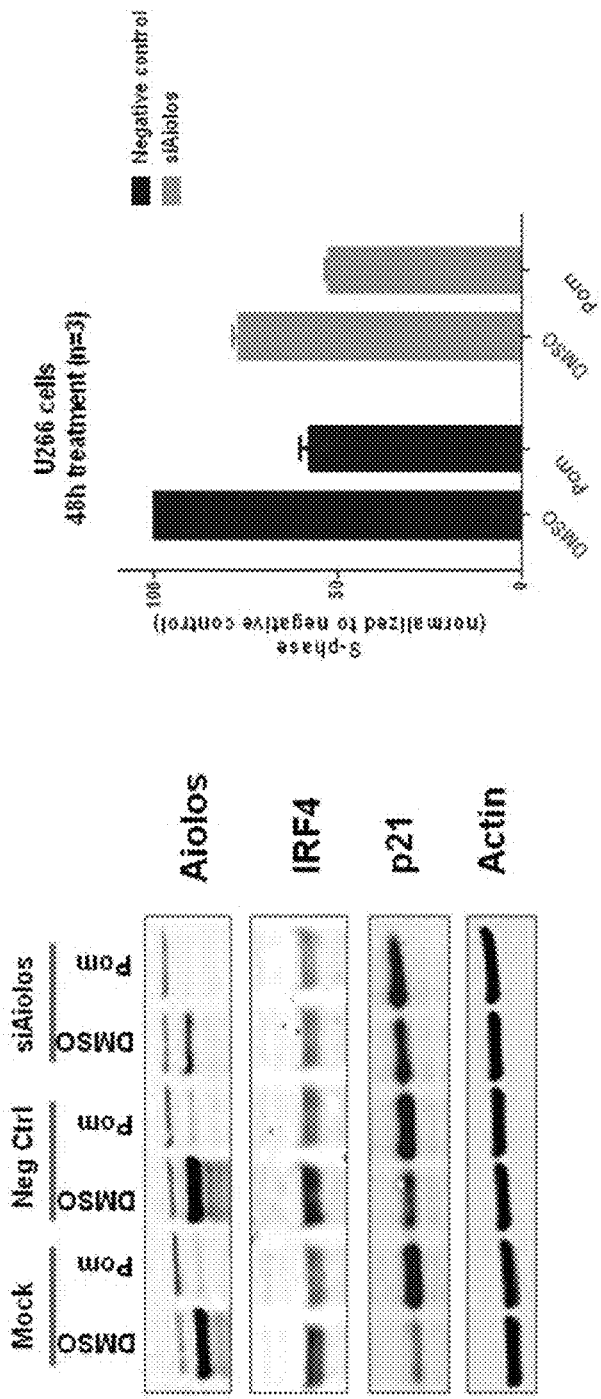

FIG. 21 shows that Aiolos knockdown is similar to IMiDs treatment where knockdown induces p21 expression, decreases IRF4 and decreases the number of cells in S phase. Aiolos is required for IRF4 expression and cell cycle progression in U266 cells.

Figure 22:
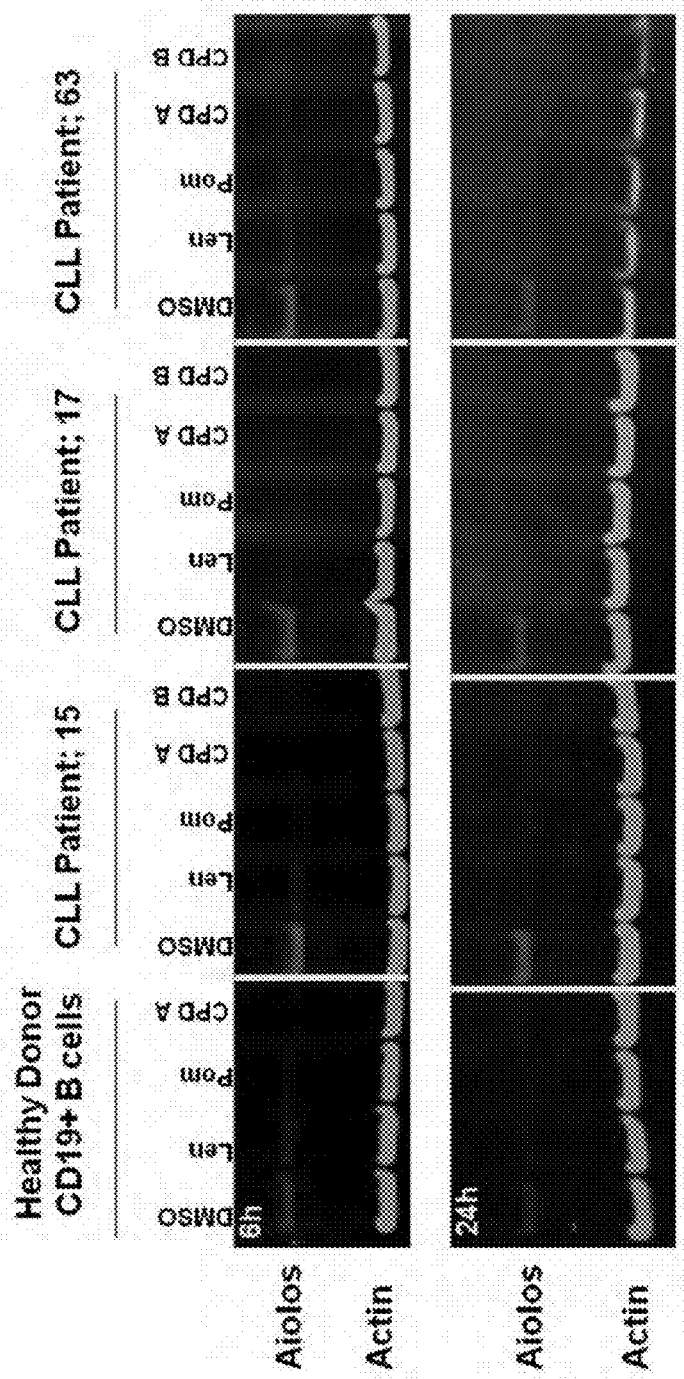

FIG. 22 shows that IMiDs affect Aiolos protein level in healthy donor B cells and CLL. Aiolos expression is higher in B-CLL cells than in B cells from healthy donors. IMids treatment inhibit Aiolos in B-CLL patient cells.

Figure 23:
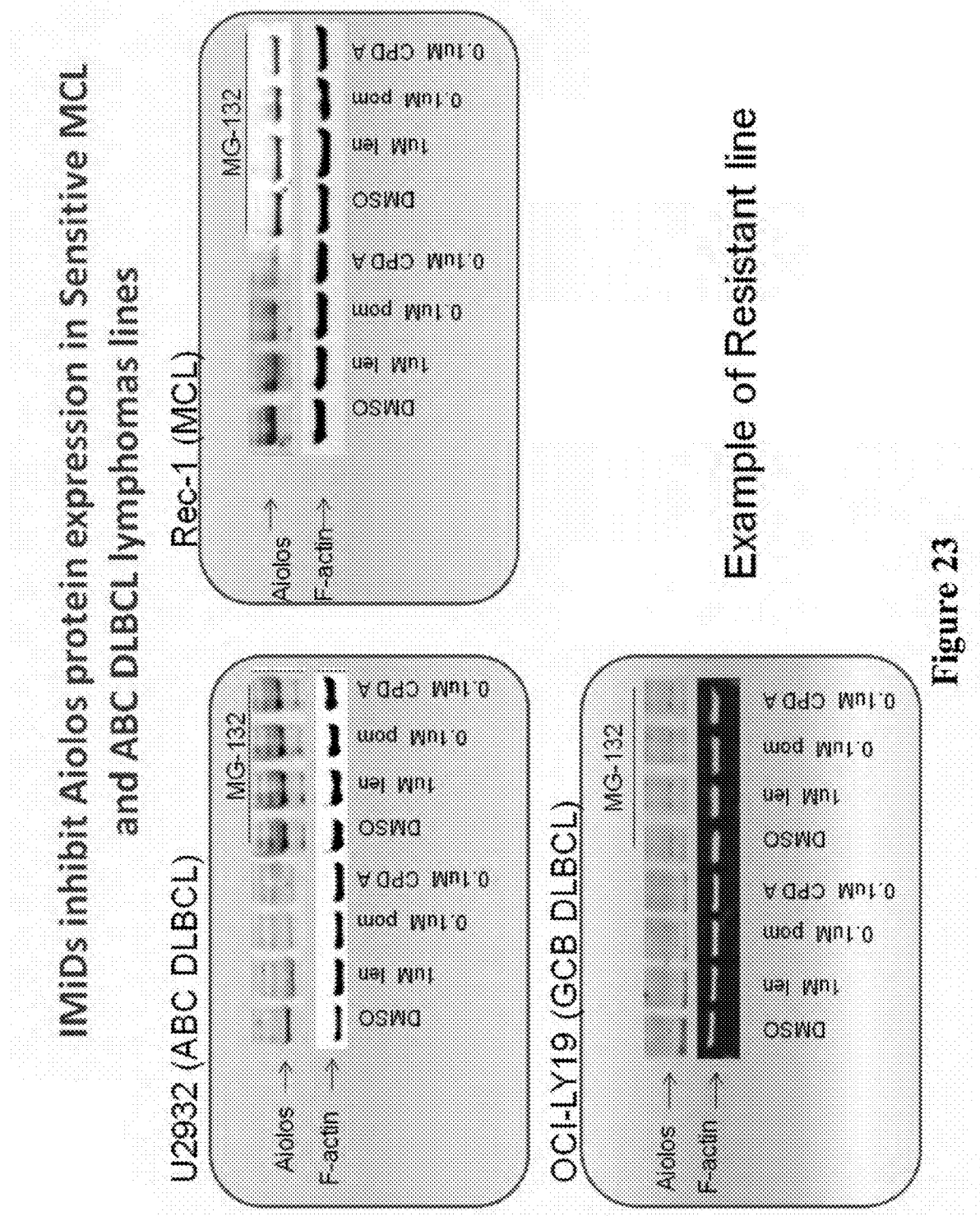

FIG. 23 shows that IMiDs inhibit Aiolos protein expression in MCL (Rec-1) and DLBCL lymphoma (U2932, OCI-LY19) cell lines.

Figure 24:
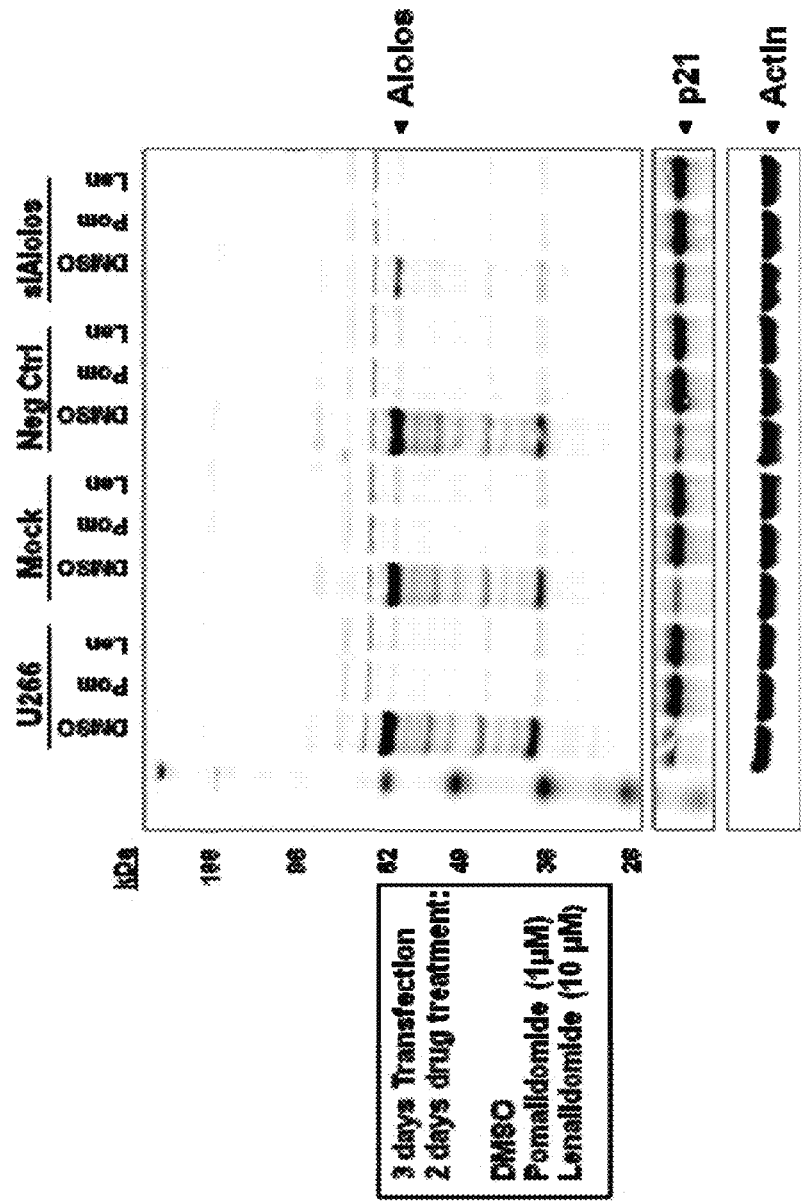

FIG. 24 shows that knockdown of Aiolos induces p21 expression.

Figure 25:
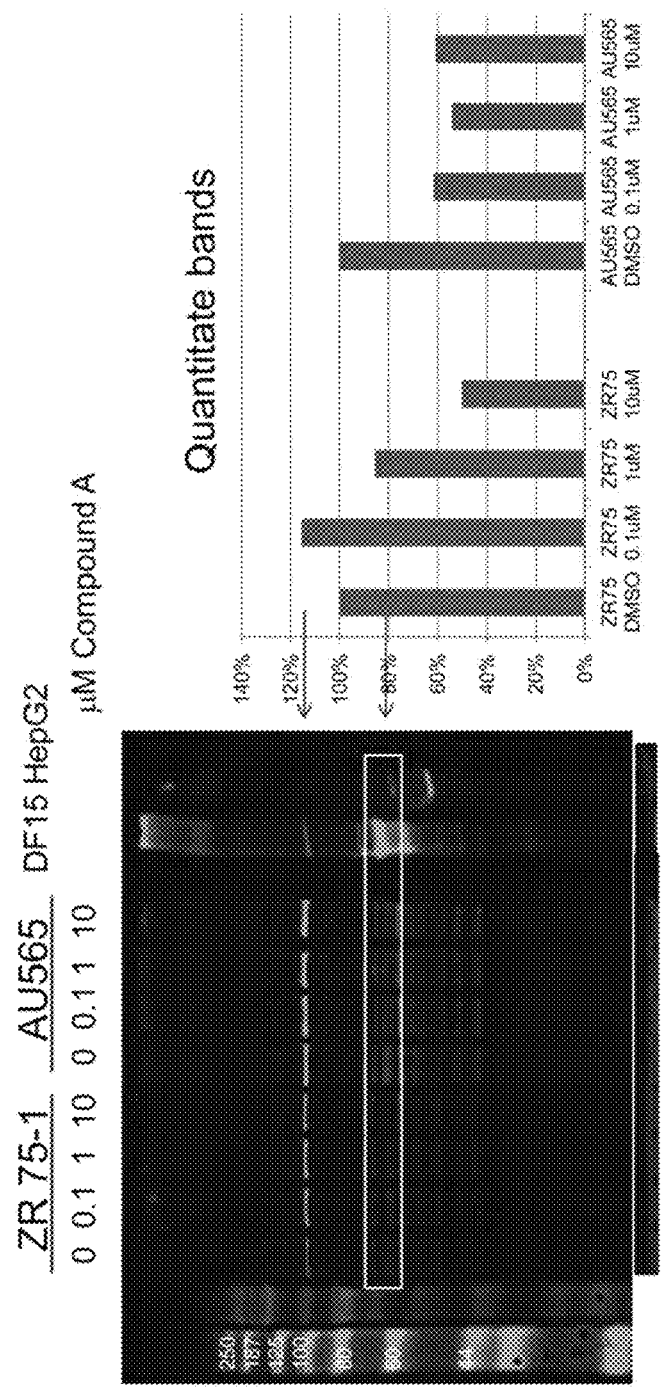

FIG. 25 shows the effect of Compound A on the levels of endogenous Aiolos in inflammatory breast cancer line AU565 and human carcinoma cell line ZR 75-1.

Figure 26:
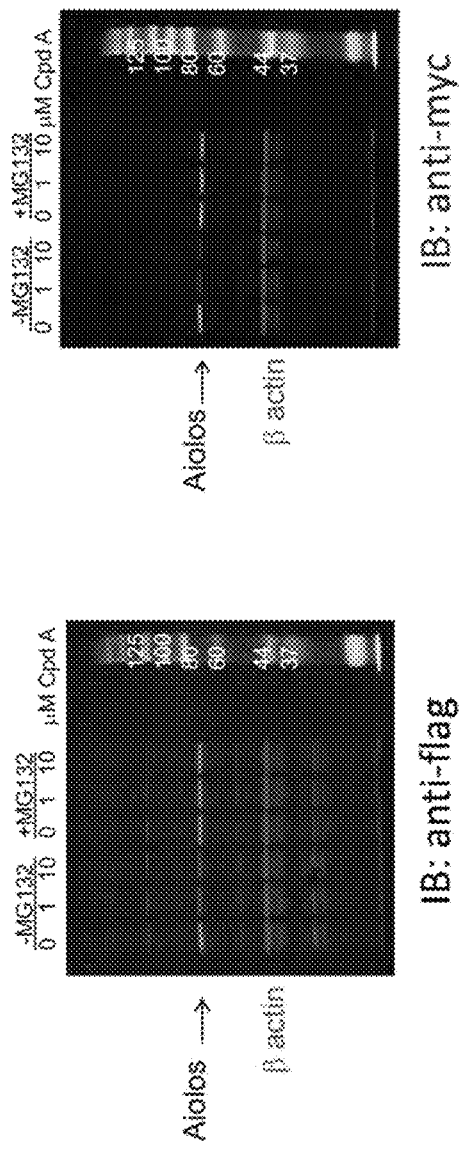

FIG. 26 shows effect of Compound A on the levels of Aiolos in AU565 cells and the patterns of detection using anti-flag and anti-myc antibodies.

Figure 27:
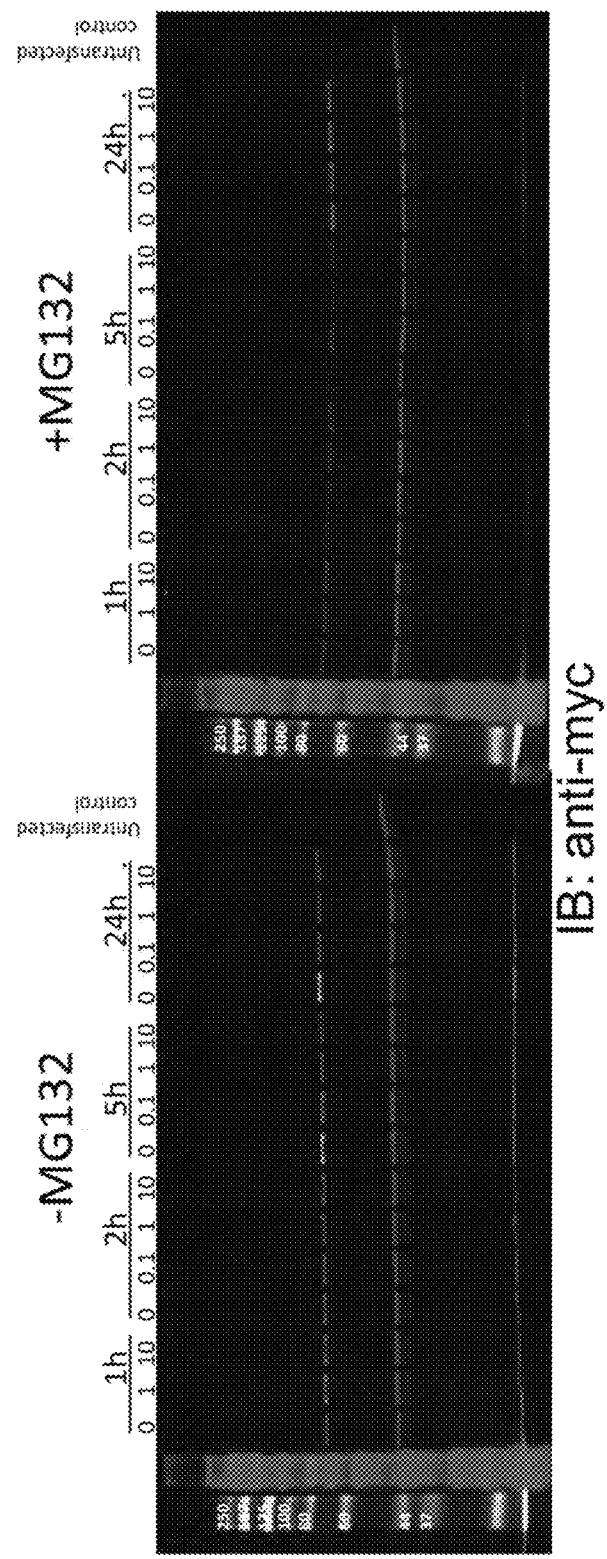

FIG. 27 show the time course of inhibition of Aiolos by Compound A and rescue of such inhibition by MF-132.

Figure 28:
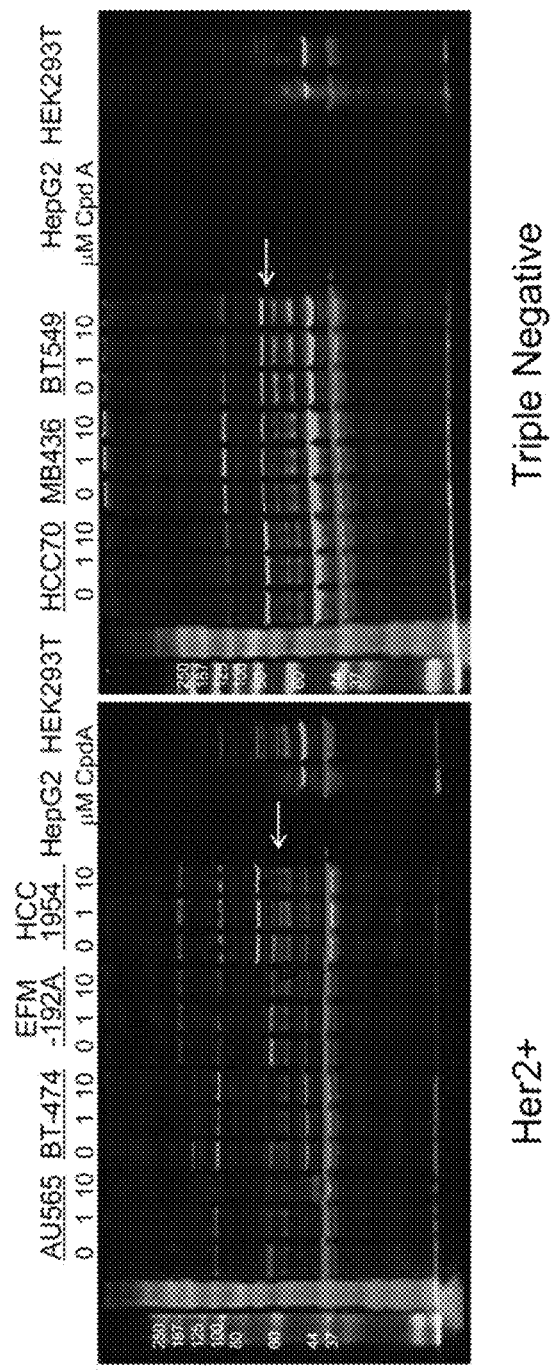

FIG. 28 shows the effect of Compound A on the levels of aiols in Her2+ cells in comparison with triple negative ("TN"; EP−/PR−/Her2−) cells.

Figure 29:
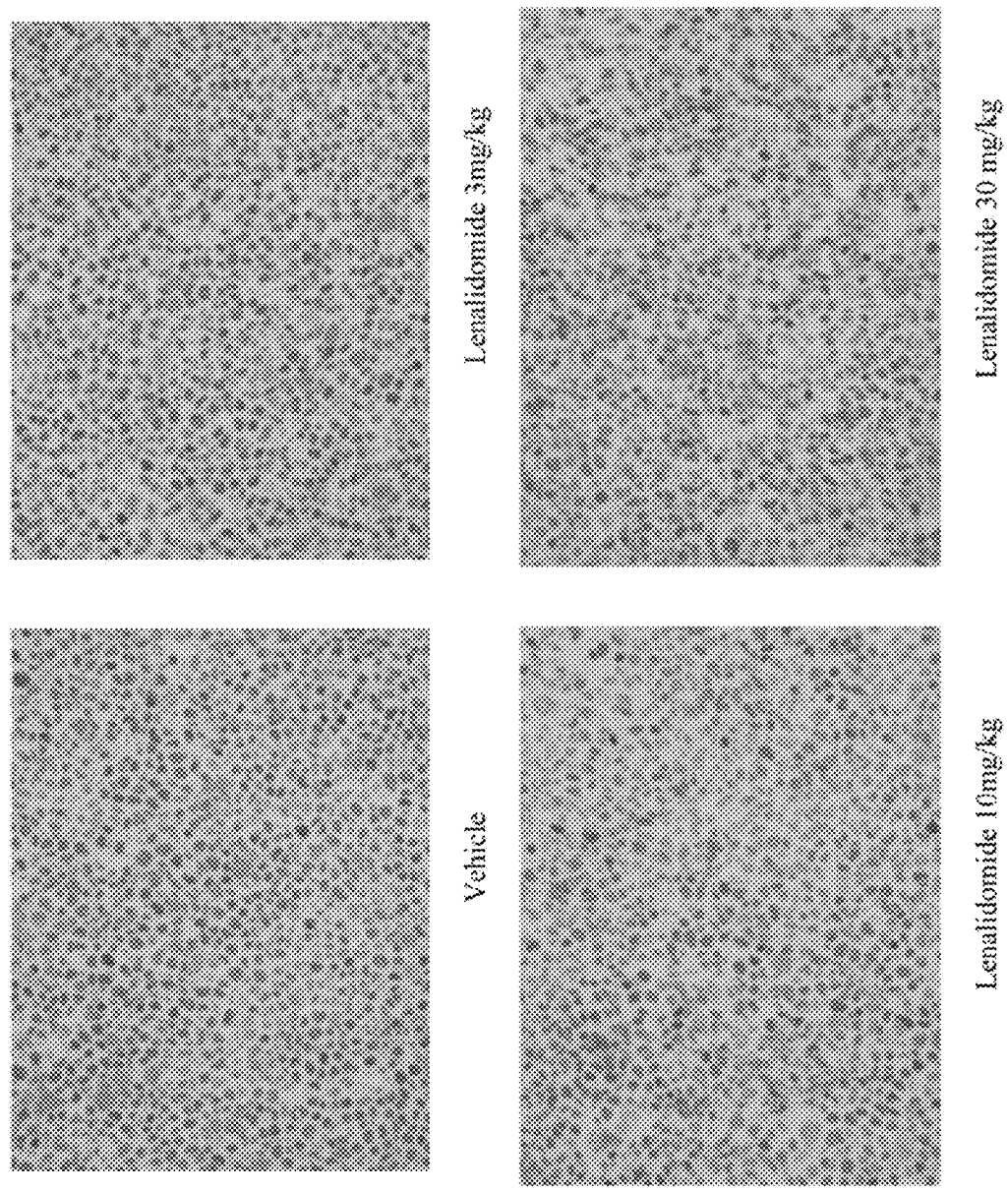

FIG. 29 shows the inhibition of Aiolos expression by lenalidomide in OCI-Ly10 xenograft lymphoma.

Figure 30:
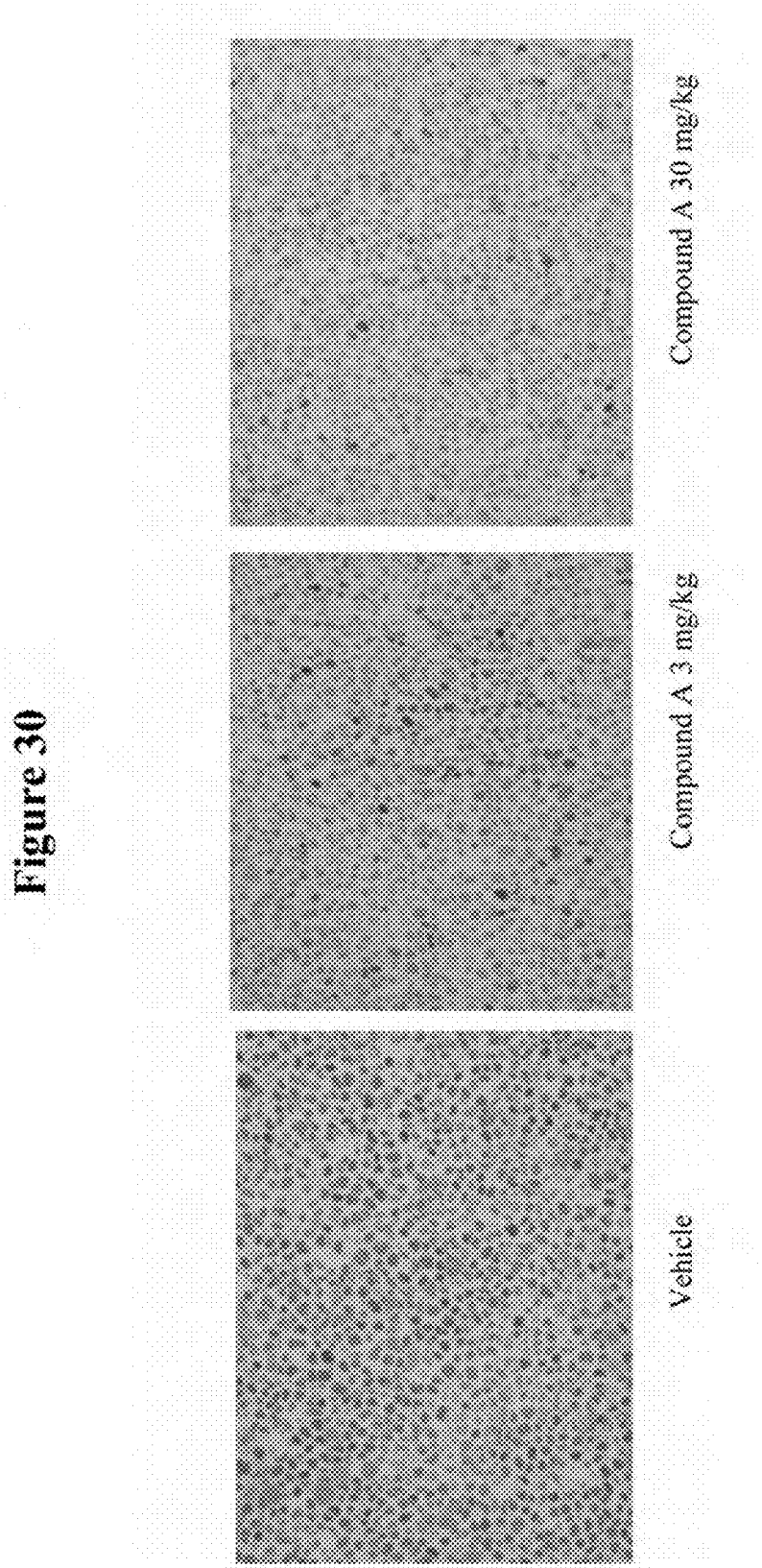

FIG. 30 shows the inhibition of Aiolos expression by Compound A in OCI-Ly10 xenograft lymphoma.

Figure 31:
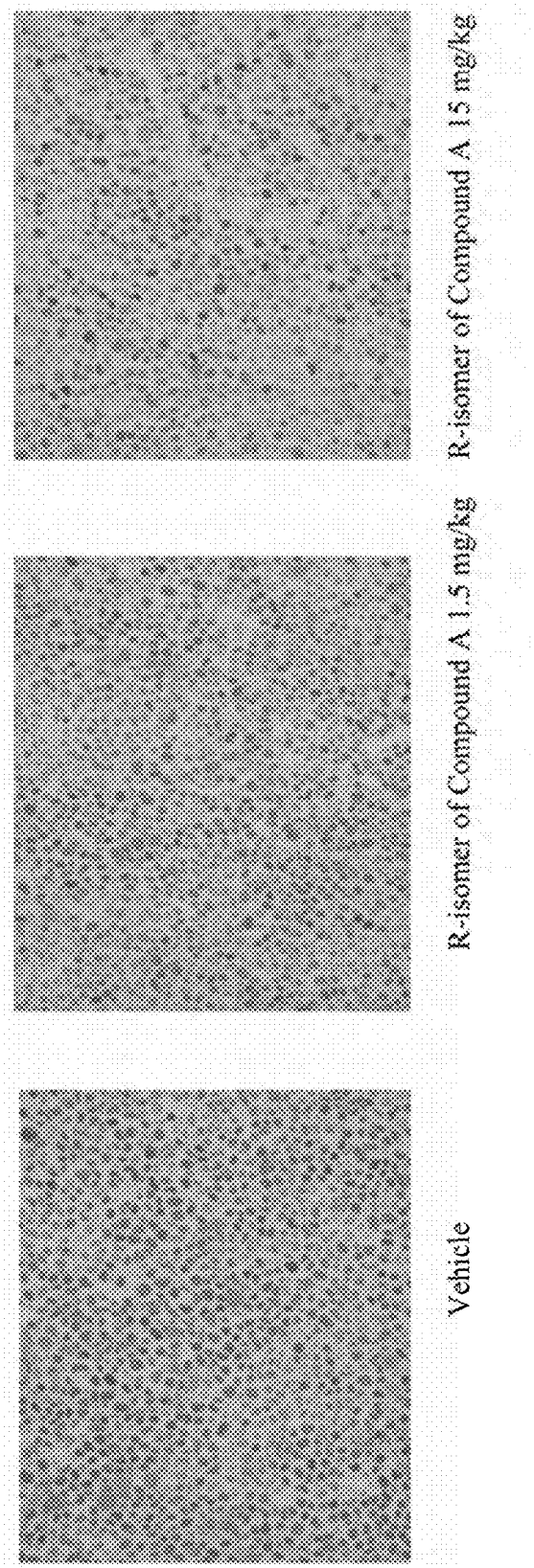

FIG. 31 shows the inhibition of Aiolos expression by R-isomer of Compound A in OCI-Ly10 xenograft lymphoma.

Figure 32:
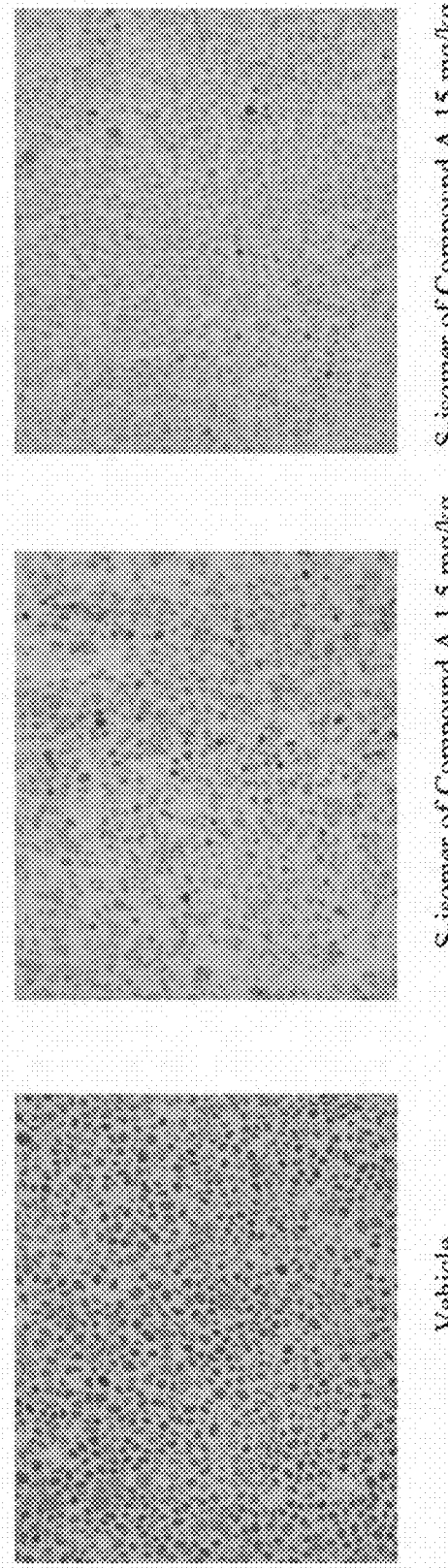

FIG. 32 shows the inhibition of Aiolos expression by S-isomer of Compound A in OCI-Ly10 xenograft lymphoma.

FIG. 33A shows FACS analysis results regarding the inhibition of Aiolos expression in lymphocytes at 1.5 hours after the treatment of whole blood with Compound A or Compound B.

Figure 33B:
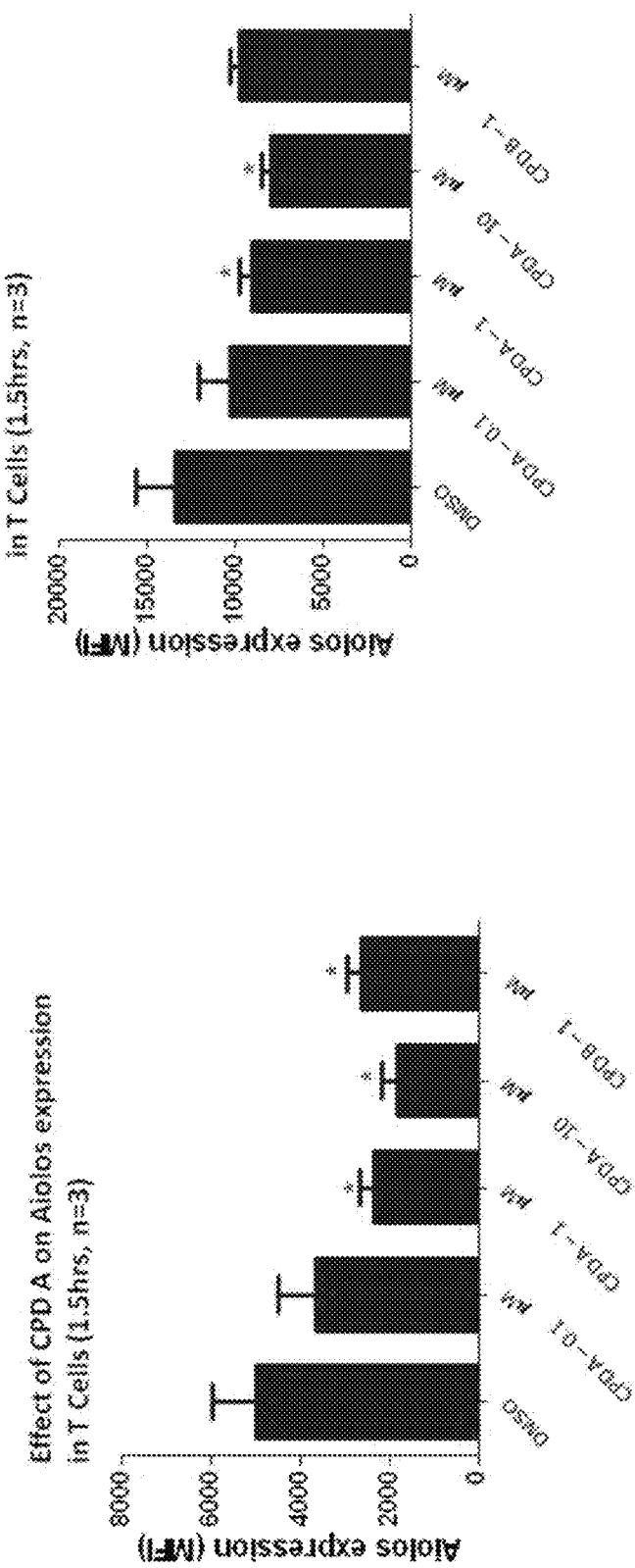

FIG. 33B shows the inhibition of Aiolos expression in T cells and B cells at 1.5 hours after the treatment of whole blood with Compound A or Compound B.

Figure 34A:
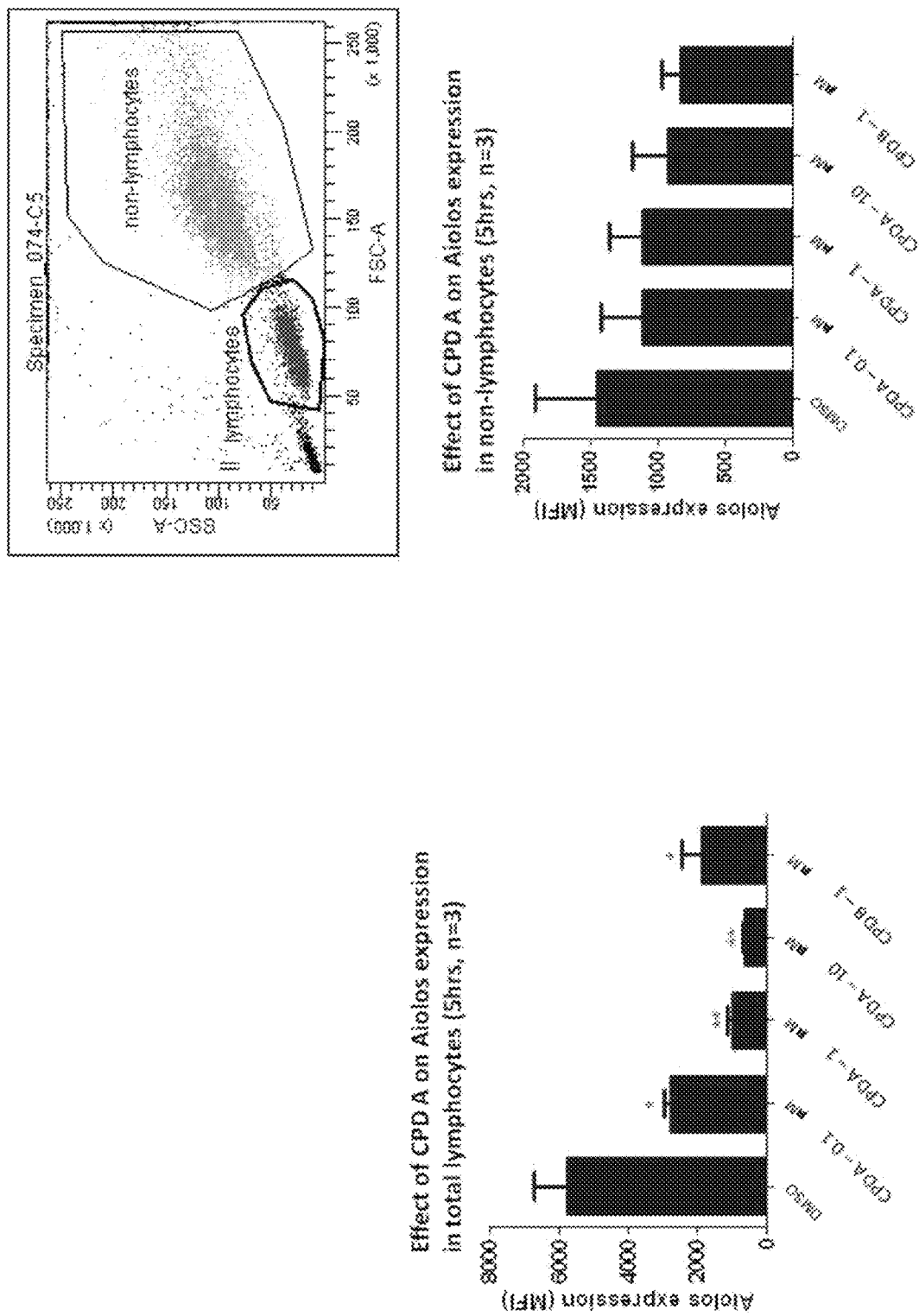

FIG. 34A shows FACS analysis results regarding the inhibition of Aiolos expression in lymphocytes at 5 hours after the treatment of whole blood with Compound A or Compound B.

FIG. 34 B shows the inhibition of Aiolos expression in T cells and B cells at 5 hours after the treatment of whole blood with Compound A or Compound B.

FIG. 35A shows FACS analysis results regarding the inhibition of Aiolos expression in viably frozen PMBCs prepared from whole blood at 1.5 hours after the treatment by Compound A or Compound B.

FIG. 35 B shows the inhibition of Aiolos expression in viably frozen T cells and B cells prepared from whole blood at 1.5 hours after the treatment by Compound A or Compound B.

FIG. 36 A shows FACS analysis results regarding the inhibition of Aiolos expression in viably frozen PMBCs prepared from whole blood at 5 hours after the treatment by Compound A or Compound B.

Figure 36B:
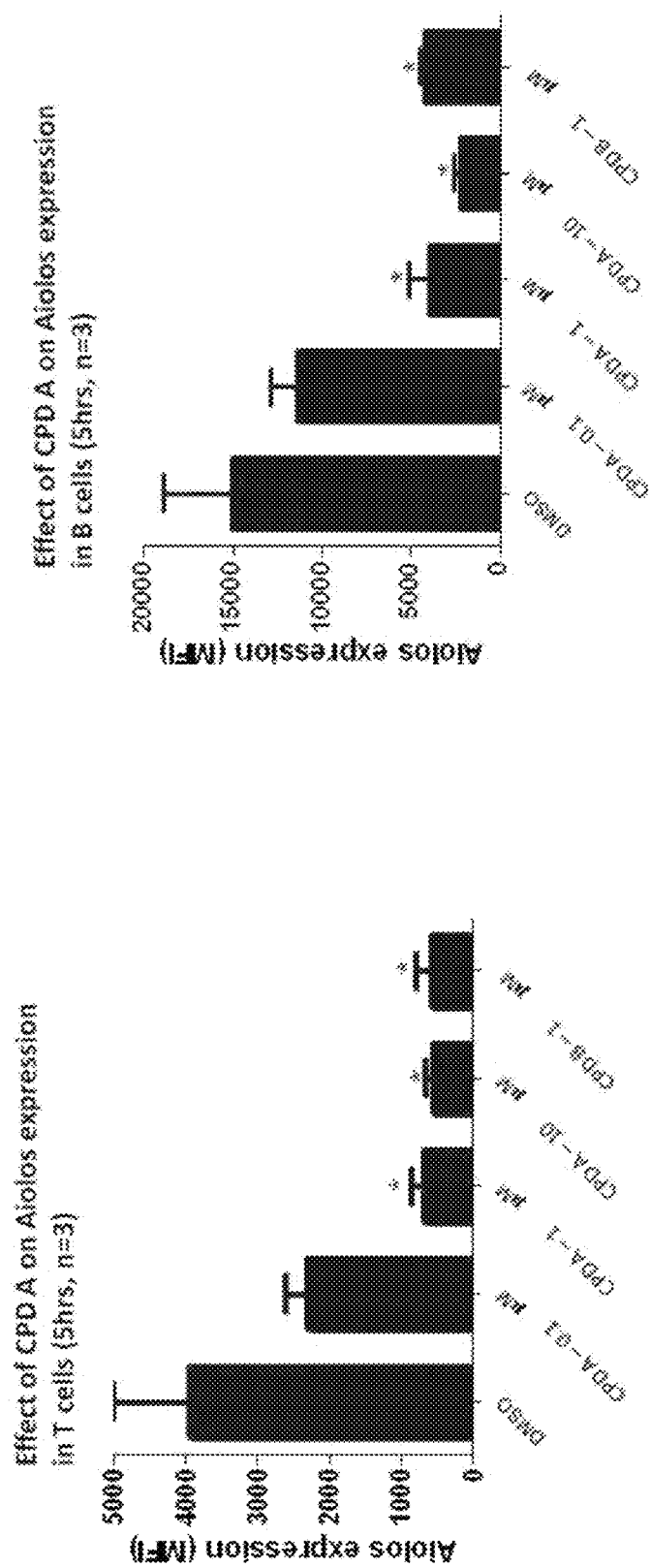

FIG. 36B shows the inhibition of Aiolos expression in viably frozen T cells and B cells prepared from whole blood at 5 hours after the treatment by Compound A or Compound B.

Figure 37:
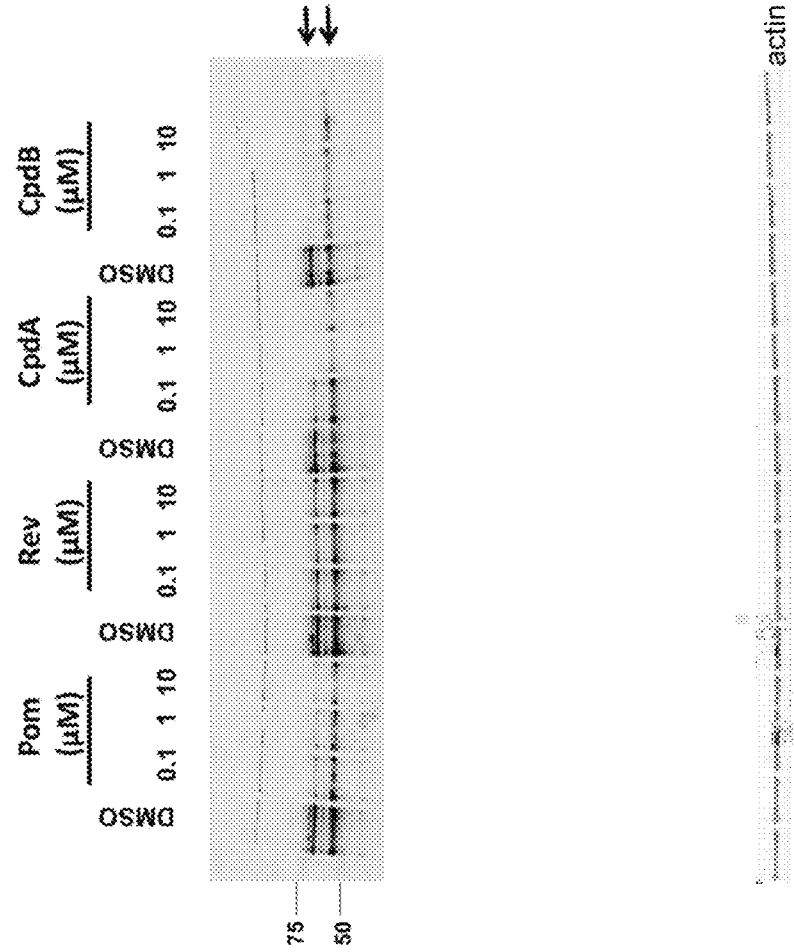

FIG. 37 shows the inhibition of Aiolos and Ikaros expression at 6 hours after the treatment with pomalidomide, lenalidomide, Compound A and Compound B.

Figure 38:

FIG. 38 shows enhancement of the detection of Aiolos peptide containing lysine 203 by lenalidomide and pomalidomide in multiple myeloma cells.

Figure 39:
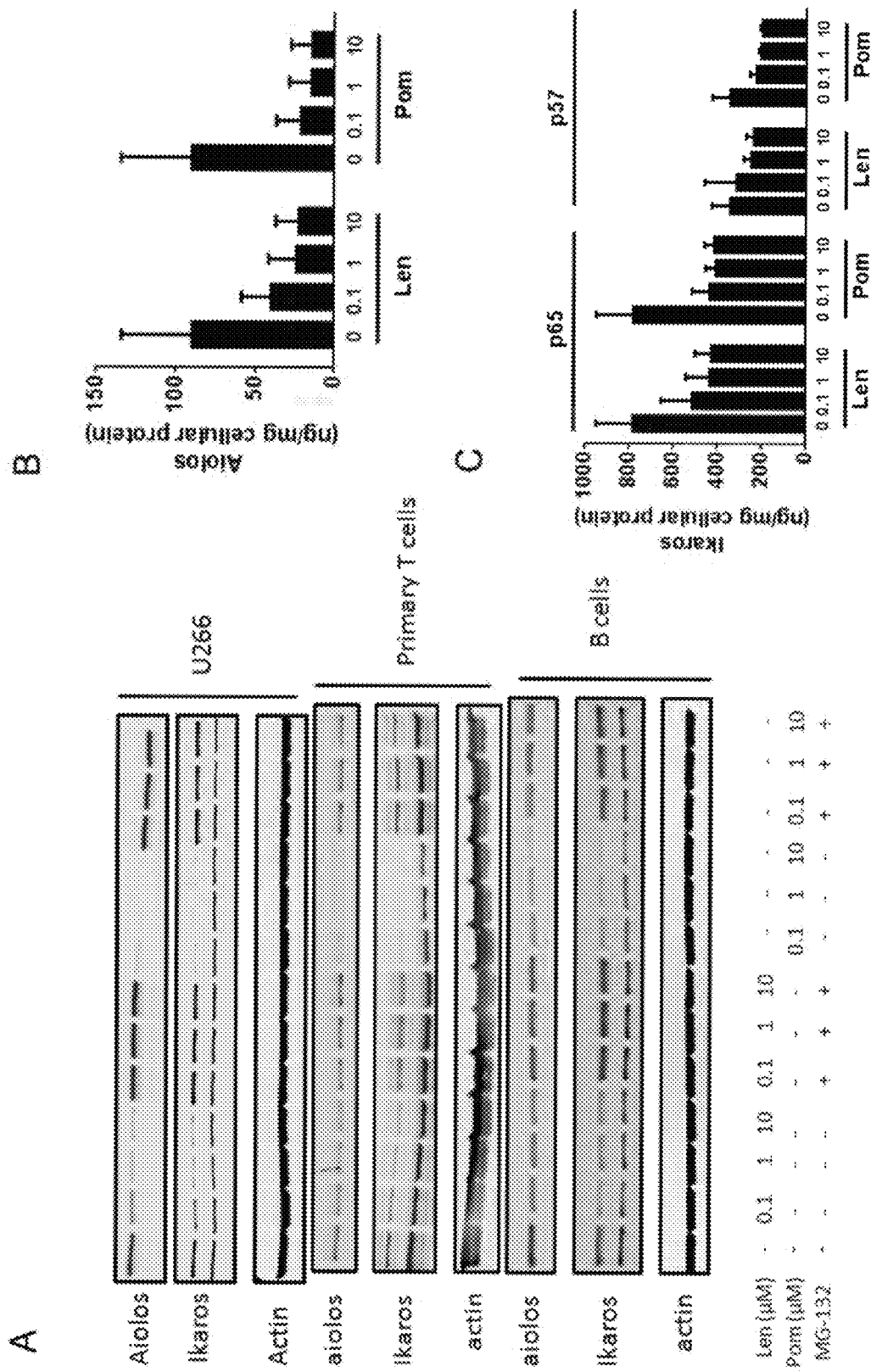

FIG. 39 A shows degradation of Aiolos and Ikaros by lenalidomide and pomalidomide in multiple myeloma cells, T cells, and B cells in a concentration and proteasome-dependent manner.

FIG. 39 B shows degradation of Aiolos by lenalidomide and pomalidomide in multiple myeloma cells in a concentration-dependent manner.

FIG. 39 C shows degradation of Ikaros by lenalidomide and pomalidomide in multiple myeloma cells in a concentration and proteasome-dependent manner.

Figure 40:
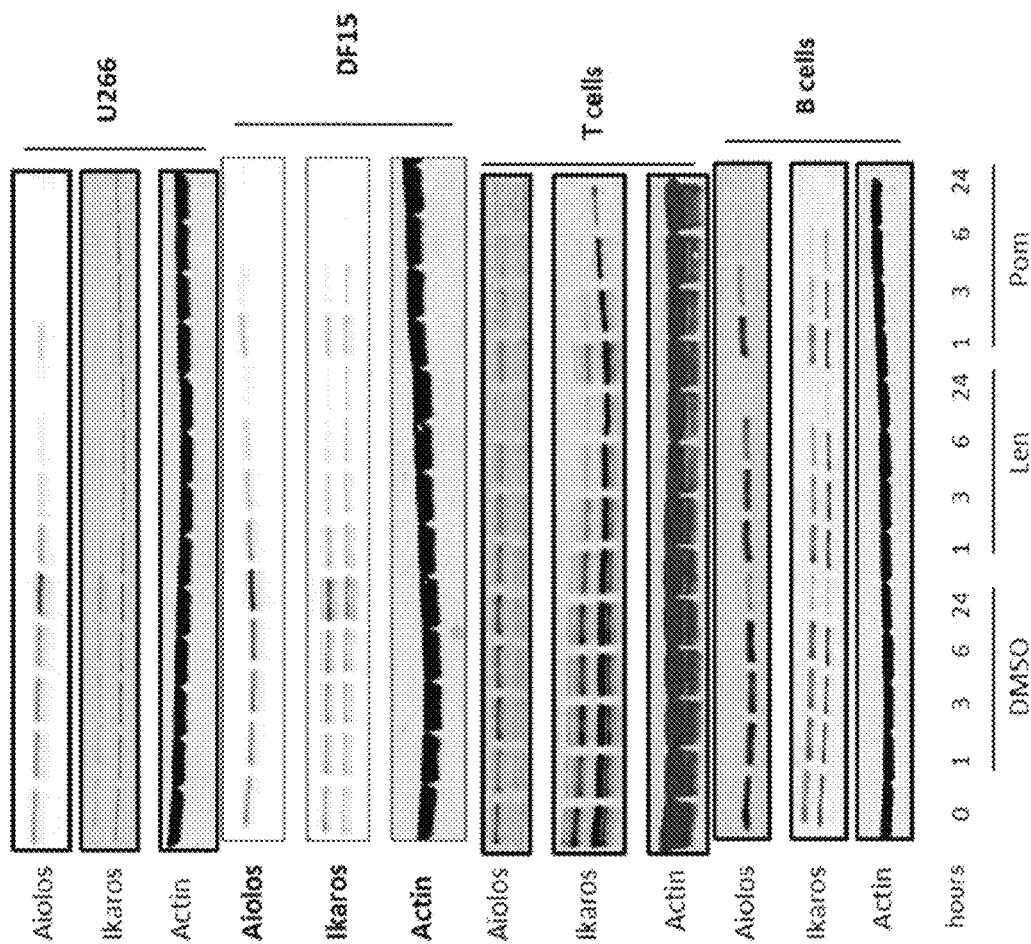

FIG. 40 shows that lenalidomide and pomalidomide destroy Aiolos and Ikaros within hours of drug treatment in MM cell, T cells, and B cells in a time-dependent manner.

Figure 41:
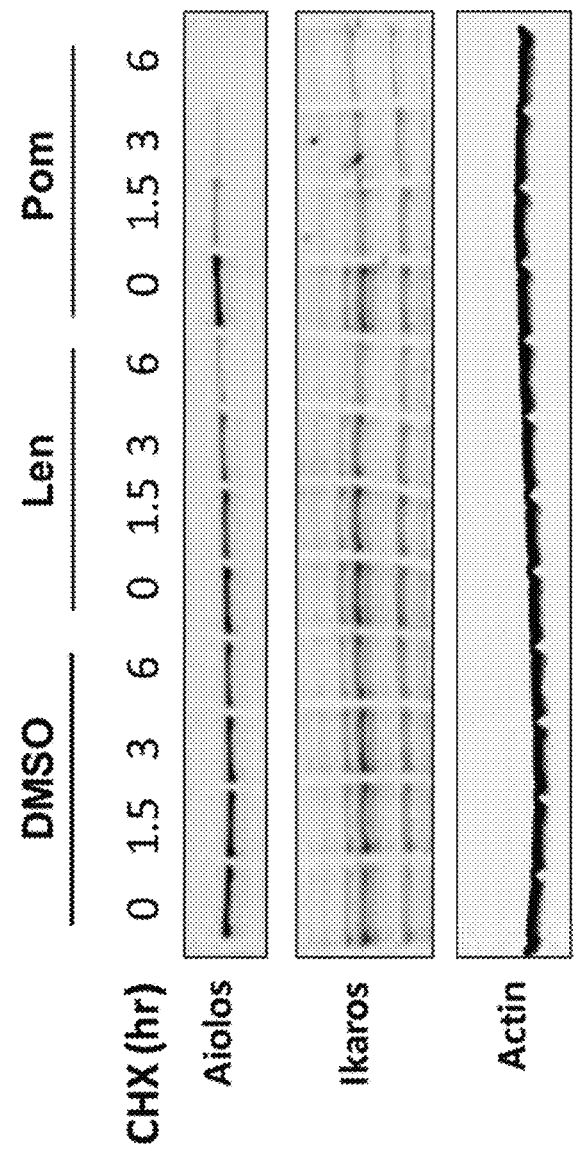

FIG. 41 shows that lenalidomide and pomalidomide induces the destruction of Aiolos in the presence of cycloheximide, and inhibitor of protein synthesis.

Figure 42:
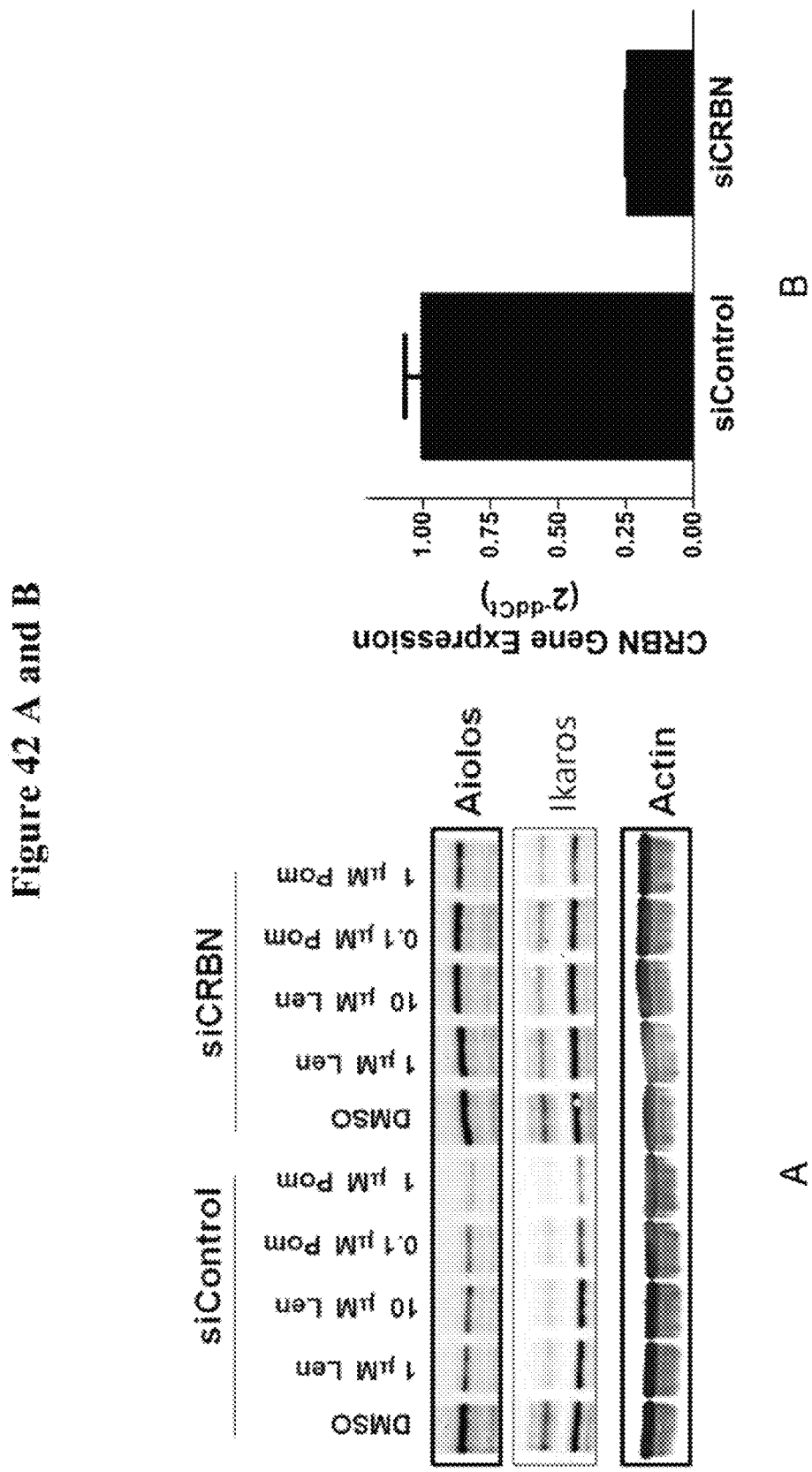

FIG. 42 A shows that Aiolos and Ikaros degradation by lenalidomide and pomalidomide is CRBN-dependent.

FIG. 42 B shows that siCRBN reduces CRBN gene expression.

Figure 43:
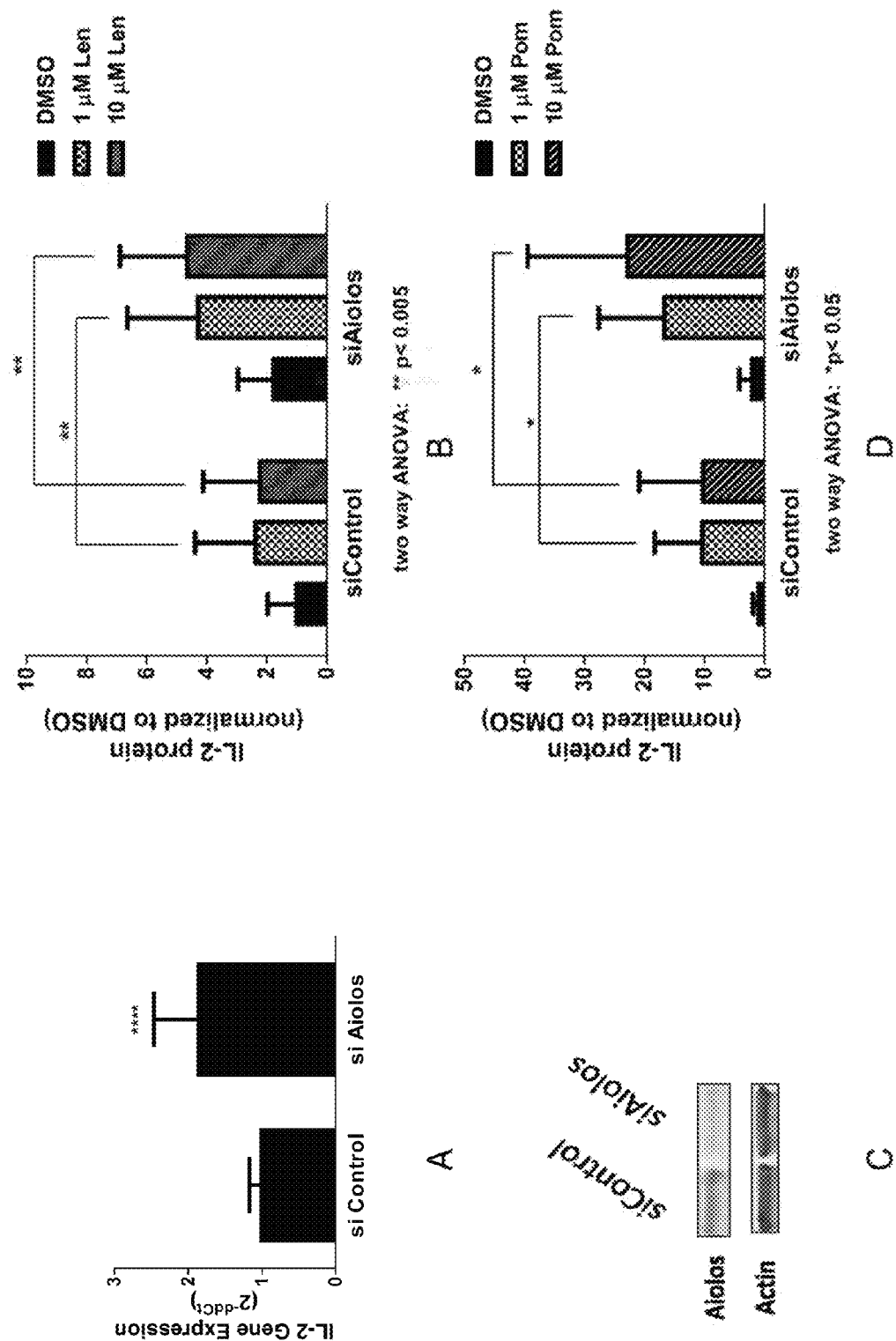

FIG. 43 A shows that Aiolos is a negative regulator of IL-2 in T cells.

FIG. 43 B shows that silencing Aiolos mimics lenalidomide treatment.

FIG. 43 C shows that siAiolos reduces Aiolos levels.

FIG. 43 D shows that silencing Aiolos mimics pomalidomide treatment.

FIG. 44A shows the anti-tumor activity of lenalidomide against H929 MM cells in mice.

FIG. 44B shows lenalidomide induces Aiolos and Ikaros degradation in H929 MM cells in mice, as measured by immunohistochemistry.

FIG. 44C shows that the in vivo anti-tumor activity by lenalidomide correlates with Aiolos and Ikaros degradation.

Figure 45:
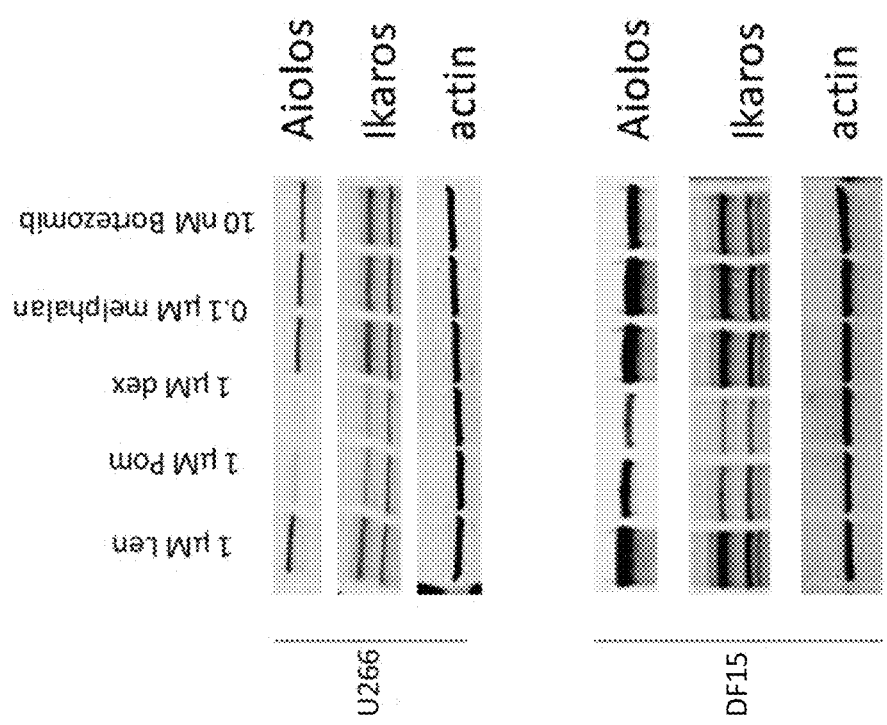

FIG. 45 shows that Aiolos and Ikaros degradation in multiple myeloma cells is unique to compounds provided herein.

Figure 46:
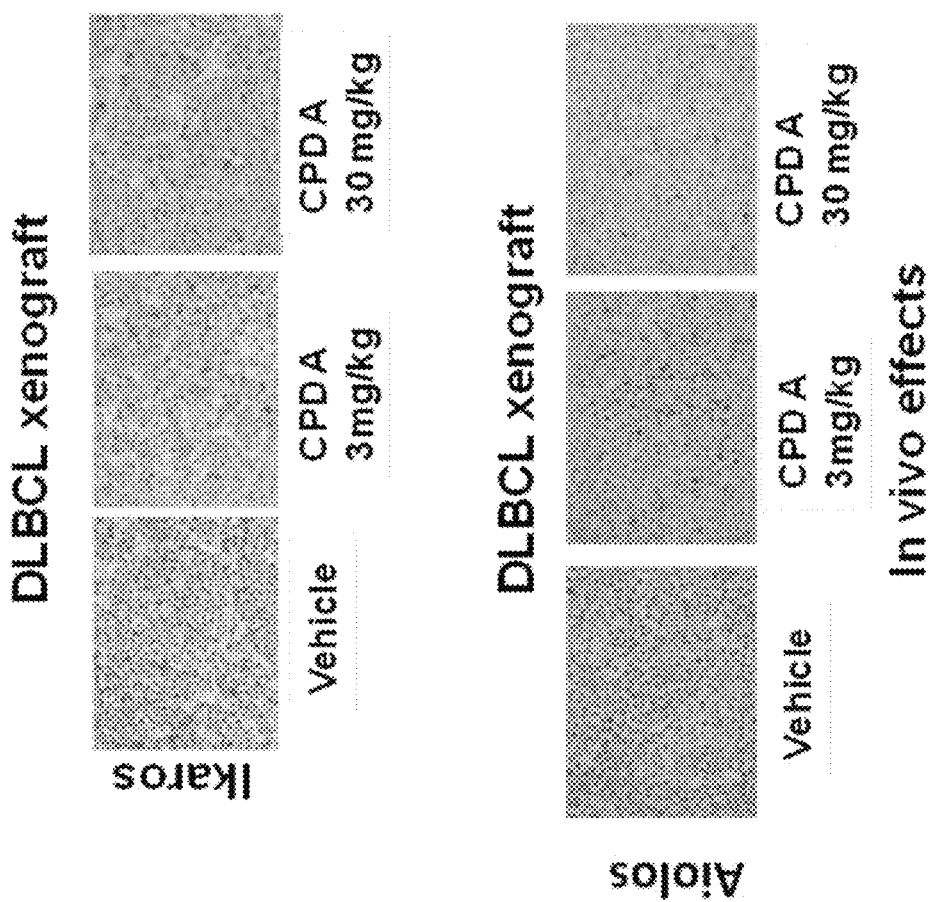

FIG. 46 shows the in vivo effects of Compound A on Ikaros and Aiolos in OCI-Ly10 lymphoma tumors in mice.

Figure 47:
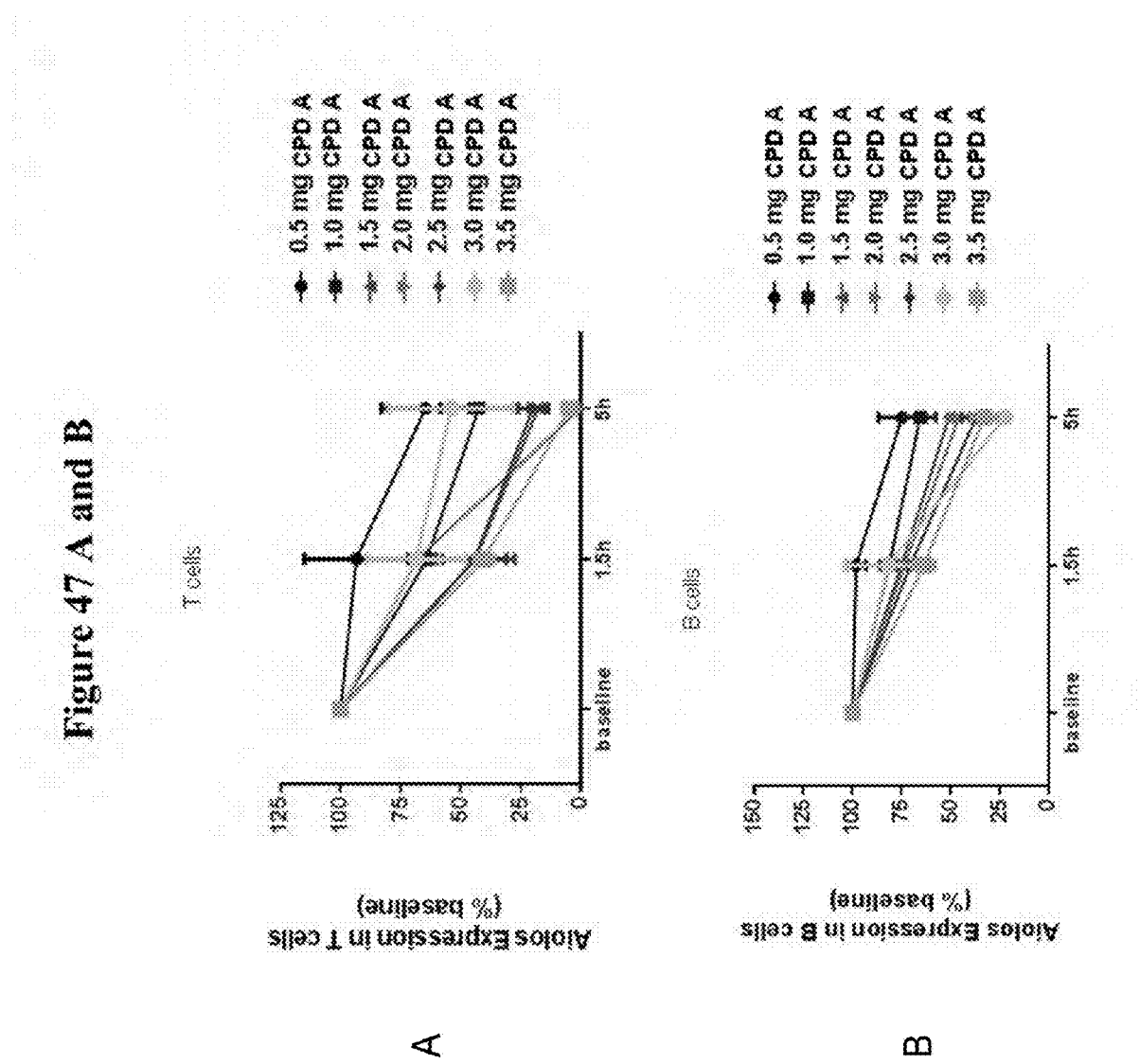

FIG. 47 A shows that Aiolos inhibition correlates with Compound A exposure in T cells by time and dose in cancer patients.

FIG. 47 B shows that Aiolos inhibition correlates with Compound A exposure in B cells by time and dose in cancer patients.

Figure 48:
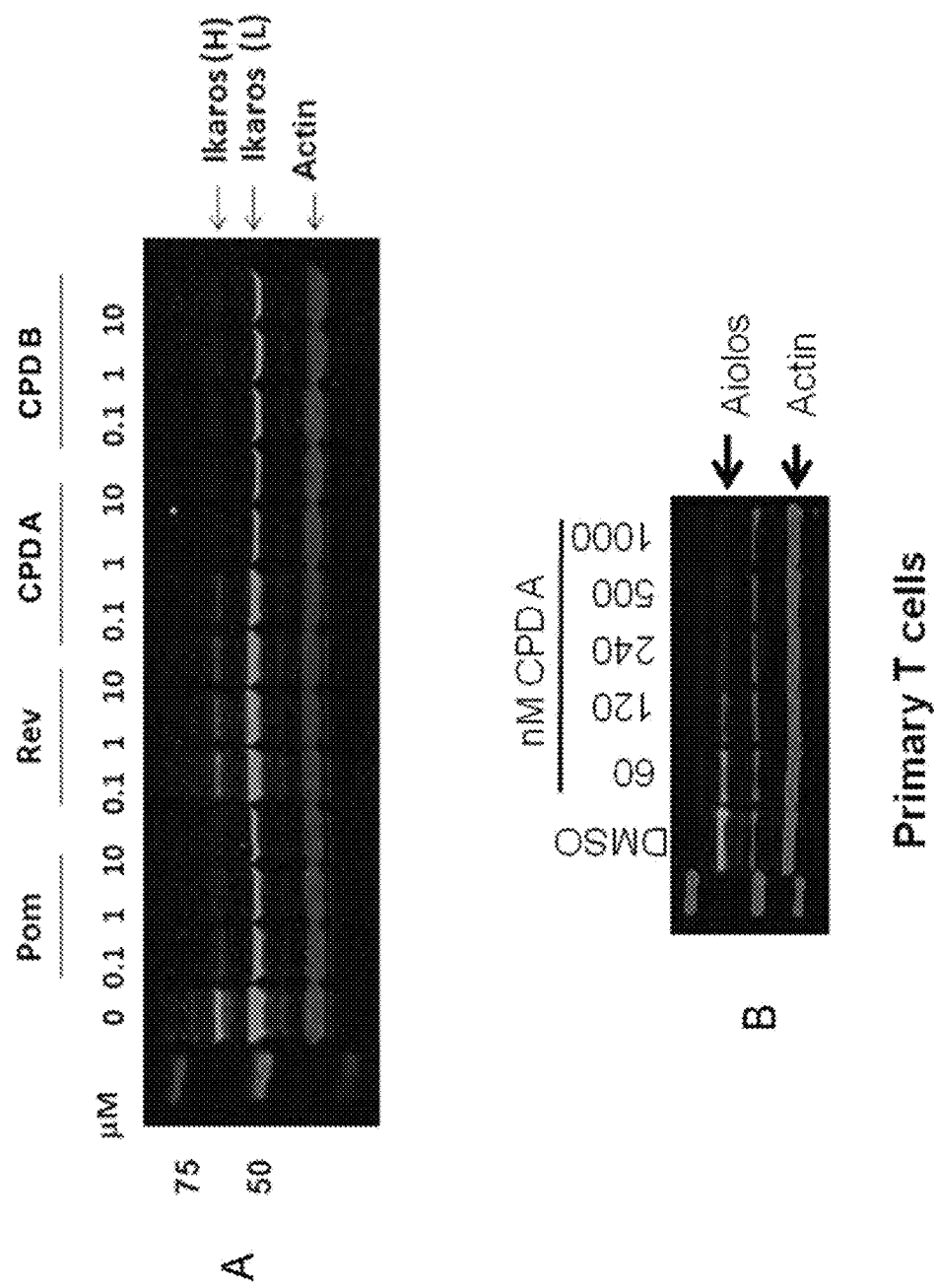

FIG. 48 A shows that immunomodulatory compounds affect the expression of Ikaros in T cells.

FIG. 48 B shows that Compound A affects the expression of Aiolos in T cells.

Figure 49:
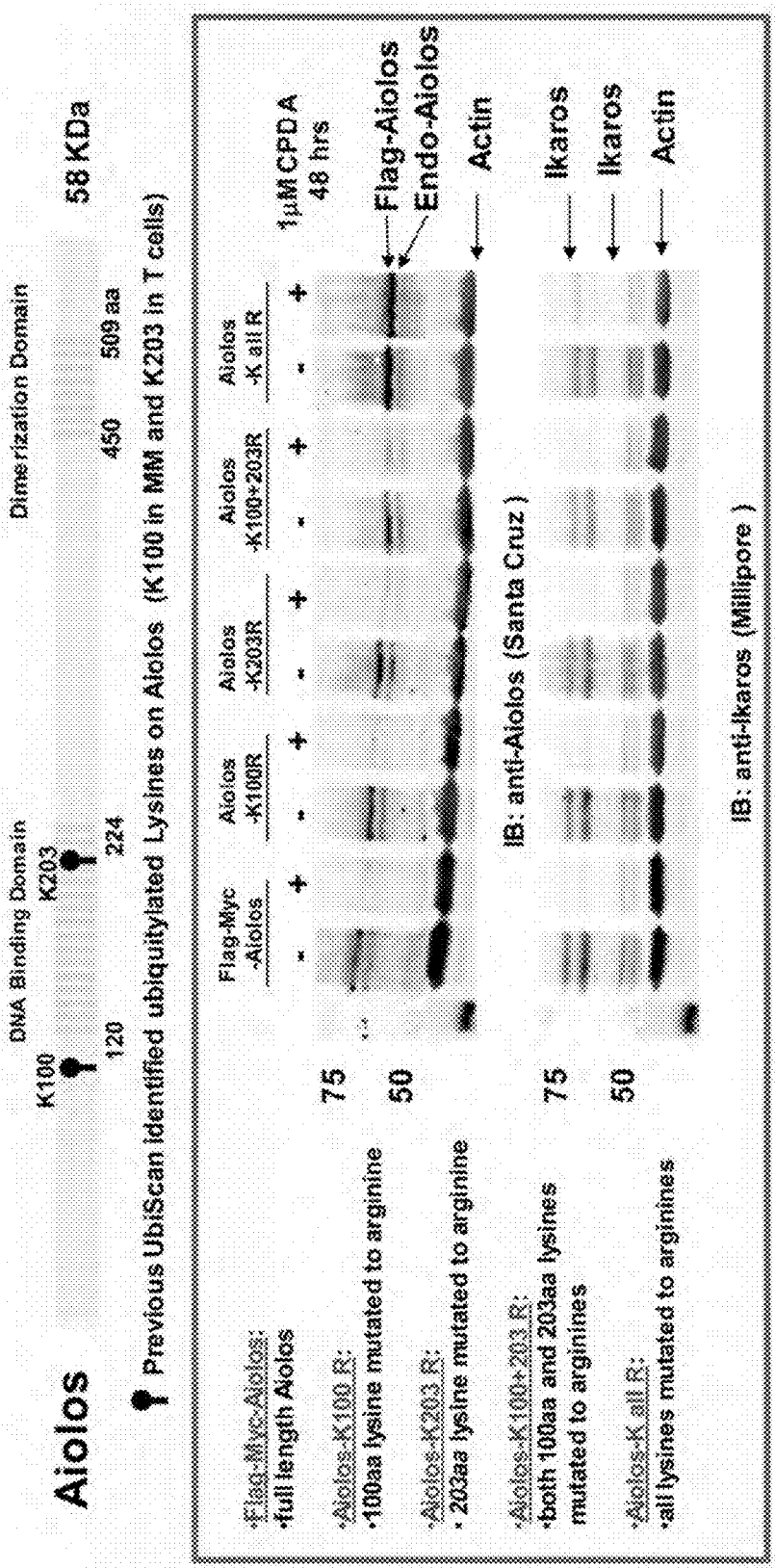

FIG. 49 shows that Compound A degrades both endogenous and over-expressed Aiolos in Jurkat cells; ubiquitination of multiple lysines are required for Compound A mediated Aiolos degradation, evidence that IMiD-induced Aiolos degradation is due to Aiolos ubiquitination; and Ikaros protein degradation by Compound A is Aiolos-independent in Jurkat cells.

Figure 50:
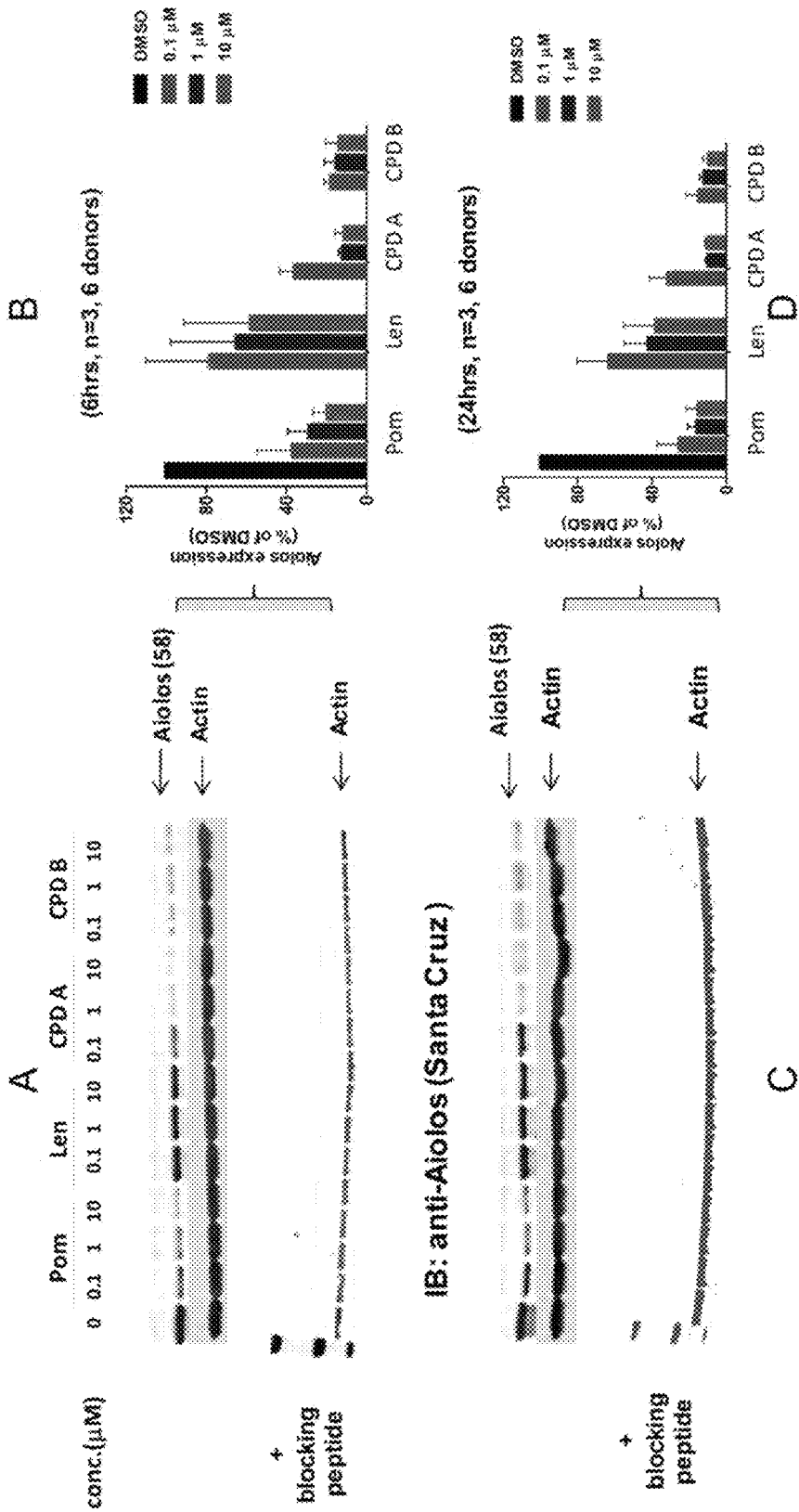

FIG. 50 A shows Aiolos Western blotting of primary human T cells. The gel shows a comparison of IMiD compounds on Aiolos degradation in primary T cells at 6 hours.

FIG. 50 B shows the quantification comparison of compounds provided herein on Aiolos degradation in primary T cells at 6 hours.

FIG. 50 C shows Aiolos Western blotting of primary human T cells. The gel shows a comparison of compounds provided herein on Aiolos degradation in primary T cells at 24 hours.

FIG. 50 D shows the quantification comparison of compounds provided herein on Aiolos degradation in primary T cells at 24 hours.

Figure 51:
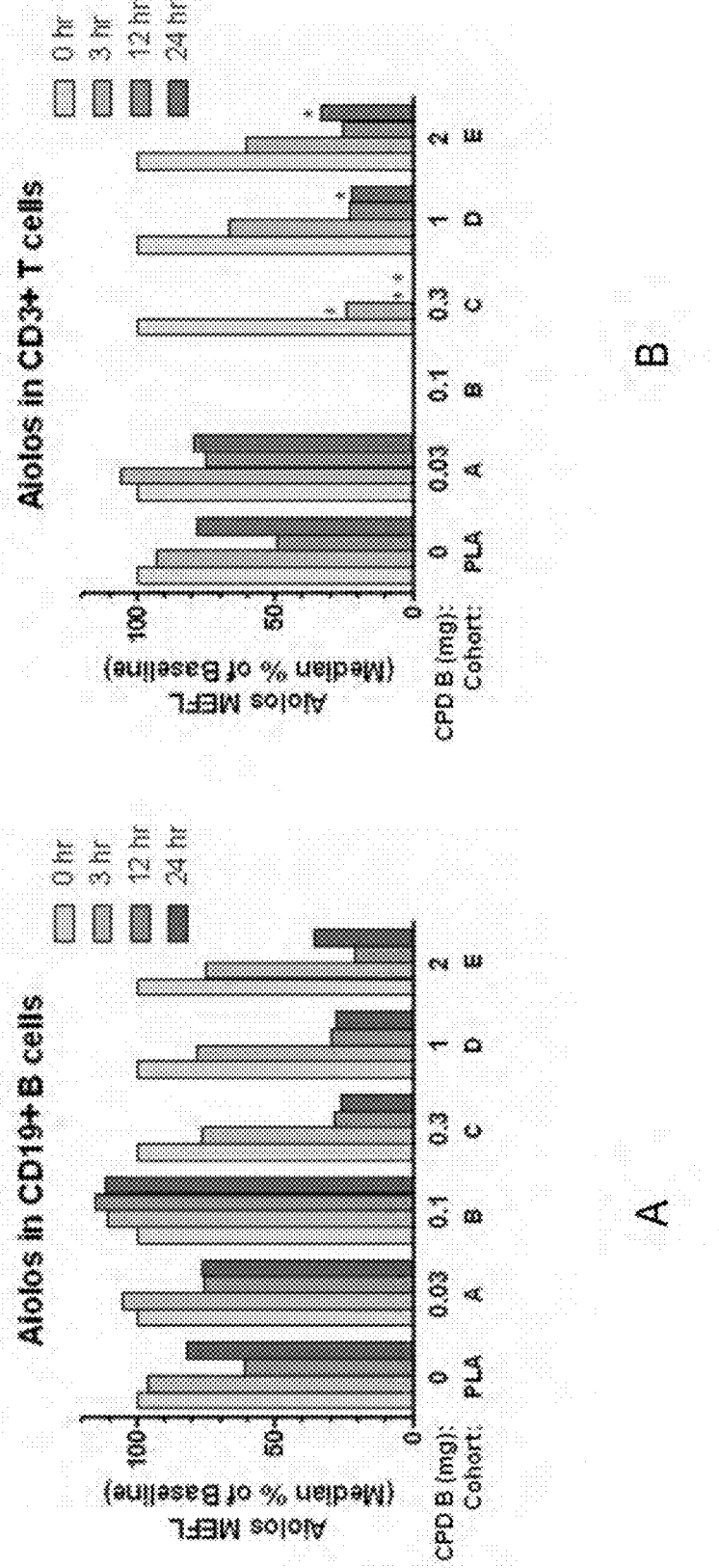

FIG. 51 A shows the reductions of Aiolos in B cells in response to various doses of Compound B in healthy volunteers.

FIG. 51 B shows the reductions of Aiolos in T cells in response to various doses of Compound B in healthy volunteers.

Figure 52:
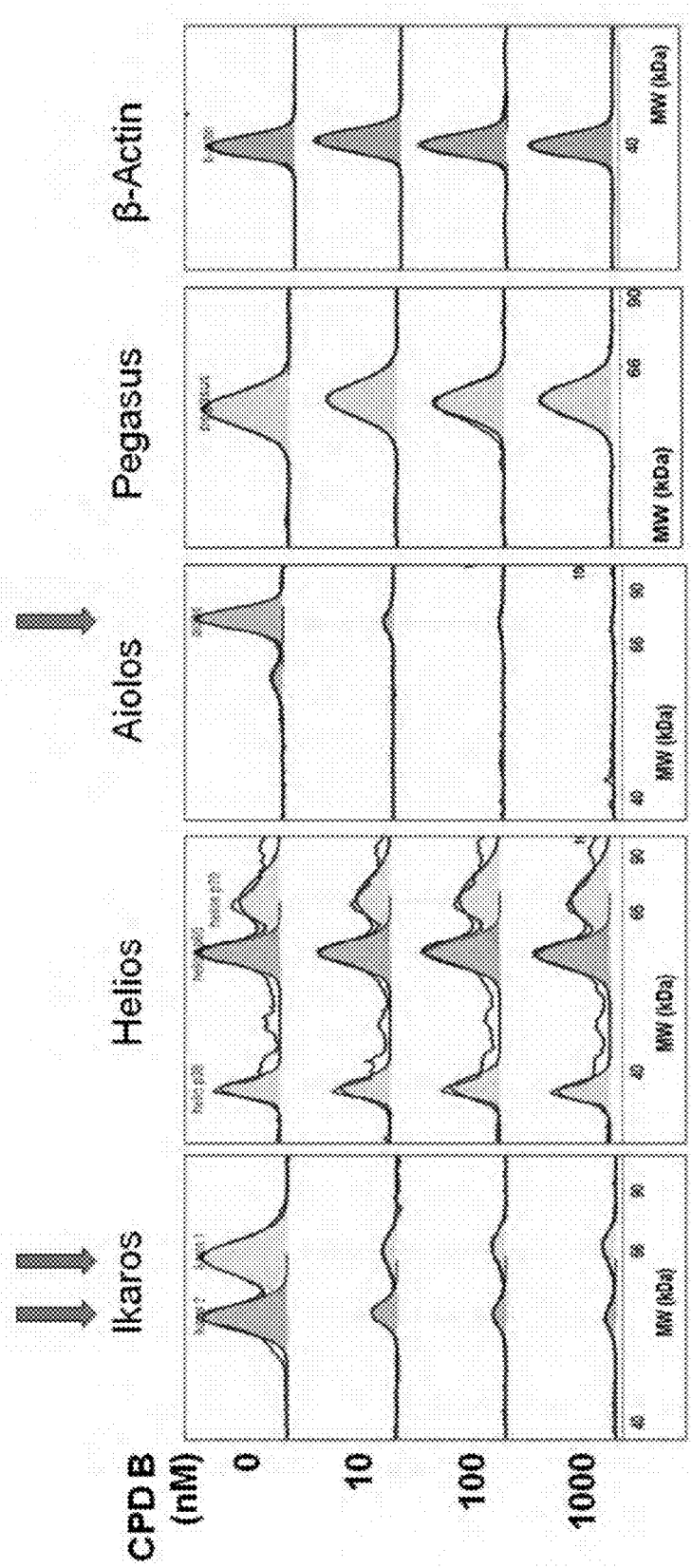

FIG. 52 shows that Compound B reduces Ikaros and Aiolos protein levels in B cells.

Figure 53:
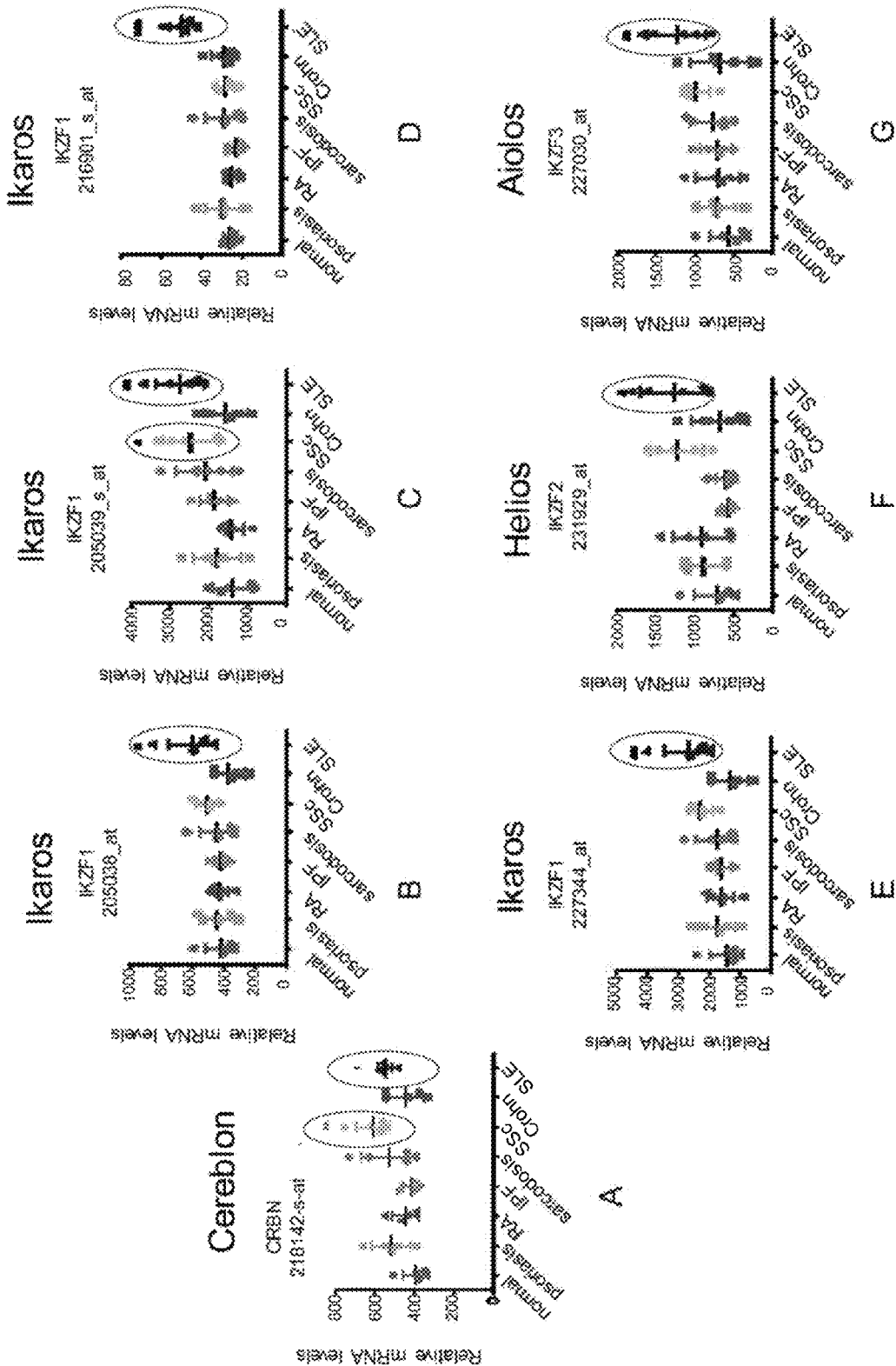

FIG. 53 A shows overexpression of Cereblon in SSc and SLE.

FIGS. 53 B-E show overexpression of Ikaros in SSc and SLE.

FIG. 53F shows overexpression of Helios in SSc and SLE.

FIG. 53G shows overexpression of Aiolos in SSc and SLE.

Figure 54:
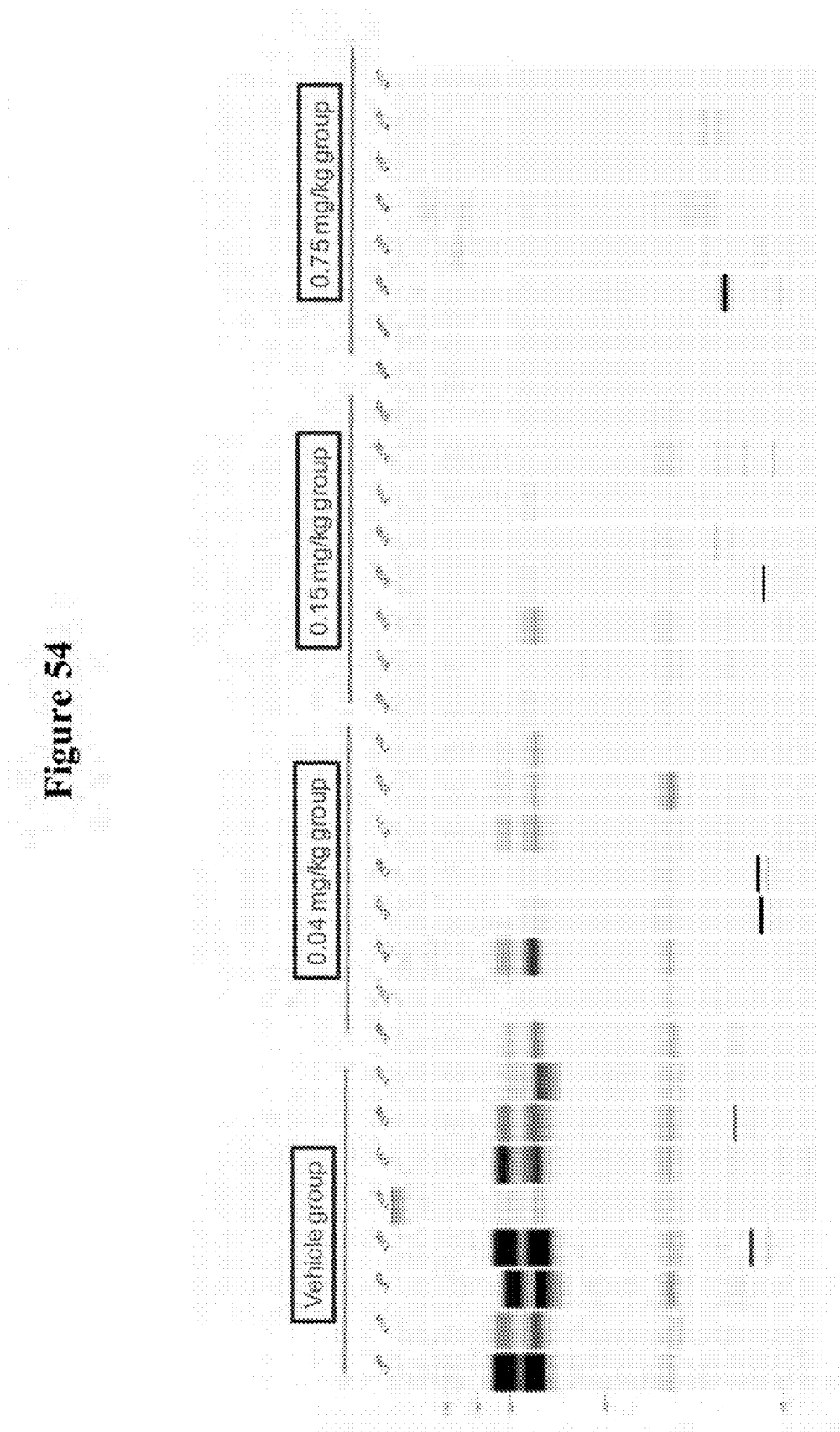

FIG. 54 shows Ikaros levels of PBMC samples from 32 monkeys treated with various doses of Compound B.

FIG. 55 A shows the effect of Compound B on Ikaros levels in PBMC of male and female monkeys.

FIG. 55 B shows the effect of Compound B on Ikaros levels in PBMC of female monkeys.

FIG. 55 C shows the effect of Compound B on Ikaros levels in PBMC of male monkeys.

Figure 56:
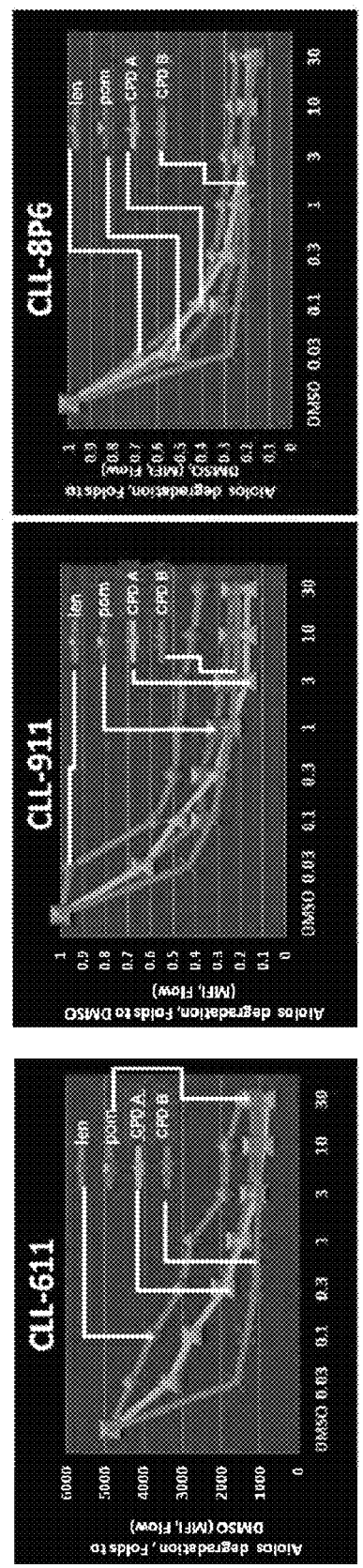

FIG. 56 A shows the effects of treatment by compounds provided herein using Western blot of key proliferation and survival proteins in CLL cells.

FIG. 56 B shows the effects of treatment by compounds provided herein through quantification of key proliferation and survival proteins in CLL cells.

FIG. 56 C shows dose-dependent inhibition of Aiolos by pomalidomide, lenalidomide, Compound A, and Compound B in three different B-CLL patient co-culture samples.

Figure 57:
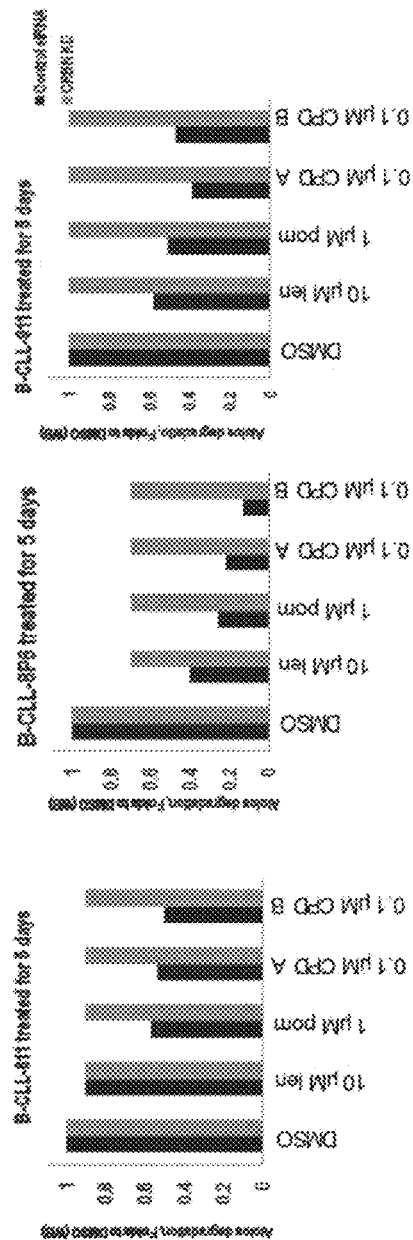
Figure 57:
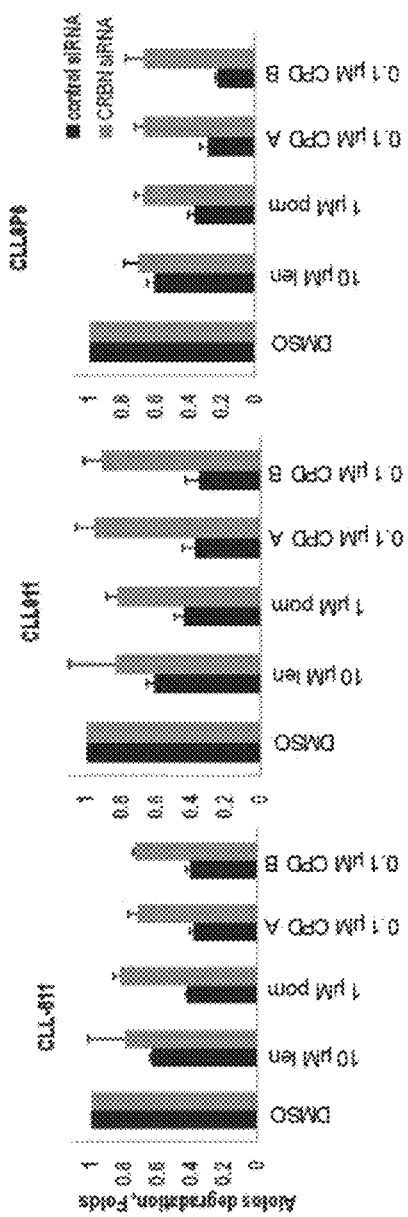
Figure 57:
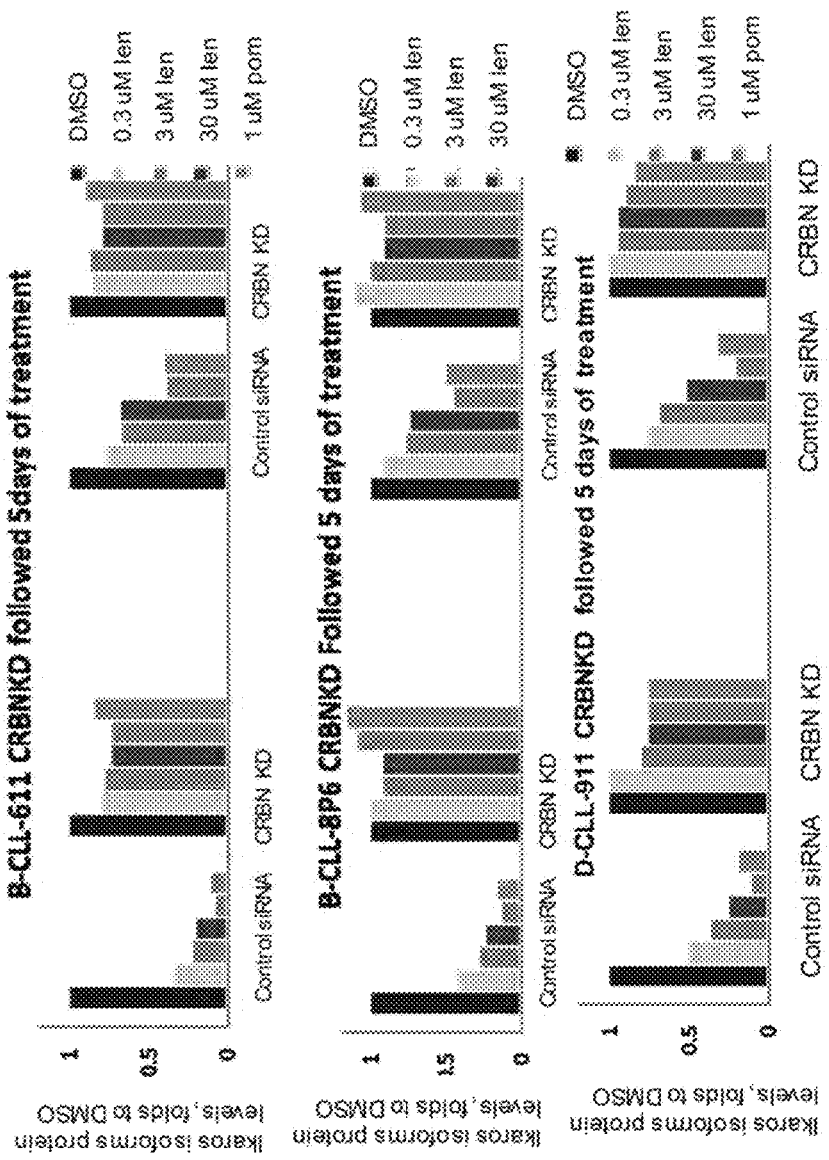

FIG. 57 A shows quantification of Aiolos in control and CRBN knockdown B-CLL cells treated with DMSO, pomalidomide, lenalidomide, Compound A or Compound B.

FIG. 57 B shows quantification of Flow cytometry measurement of Aiolos protein in control and CRBN knockdown B-CLL cells treated with DMSO, pomalidomide, lenalidomide, Compound A or Compound B.

FIG. 57 C shows quantification of Ikaros isoforms detected in control and CRBN knockdown B-CLL cells treated with DMSO, pomalidomide, lenalidomide, Compound A or Compound B.

6 DETAILED DESCRIPTION OF THE INVENTION

6.1 Definitions

As used herein, and unless otherwise specified, the terms "treat," "treating" and "treatment" refer to an action that occurs while a patient is suffering from the specified cancer, which reduces the severity of the cancer, or retards or slows the progression of the cancer.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

As used herein, the term "immunomodulatory compound" or "immunomodulatory drug" refers generally to a molecule or agent capable of altering the immune response in some way. Non-limiting examples of immunomodulatory compounds include those disclosed in Section 5.3 below.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent.

As used herein, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response" can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, the term "cereblon-associated protein" or "CRBN-associated protein" refers to a protein that interacts with or binds to CRBN directly or indirectly. In certain embodiments, a "cereblon-associated protein" or "CRBN-associated protein" is a substrate of CRBN, for example, a protein substrate of the E3 ubiquitin ligase complex involving CRBN, or the downstream substrates thereof. In one embodiment, the CRBN-associated protein provided herein is a substrate of CRBN such as IKZF3, also known as "Aiolos," of IKZF1, also known as "Ikaros." In certain embodiments, a "cereblon-associated protein" or "CRBN-associated protein" is a binding protein of CRBN.

The term "regulate" as used herein refers to controlling the activity of a molecule or biological function, such as enhancing or diminishing the activity or function.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors.

The term "refractory or resistant" refers to a circumstance where patients, even after intensive treatment, have residual cancer cells (e.g., leukemia or lymphoma cells) in their lymphatic system, blood and/or blood forming tissues (e.g., marrow).

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

The term "antibody" is used herein in the broadest sense and covers fully assembled antibodies, antibody fragments which retain the ability to specifically bind to the antigen (e.g., Fab, F(ab')2, Fv, and other fragments), single chain antibodies, diabodies, antibody chimeras, hybrid antibodies, bispecific antibodies, humanized antibodies, and the like. The term "antibody" covers both polyclonal and monoclonal antibodies. The term "antibody" and "immunoglobulin" or "Ig" may be used interchangeably herein. The terms "antibodies that immunospecifically bind to a CRBN antigen," "antibodies that immunospecifically bind to a CRBN epitope," "CRBN antibodies," "anti-CRBN antibodies" and analogous terms are also used interchangeably herein and refer to antibodies and fragments thereof, that specifically bind to a CRBN polypeptide, such as a CRBN antigen or epitope (e.g., peptide 65-76 human CRBN). The antibodies, including both modified antibodies (i.e., antibodies that comprise a modified IgG (e.g., IgG1) constant domain and unmodified antibodies (i.e., antibodies that do not comprise a modified IgG (e.g., IgG1) constant domain that specifically bind to a CRBN polypeptide. An antibody or a fragment thereof that immunospecifically binds to a CRBN antigen may be cross-reactive with related antigens. In certain embodiments, an antibody or a fragment thereof that immunospecifically binds to a CRBN antigen does not cross-react with other antigens. An antibody or a fragment thereof that immunospecifically binds to a CRBN antigen can be identified, for example, by immunoassays, BIAcore, or other techniques known to those of skill in the art. An antibody or a fragment thereof binds specifically to a CRBN antigen when it binds to a CRBN antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab") fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to a CRBN antigen (e.g., one or more complementarity determining regions (CDRs) of an anti-CRBN antibody). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In some embodiments, the anti-CRBN antibodies are fully human, such as fully human monoclonal CRBN antibodies. In certain embodiments, antibodies provided herein are IgG antibodies, or a class (e.g., human IgG1 or IgG4) or subclass thereof.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the CDR). The antigen binding region can be derived from any animal species, such as rodents (e.g., rabbit, rat or hamster) and humans. In some embodiments, the antigen binding region will be of human origin.

The term "constant region" or "constant domain" of an antibody refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

The term "epitope" as used herein refers to a localized region on the surface of an antigen, such as CRBN polypeptide or CRBN polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits a antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen.

The terms "fully human antibody" or "human antibody" are used interchangeably herein and refer to an antibody that comprises a human variable region and, in some embodiments, a human constant region. In specific embodiments, the terms refer to an antibody that comprises a variable region and constant region of human origin. "Fully human" anti-CRBN antibodies, in certain embodiments, can also encompass antibodies which bind CRBN polypeptides and are encoded by nucleic acid sequences which are naturally occurring somatic variants of human germline immunoglobulin nucleic acid sequence. In a specific embodiment, the anti-CRBN antibodies provided herein are fully human antibodies. The term "fully human antibody" includes antibodies having variable and constant regions corresponding to human germline immunoglobulin sequences as described by Kabat et al., Sequences of Proteins of Immunological Interest, Fifth Edition, U.S. Department of Health and Human Services, NIH Publication No. 91-3242, 1991. Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences. See Kabat, E. A. et al. (1991) Sequences of Proteins of Immunological Interest, Fifth Edition, U.S. Department of Health and Human Services, NIH Publication No. 91-3242. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. In some embodiments the heavy chain is a human heavy chain.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof. Kabat et al. (1971) *Ann. any Acad. Sci.* 190:382-391 and, Kabat et al. (1991) Sequences of Proteins of Immunological Interest, Fifth Edition, U.S. Department of Health and Human Services, NIH Publication No. 91-3242. For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3. Other numbering schemes will be readily understood by those skilled in the art.

The term "light chain" when used in reference to an antibody refers to two distinct types, called kappa (κ) of lambda (λ) based on the amino acid sequence of the constant domains. Light chain amino acid sequences are well known in the art. In certain embodiments, the light chain is a human light chain.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only a CRBN epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art. See, e.g., Chapter 11 in: Short Protocols in Molecular Biology, (2002) 5th Ed., Ausubel et al., eds., John Wiley and Sons, New York. Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art. See, e.g., Chapter 11 in: Short Protocols in Molecular Biology, (2002) 5th Ed., Ausubel et al., eds., John Wiley and Sons, New York.

The terms "cereblon" or "CRBN" and similar terms refers to the polypeptides ("polypeptides," "peptides" and "proteins" are used interchangeably herein) comprising the amino acid sequence any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and interspecies homologs, which, in certain embodiments, retain CRBN activity and/or are sufficient to generate an anti-CRBN immune response.

The term "CRBN antigen" refers to that portion of a CRBN polypeptide to which an antibody immunospecifically binds. A CRBN antigen also refers to an analog or derivative of a CRBN polypeptide or fragment thereof to which an antibody immunospecifically binds. A localized region on the surface of a CRBN antigen that is capable of eliciting an immune response is an CRBN "epitope." A region of a CRBN polypeptide contributing to an epitope may be contiguous amino acids of the polypeptide or the epitope may come together from two or more non-contiguous regions of the polypeptide. The epitope may or may not be a three-dimensional surface feature of the antigen.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the light and heavy chains are primarily responsible for the interaction of the antibody with antigen. Numbering of amino acid positions used herein is according to the EU Index, as in See Kabat, E. A. et al. (1991) Sequences of Proteins of Immunological Interest, Fifth Edition, U.S. Department of Health and Human Services, NIH Publication No. 91-3242. In some embodiments, the variable region is a human variable region.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with a drug, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level.

Alternatively, an mRNA can be "downregulated", or expressed at a lower level, in response to administration of certain compounds or other agents. A downregulated mRNA can be, for example, present at a level of about 99%, 95%, 90%, 80%, 70%, 60%, 50%, 40%, 30%, 20%, 10%, 1% or less of the comparative control mRNA level.

Similarly, the level of a polypeptide or protein biomarker from a patient sample can be increased when treated with a drug, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level.

Alternatively, the level of a protein biomarker can be decreased in response to administration of certain compounds or other agents. This decrease can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

"Sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence. Another indication that nucleotide sequences are substantially identical is if two molecules hybridize to each other under stringent conditions.

The terms "isolated" and "purified" refer to isolation of a substance (such as mRNA, antibody or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include but are not limited to whole blood, partially purified blood, PBMCs, tissue biopsies, and the like.

The term "capture agent," as used herein, refers to an agent that binds an mRNA or protein through an interaction that is sufficient to permit the agent to bind and concentrate the mRNA or protein from a homogeneous mixture.

The term "probe" as used herein, refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term stringent assay conditions generally refers to the combination of hybridization and wash conditions.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The terms "polymerase chain reaction," or "PCR," as used herein generally refers to a procedure wherein small amounts of a nucleic acid, RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, NY, 1989).

The term "cycle number" or "CT" when used herein in reference to PCR methods, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical cocrystals wherein the crystalline molecular complexes containing a therapeutic compound and one or more additional non-volatile compound(s) (referred to herein as counter-molecule(s)). A counter-molecule in a pharmaceutical cocrystal is typically a non-toxic pharmaceutically acceptable molecule, such as, for example, food additives, preservatives, pharmaceutical excipients, or other APIs. In some embodiments, pharmaceutical cocrystals enhance certain physicochemical properties of drug products (e.g., solubility, dissolution rate, bioavailability and/or stability). without compromising the chemical structural integrity of the active pharmaceutical ingredient (API). See, e.g., Jones et al., "Pharmaceutical Cocrystals: An Emerging Approach to Physical Property Enhancement," *MRS Bulletin*, 2006, 31, 875-879; Trask, "An Overview of Pharmaceutical Cocrystals as Intellectual Property," *Molecular Pharmaceutics,* 2007, 4(3), 301-309; Schultheiss & Newman, "Pharmaceutical Cocrystals and Their Physicochemical Properties," *Crystal Growth & Design,* 2009, 9(6), 2950-2967; Shan & Zaworotko, "The Role of Cocrystals in Pharmaceutical Science," *Drug Discovery Today,* 2008, 13(9/10), 440-446; and Vishweshwar et al., "Pharmaceutical Co-Crystals," *J. Pharm. Sci.,* 2006, 95(3), 499-516.

A biological marker or "biomarker" is a substance whose detection indicates a particular biological state, such as, for example, the presence of cancer. In some embodiments, biomarkers can either be determined individually, or several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as a mRNA or cDNA.

In additional embodiments, a "biomarker" indicates a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

6.2 Methods of Assessing the Efficacy of a Compound

In one embodiment, provided herein are methods of determining whether a compound is immunomodulatory, comprising: (a) contacting a first cell with the compound; (b) obtaining a first sample from the first cell from step (a); (c) determining the level of a CRBN-associated protein in the first sample; and (d) comparing the level of the CRBN-associated protein from step (c) to the level of the same protein obtained from a reference sample, wherein a change in the level as compared to the reference is indicative of the efficacy of the compound as an immunomodulatory compound. In certain embodiments, the contacting in step (a) is performed in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In some embodiments, the cells are peripheral blood mononuclear cells, B cells, T cells, monocytes or granulocytes. In other embodiments, the cells are tumor or cancer cells, e.g., lymphoma, myeloma or leukemia. In one embodiment, the tumor or cancer cells are obtained from a cell line.

In certain embodiment, step (c) comprises: (i) contacting the proteins within the first sample from step (b) with a first antibody that immunospecifically binds to a CRBN-associated protein; (ii) contacting the proteins bound to the first antibody with a second antibody with a detectable label, wherein the second antibody immunospecifically binds to the CRBN-associated protein, and wherein the second antibody immunospecifically binds to a different epitope on the CRBN-associated protein than the first antibody; (iii) detecting the presence of second antibody bound to the proteins; and (iv) determining the amount of the CRBN-associated protein based on the amount of detectable label in the second antibody.

In certain embodiment, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding the CRBN-associated protein; and (iii) determining the RNA level of the CRBN-associated protein based on the amount of the amplified DNA.

In certain embodiments, the compound is immunomodulatory if the level (e.g., protein or RNA level) of the CRBN-associated protein as compared to the reference decreases. In certain embodiments, the compound is immunomodulatory if the level (e.g., protein or RNA level) of the CRBN-associated protein as compared to the reference increases. In one embodiment, the reference is prepared by using a second cell not contacted with the compound; wherein the second cell is of the same type as the first cell.

In another embodiment, provided herein are methods of assessing the efficacy of a compound in treating a disease or disorder, comprising: (a) administering a compound to a subject having the disease or disorder; (b) obtaining a first sample from the subject; (c) determining the level of a CRBN-associated protein in the first sample; and (d) comparing the level of the CRBN-associated protein from step (c) to the level of the same protein obtained from a reference sample, wherein a change in the level as compared to the reference is indicative of the efficacy of the compound in treating the disease or disorder. In certain embodiments, the disease or disorder is cancer (e.g., solid tumor or blood cancer as described in Section 5.2.3 below) or an inflammatory disease such as systemic lupus erythematosus, Sjogren syndrome, systemic sclerosis, other inflammatory or autoimmune diseases, or an inflammatory disease as described in Section 2.2 above. In certain embodiments, the disease or disorder is multiple myeloma, chronic lymphocytic leukemia, non-Hodgkins Lymphoma, mantle cell lymphoma, systemic lupus erythematosus, Sjogren syndrome, or systemic sclerosis. In some embodiments, the sample is obtained from a tumor biopsy, node biopsy, or a biopsy from bone marrow, spleen, liver, brain or breast.

In certain embodiment, step (c) comprises: (i) contacting the proteins within the first sample from step (b) with a first antibody that immunospecifically binds to a CRBN-associated protein; (ii) contacting the proteins bound to the first antibody with a second antibody with a detectable label, wherein the second antibody immunospecifically binds to the CRBN-associated protein, and wherein the second antibody immunospecifically binds to a different epitope on the CRBN-associated protein than the first antibody; (iii) detecting the presence of second antibody bound to the proteins; and (iv) determining the amount of the CRBN-associated protein based on the amount of detectable label in the second antibody.

In certain embodiment, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding the CRBN-associated protein; and (iii) determining the RNA level of the CRBN-associated protein based on the amount of the amplified DNA.

In certain embodiments, the compound is likely efficacious in treating the disease or disorder if the level (e.g., protein or RNA level) of the CRBN-associated protein as compared to the reference decreases. In certain embodiments, the compound is likely efficacious in treating the disease or disorder if the level (e.g., protein or RNA level) of the CRBN-associated protein as compared to the reference increases. In one embodiment, the reference is prepared by using a second sample obtained from the subject prior to administration of the compound to the subject; wherein the second sample is from the same source as the first sample. In another embodiment, the reference is prepared by using a second sample obtained from a healthy subject not having the disease or disorder; wherein the second sample is from the same source as the first sample.

In various embodiments of the methods provided herein, the compound is a compound provided in Section 5.3 below. In various embodiments of the methods provided herein, the immunomodulatory compound is thalidomide, lenalidomide, pomalidomide, 3-(5-amino-2-methyl-4-oxo-4H-quinazolin-3-yl)-piperidine-2,6-dione or 3-(4-((4-(morpholinomethyl)benzyl)oxy)-1-oxoisoindolin-2-yl)piperidine-2,6-dione, a stereoisomer thereof, or a pharmaceutically acceptable salt, solvate, hydrate, co-crystal, clathrate, or polymorph thereof. In one embodiment, the compound decreases the level (e.g., protein or RNA level) of the CRBN-associated protein as compared to the reference. In another embodiment, the compound increases the level (e.g., protein or RNA level) of the CRBN-associated protein as compared to the reference.

The methods provided herein are based, in part, on the discovery that CRBN is associated with the anti-proliferative activities of certain drugs, such as the compounds provided herein. CRBN or a CRBN-associated protein can be utilized as biomarkers to indicate the effectiveness or progress of a disease treatment with a compound provided herein. Thus, in certain embodiments, the methods provided herein are useful for characterizing a disease or disorder in a subject, prior to, during or after the subject receiving a treatment of an immunomodulatory compound (e.g., a compound provided in Section 5.3 below).

Without being bound to a particular theory, CRBN binding may contribute to or even be required for anti-proliferative or other activities of certain compounds, such as the compounds provided herein. In certain embodiments, the compounds provided herein target CRBN or one or more CRBN-associated proteins. In one embodiment, the compounds provided herein bind directly to CRBN-DDB1 and/or the CRBN E3 ubiquitin-ligase complex. Mutations in CRBN could be associated with resistance to the compounds provided herein.

For example, the levels of CRBN were significantly lower in the pomalidomide-resistant cells line DF15R and the lenalidomide-resistant cells, H929 R10-1, H929 R10-2, H929 R10-3, H929 R10-4 and MM1/R compared to the matched parental lines. Furthermore, an interesting mutation was found in CRBN gene of one of the myeloma lines that had acquired resistance to lenalidomide while in the parental line the CRBN gene was wild type. This mutation mapped to the DDB1 binding domain in CRBN. Thus, in certain embodiments, the sensitivity of a cancer cell, e.g., a myeloma cell, or a patient having cancer, to therapy with a compound provided herein is related to CRBN expression.

In relapsed or refractory diffuse large B-cell lymphoma (DLBCL), higher responses were seen in the activated B-cell-like (ABC) subtype than the germinal center B-cell-like subtype. As provided herein using DLBCL cell lines, it was shown that lenalidomide treatment preferentially suppressed proliferation of ABC-DLBCL cells in vitro and delayed tumor growth in a human tumor xenograft model, with minimal effect on non-ABC-DLBCL cells. This tumoricidal effect was associated with downregulation of interferon regulatory factor 4 (IRF4), a hallmark of ABC-DLBCL cells.

IRF4 inhibition by lenalidomide caused downregulation of B cell receptor (BCR)-dependent NF-κB activation. While IRF4-specific siRNA mimicked effects of lenalidomide reducing NF-κB activation, IRF4 overexpression enhanced NF-κB activation and conferred resistance to lenalidomide. Furthermore, lenalidomide-induced IRF4 downregulation required the expression of CRBN. Without being bound to a particular theory, these data show that lenalidomide may have direct antitumor activity against DLBCL cells, preferentially ABC-DLBCL cells, by blocking IRF4 expression and the BCR-NF-κB signaling pathway in a CRBN-dependent manner.

It has been proposed that CRBN protein functions as a substrate receptor for Cul4-E3-ligase complexes through its interaction with DDB1. As provided herein, whether in vivo ubiquitination is associated with drug responses in multiple myeloma cells has been investigated. In H929 cells, compounds provided herein decrease total K48-linked polyubiquitination but not K-63-linked ubiquitination after 30 minutes treatment. At present, nearly two dozen proteins are reported to be degraded by a Cul4-DDB1 ligase2. Several studies have shown Cul4/DDB1-dependent ubiquitination of core histones, DNA repair proteins, cell cycle regulators and key signaling pathways molecules. mTORC1 signaling requires proteasomal function and the involvement of CUL4-DDB1 ubiquitin E3 ligase. Using CST Ubiscan technology, 162 unique ubiquitin-peptides were identified which were significantly modulated by the compounds provided herein after short treatments (1-4 h). The corresponding proteins participate in nucleasome and chromatin function, protein-DNA assembly and histone H2A. The relevance of this early modification in the mode of action of compounds provided herein, and the relationship with CRBN and CUL4/DDB1 activities are under investigation.

In certain embodiments, the methods provided herein are useful for assessing the clinical sensitivity and patient response to treatment an immunomodulatory compound (e.g., a compound provided in Section 5.3 below). In one embodiment, the immunomodulatory compound provided herein regulate (e.g., down-regulate or decreases) CRBN or one or more CRBN-associated proteins. In another embodiment, the immunomodulatory compound provided herein provided herein binds directly to CRBN-DDB1.

In various embodiments of the methods provided herein, the CRBN-associated protein is DDB1, DDB2, GSK3B, CUL4A, CUL4B, XBP-1, FAS1, RANBP6, DUS3L, PHGDH, AMPK, IRF4 or NFκB. In various embodiments of the methods provided herein, the CRBN-associated protein is DDB1, PABPC1, HNRNPR, RPL19, SYNCRIP, H2AFX, HSPA8, ALDOA, H1ST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPS6, GNAS, UBE2Q1, FERMT3, NAP1L2, TPD52, VAPA, EEF1AL3, DDIT4, NEDD8, HIST1H1A, HIST1H1B, PCM1, ikaros zinc finger protein 1 (IKZF1) or ikaros zinc finger protein 3 (IKZF3).

In one embodiment of the methods provided herein, the CRBN-associated protein is IKZF3 (also known as "Aiolos"). In one embodiment of the methods provided herein, the CRBN-associated protein is IKZF3 having a protein molecular weight of 58 kDa. In one embodiment of the methods provided herein, the CRBN-associated protein is IKZF3 having a protein molecular weight of 42 kDa. In another embodiment, the immunomodulatory compounds provided herein down-regulate IKZF3 (Aiolos) expression (e.g., protein expression). In another embodiment, the immunomodulatory compounds provided herein down-regulate IL-2 expression. In another embodiment, IMiDs provided herein down-regulate Aiolos expression (e.g., protein or gene expression). In another embodiment, pomalidomide down-regulate Aiolos expression (e.g., protein or gene expression). In another embodiment, lenalidomide down-regulate Aiolos expression (e.g., protein or gene expression).

IKZF3, also known as "Aiolos," is a member of the Ikaros family of zinc-finger proteins. IKZF3 is a hematopoietic-specific transcription factor involved in the regulation of lymphocyte development (e.g., B lymphocyte proliferation and differentiation). The DNA-binding domain of IKZF3 recognizes the core motif of GGGA. IKZF3 was shown to participates in chromatin remodeling, regulates Bcl family members, binds to HDACs, mSin3, Mi-2 in T cells and acts as a transcriptional repressor. Aiolos-Foxp3 interaction has been shown to silence IL-2 expression in human T cells.

In one embodiment of the methods provided herein, the CRBN-associated protein is IKZF1 (also known as "Ikaros"). In another embodiment, the compounds provided herein down-regulate Ikaros expression (e.g., protein or gene expression). In another embodiment, the compound is pomalidomide and Ikaros expression (e.g., protein or gene expression) is down-regulated. In another embodiment, the compound is lenalidomide and Ikaros expression (e.g., protein or gene expression) is down-regulated. In another embodiment, the compound is 3-(5-amino-2-methyl-4-oxo-4H-quinazolin-3-yl)-piperidine-2,6-dione and Ikaros expression (e.g., protein or gene expression) is down-regulated. In another embodiment, the compound is 3-(4-((4-(morpholinomethyl)benzyl)oxy)-1-oxoisoindolin-2-yl)piperidine-2,6-dione and Ikaros expression (e.g., protein or gene expression) is down-regulated. In another embodiment, the compound is the (S) stereoisomer of 3-(4-((4-(morpholinomethyl)benzyl)oxy)-1-oxoisoindolin-2-yl)piperidine-2,6-dione and Ikaros expression (e.g., protein or gene expression) is down-regulated.

In one embodiment, provided herein are methods of determining whether a compound is immunomodulatory, comprising: (a) contacting a first cell with the compound; (b) obtaining a first sample from the first cell from step (a); (c) determining the level of Aiolos in the first sample; and (d) comparing the level of Aiolos from step (c) to the level of Aiolos obtained from a reference sample, wherein a change in the level as compared to the reference is indicative of the efficacy of the compound as an immunomodulatory compound. In certain embodiments, the contacting in step (a) is performed in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In some embodiments, the cells are peripheral blood mononuclear cells, B cells, T cells, monocytes or granulocytes. In other embodiments, the cells are tumor or cancer cells, e.g., lymphoma, myeloma or leukemia. In one embodiment, the tumor or cancer cells are obtained from a cell line.

In certain embodiments, step (c) comprises: (i) contacting the proteins within the first sample from step (b) with a first antibody that immunospecifically binds to Aiolos; (ii) contacting the proteins bound to the first antibody with a second antibody with a detectable label, wherein the second antibody immunospecifically binds to Aiolos, and wherein the second antibody immunospecifically binds to a different epitope on Aiolos than the first antibody; (iii) detecting the presence of second antibody bound to the proteins; and (iv) determining the amount of Aiolos based on the amount of detectable label in the second antibody.

In certain embodiments, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding Aiolos; and (iii) determining the RNA level of Aiolos based on the amount of the amplified DNA.

In certain embodiments, the compound is immunomodulatory if the level (e.g., protein or RNA level) of Aiolos as compared to the reference decreases. In certain embodiments, the compound is immunomodulatory if the level (e.g., protein or RNA level) of Aiolos as compared to the reference increases. In one embodiment, the reference is prepared by using a second cell not contacted with the compound; wherein the second cell is of the same type as the first cell.

In another embodiment, provided herein are methods of assessing the efficacy of a compound in treating a disease or disorder, comprising: (a) administering a compound to a subject having the disease or disorder; (b) obtaining a first sample from the subject; (c) determining the level of Aiolos in the first sample; and (d) comparing the level of t Aiolos from step (c) to the level of the same protein obtained from a reference sample, wherein a change in the level as compared to the reference is indicative of the efficacy of the compound in treating the disease or disorder. In certain embodiments, the disease or disorder is cancer (e.g., solid tumor or blood cancer as described in section 5.2.3 below) or an inflammatory disease such as systemic lupus erythematosus, Sjogren syndrome, systemic sclerosis, other inflammatory or autoimmune diseases, or an inflammatory disease as described in section 2.2 above. In certain embodiments, the disease or disorder is multiple myeloma, chronic lymphocytic leukemia, non-Hodgkins Lymphoma, mantle cell lymphoma, systemic lupus erythematosus, Sjogren syndrome, or systemic sclerosis. In some embodiments, the sample is obtained from a tumor biopsy, node biopsy, or a biopsy from bone marrow, spleen, liver, brain or breast.

In certain embodiment, step (c) comprises: (i) contacting the proteins within the first sample from step (b) with a first antibody that immunospecifically binds to Aiolos; (ii) contacting the proteins bound to the first antibody with a second antibody with a detectable label, wherein the second antibody immunospecifically binds to Aiolos, and wherein the second antibody immunospecifically binds to a different epitope on Aiolos than the first antibody; (iii) detecting the presence of second antibody bound to the proteins; and (iv) determining the amount of Aiolos based on the amount of detectable label in the second antibody.

In certain embodiment, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding Aiolos; and (iii) determining the RNA level of Aiolos based on the amount of the amplified DNA.

In one embodiment, provided herein are methods of determining whether a compound is immunomodulatory, comprising: (a) contacting a first cell with the compound; (b) obtaining a first sample from the first cell from step (a); (c) determining the level of Ikaros in the first sample; and (d) comparing the level of Ikaros from step (c) to the level of Ikaros obtained from a reference sample, wherein a change in the level as compared to the reference is indicative of the efficacy of the compound as an immunomodulatory compound. In certain embodiments, the contacting in step (a) is performed in vitro. In other embodiments, the contacting in step (a) is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In some embodiments, the cells are peripheral blood mononuclear cells, B cells, T cells, monocytes or granulocytes. In other embodiments, the cells are tumor or cancer cells, e.g., lymphoma, myeloma or leukemia. In one embodiment, the tumor or cancer cells are obtained from a cell line.

In certain embodiments, step (c) comprises: (i) contacting the proteins within the first sample from step (b) with a first antibody that immunospecifically binds to Ikaros; (ii) contacting the proteins bound to the first antibody with a second antibody with a detectable label, wherein the second antibody immunospecifically binds to Ikaros, and wherein the second antibody immunospecifically binds to a different epitope on Ikaros than the first antibody; (iii) detecting the presence of second antibody bound to the proteins; and (iv) determining the amount of Ikaros based on the amount of detectable label in the second antibody.

In certain embodiments, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding Ikaros; and (iii) determining the RNA level of Ikaros based on the amount of the amplified DNA.

In certain embodiments, the compound is immunomodulatory if the level (e.g., protein or RNA level) of Ikaros as compared to the reference decreases. In certain embodiments, the compound is immunomodulatory if the level (e.g., protein or RNA level) of Ikaros as compared to the reference increases. In one embodiment, the reference is prepared by using a second cell not contacted with the compound; wherein the second cell is of the same type as the first cell.

In another embodiment, provided herein are methods of assessing the efficacy of a compound in treating a disease or disorder, comprising: (a) administering a compound to a subject having the disease or disorder; (b) obtaining a first sample from the subject; (c) determining the level of Ikaros in the first sample; and (d) comparing the level of t Ikaros from step (c) to the level of the same protein obtained from a reference sample, wherein a change in the level as compared to the reference is indicative of the efficacy of the compound in treating the disease or disorder. In certain embodiments, the disease or disorder is cancer (e.g., solid tumor or blood cancer as described in section 5.2.3 below) or an inflammatory disease such as systemic lupus erythematosus, Sjogren syndrome, systemic sclerosis, other inflammatory or autoimmune diseases, or an inflammatory disease as described in section 2.2 above. In certain embodiments, the disease or disorder is multiple myeloma, chronic lymphocytic leukemia, non-Hodgkins Lymphoma, mantle cell lymphoma, systemic lupus erythematosus, Sjogren syndrome, or systemic sclerosis. In some embodiments, the sample is obtained from a tumor biopsy, node biopsy, or a biopsy from bone marrow, spleen, liver, brain or breast.

In certain embodiment, step (c) comprises: (i) contacting the proteins within the first sample from step (b) with a first antibody that immunospecifically binds to Ikaros; (ii) contacting the proteins bound to the first antibody with a second antibody with a detectable label, wherein the second antibody immunospecifically binds to Ikaros, and wherein the second antibody immunospecifically binds to a different epitope on Ikaros than the first antibody; (iii) detecting the presence of second antibody bound to the proteins; and (iv) determining the amount of Ikaros based on the amount of detectable label in the second antibody.

In certain embodiment, step (c) comprises: (i) contacting the RNA within the first sample with a primer comprising a sequence specifically binding to the RNA to generate a first DNA molecule having a sequence complementary to the RNA; (ii) amplifying the DNA corresponding to a segment of a gene encoding Ikaros; and (iii) determining the RNA level of Ikaros based on the amount of the amplified DNA.

In certain embodiments, the compound is likely efficacious in treating the disease or disorder if the level (e.g., protein or RNA level) of Aiolos or Ikaros as compared to the reference decreases. In certain embodiments, the compound is likely efficacious in treating the disease or disorder if the level (e.g., protein or RNA level) of Aiolos or Ikaros as compared to the reference increases. In one embodiment, the reference is prepared by using a second sample obtained from the subject prior to administration of the compound to the subject; wherein the second sample is from the same source as the first sample. In another embodiment, the reference is prepared by using a second sample obtained from a healthy subject not having the disease or disorder; wherein the second sample is from the same source as the first sample.

In various embodiments of the methods provided herein, the compound is a compound provided in Section 5.3 below. In various embodiments of the methods provided herein, the immunomodulatory compound is thalidomide, lenalidomide, pomalidomide, 3-(5-amino-2-methyl-4-oxo-4H-quinazolin-3-yl)-piperidine-2,6-dione or 3-(4-((4-(morpholinomethyl)benzyl)oxy)-1-oxoisoindolin-2-yl)piperidine-2,6-dione, a stereoisomer thereof, or a pharmaceutically acceptable salt, solvate, hydrate, co-crystal, clathrate, or polymorph thereof. In one embodiment, the compound decreases the level (e.g., protein or RNA level) of the CRBN-associated protein as compared to the reference. In another embodiment, the compound increases the level (e.g., protein or RNA level) of the CRBN-associated protein as compared to the reference. In another embodiment, the compound decreases the level (e.g., protein or RNA level) of the Aiolos or Ikaros as compared to the reference. In another embodiment, the compound increases the level (e.g., protein or RNA level) of Aiolos or Ikaros as compared to the reference. In another embodiment, the compound decreases the level (e.g., protein or RNA level) of Aiolos having a protein molecular weight of 42 kDa as compared to the reference. In another embodiment, the compound increases the level (e.g., protein or RNA level) of Aiolos having a protein molecular weight of 42 kDa as compared to the reference. In another embodiment, the compound decreases the level (e.g., protein or RNA level) of Aiolos having a molecular weight of 58 kDa as compared to the reference.

In various embodiments of the methods provided herein, the disease or disorder is cancer or an inflammatory disease. In various embodiments of the methods provided herein, the disease or disorder is multiple myeloma, chronic lymphocytic leukemia, non-Hodgkins Lymphoma, mantle cell lymphoma, systemic lupus erythematosus, Sjogren syndrome, or systemic sclerosis.

6.2.1 Methods of Detecting and Quantifying Cereblon or Cereblon-Associated Proteins In certain embodiments, provided herein are methods of detecting and quantifying the protein level of CRBN or a CRBN-associated protein from a biological sample, comprising: (a) contacting the sample with a first antibody that immunospecifically binds to the CRBN or CRBN-associated protein; (b) contacting the sample bound to the first antibody with a second antibody with a detectable label, wherein the second antibody immunospecifically binds to the CRBN or CRBN-associated protein, and wherein the second antibody immunospecifically binds to a different epitope on CRBN or the CRBN-associated protein than the first antibody; (c) detecting the presence of second antibody bound to the sample; and (d) determining the protein level of the CRBN or CRBN-associated protein based on the amount of detectable label in the second antibody.

In certain embodiments, provided herein are methods of detecting and quantifying the RNA (e.g., mRNA) level of CRBN or a CRBN-associated protein from a biological sample, comprising: (a) obtaining RNA from the sample; (b) contacting the RNA with a primer comprising a sequence specifically binding to a sequence in the RNA to generate a first DNA molecule having a sequence complementary to said RNA; (c) amplifying the DNA corresponding to a segment of a gene encoding the CRBN or CRBN-associated protein; and (d) determining the RNA level of the CRBN or CRBN-associated protein based on the amount of the amplified DNA.

In certain embodiments, the CRBN-associated protein is DDB1, DDB2, GSK3B, CUL4A, CUL4B, XBP-1, FAS1, RANBP6, DUS3L, PHGDH, AMPK, IRF4 or NFκB. In certain embodiments, the CRBN-associated protein is DDB1, PABPC1, HNRNPR, RPL19, SYNCRIP, H2AFX, HSPA8, ALDOA, H1ST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPS6, GNAS, UBE2Q1, FERMT3, NAP1L2, TPD52, VAPA, EEF1AL3, DDIT4, NEDD8, HIST1H1A, HIST1H1B, PCM1 or IKZF3. In one embodiment, the CRBN-associated protein is IKZF3.

In one embodiment, provided herein are methods of detecting and quantifying the protein level of Aiolos from a biological sample, comprising: (a) contacting the sample with a first antibody that immunospecifically binds to Aiolos; (b) contacting the sample bound to the first antibody with a second antibody with a detectable label, wherein the second antibody immunospecifically binds to Aiolos, and wherein the second antibody immunospecifically binds to a different epitope on Aiolos than the first antibody; (c) detecting the presence of second antibody bound to the sample; and (d) determining the protein level of Aiolos based on the amount of detectable label in the second antibody.

In another embodiment, provided herein are methods of detecting and quantifying the RNA (e.g., mRNA) level of Aiolos from a biological sample, comprising: (a) obtaining RNA from the sample; (b) contacting the RNA with a primer comprising a sequence specifically binding to a sequence in the RNA to generate a first DNA molecule having a sequence complementary to said RNA; (c) amplifying the DNA corresponding to a segment of a gene encoding Aiolos; and (d) determining the RNA level of Aiolos based on the amount of the amplified DNA.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of CRBN or a CRBN-associated protein are immunoassays such as western blot analysis, and an enzyme-linked immunosorbent assay (ELISA) (e.g., a sandwich ELISA). An exemplary assay provided herein for the methods of detecting and quantifying the RNA level of CRBN or a CRBN-associated protein is reverse transcription polymerase chain reaction (RT-PCR), e.g., quantitative PCR or qPCR.

6.2.2 Subjects and Samples

In certain embodiments, the various methods provided herein use samples (e.g., biological samples) from subjects or individuals (e.g., patients). The subject can be a patient, for example, a patient with a blood cancer such as multiple myeloma, leukemia or a lymphoma; inflammation or minimal residual disease. The subject can be a mammal, for example, a human. The subject can be male or female, and can be an adult, child or infant. Samples can be analyzed at a time during an active phase of a disease or disorder, or when a disease or disorder is inactive. In certain embodiments, more than one sample from a subject can be obtained.

In certain embodiments, the sample used in the methods provided herein comprises body fluids from a subject. Non-limiting examples of body fluids include blood (e.g., peripheral whole blood, peripheral blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., a compound provided in Section 5.3 below) to the subject.

6.2.3 Types of Cells

In certain embodiments, the sample used in the methods provided herein comprises a plurality of cells. Such cells can include any type of cells, e.g., stem cells, blood cells (e.g., peripheral blood mononuclear cells), lymphocytes, B cells, T cells, monocytes, granulocytes, immune cells, or tumor or cancer cells. The tumor or cancer cells or a tumor tissue, such as a tumor biopsy or a tumor explants. T cells (T lymphocytes) include, for example, helper T cells (effector T cells or Th cells), cytotoxic T cells (CTLs), memory T cells, and regulatory T cells. In one embodiment, the cells used in the methods provided herein are $CD3^+$ T cells, e.g., as detected by flow cytometry. The number of T cells used in the methods can range from a single cell to about $10^9$ cells. B cells (B lymphocytes) include, for example, plasma B cells, memory B cells, B1 cells, B2 cells, marginal-zone B cells, and follicular B cells. B cells can express immunoglobulins (antibodies, B cell receptor). In one embodiment, the cells used in the methods provided herein are $CD20^+$ B cells, e.g., as detected by flow cytometry.

Specific cell populations can be obtained using a combination of commercially available antibodies (e.g., Quest Diagnostic (San Juan Capistrano, Calif.); Dako (Denmark)).

The cells in the methods provided herein can be obtained from a cell line. In certain embodiments, the cell line is pomalidomide-resistant cell line DF15R. In other embodiments, the cell line is lenalidomide-resistant H929 R10-1, H929 R10-2, H929 R10-3, H929 R10-4 or MM1/R cell line. In certain embodiments, the cell line used in the methods provided herein is a lymphoma cell line. In certain embodiments, the cell line is a leukemia cell line. In certain embodiments, the cell line is a ABC-DLBCL (activated B cell-like diffuse large B-cell lymphoma) cell line, for example, U2932 cell line. In certain embodiments, the cell line is a GCB-DLBCL (germinal center B cell-like diffuse large B-cell lymphoma) cell line, for example, OCI-LY19 or WSU-DLBCL2 cell line. In certain embodiments, the cell line is a MCL cell line, for example, Rec-1, Mino, JeKo-1 or GRanta-519 cell line. In certain embodiments, the cell line is a MCL cell line, for example, U266 cell line. In one embodiment, the cell line is U2932, OCI-LY19, WSU-DLBCL2, Rec-1, Mino, JeKo-1, GRanta-519 or U266 cell line. In another embodiment, the tumor or cancer cell line is a cell line of the blood cancer or solid tumor described below. In another embodiment, the tumor tissue is from an individual having a cancer, for example, a solid tumor or a blood cancer.

In some embodiments, the cancer is a blood cancer. In one embodiment, the blood cancer is multiple myeloma. In another embodiment, the blood cancer is chronic lymphocytic leukemia (CLL). In another embodiment, the blood cancer is diffuse large B-cell lymphoma (DLBCL). In another embodiment, the blood cancer is myelodysplastic syndrome, an acute leukemia, e.g., acute T cell leukemia, acute myelogenous leukemia (AML), acute promyelocytic leukemia, acute myeloblastic leukemia, acute megakaryoblastic leukemia, precursor B acute lymphoblastic leukemia, precursor T acute lymphoblastic leukemia, Burkitt's leukemia (Burkitt's lymphoma), or acute biphenotypic leukemia; a chronic leukemia, e.g., chronic myeloid lymphoma, chronic myelogenous leukemia (CML), chronic monocytic leukemia, Small lymphocytic lymphoma, or B-cell prolymphocytic leukemia; hairy cell lymphoma; T-cell prolymphocytic leukemia; or a lymphoma, e.g, histiocytic lymphoma, lymphoplasmacytic lymphoma (e.g., Waldenström macroglobulinemia), splenic marginal zone lymphoma, plasma cell neoplasm (e.g., plasma cell myeloma, plasmacytoma, a monoclonal immunoglobulin deposition disease, or a heavy chain disease), extranodal marginal zone B cell lymphoma (MALT lymphoma), nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides (Sezary syndrome), a primary cutaneous CD30-positive T cell lymphoproliferative disorder (e.g., primary cutaneous anaplastic large cell lymphoma or lymphomatoid papulosis), angioimmunoblastic T cell lymphoma, peripheral T cell lymphoma, unspecified, anaplastic large cell lymphoma, a Hodgkin's lymphoma or a nodular lymphocyte-predominant Hodgkin's lymphoma.

In other embodiments, the cancer is a solid tumor, e.g., a carcinoma, such as an adenocarcinoma, an adrenocortical carcinoma, a colon adenocarcinoma, a colorectal adenocarcinoma, a colorectal carcinoma, a ductal cell carcinoma, a lung carcinoma, a thyroid carcinoma, a nasopharyngeal carcinoma, a melanoma (e.g., a malignant melanoma), a non-melanoma skin carcinoma, or an unspecified carcinoma; a desmoid tumor; a desmoplastic small round cell tumor; an endocrine tumor; an Ewing sarcoma; a germ cell tumor (e.g., testicular cancer, ovarian cancer, choriocarcinoma, endodermal sinus tumor, germinoma, etc.); a hepatosblastoma; a hepatocellular carcinoma; a neuroblastoma; a non-rhabdomyosarcoma soft tissue sarcoma; an osteosarcoma; a retinoblastoma; a rhabdomyosarcoma; or a Wilms tumor. In another embodiment, the solid tumor is pancreatic cancer or breast cancer. In other embodiments, the solid tumor is an acoustic neuroma; an astrocytoma (e.g., a grade I pilocytic astrocytoma, a grade II low-grade astrocytoma; a grade III anaplastic astrocytoma; or a grade IV glioblastoma multiforme); a chordoma; a craniopharyngioma; a glioma (e.g., a brain stem glioma; an ependymoma; a mixed glioma; an optic nerve glioma; or a subependymoma); a glioblastoma; a medulloblastoma; a meningioma; a metastatic brain tumor; an oligodendroglioma; a pineoblastoma; a pituitary tumor; a primitive neuroectodermal tumor; or a schwannoma. In another embodiment, the cancer is prostate cancer.

In certain embodiments, the tumor cells are tumor cell line cells. In other embodiments, the tumor cells are tumor stem cells or cancer stem cells. In one embodiment, the tumor cells are mesothelioma cells, melanoma cells, adenoma cells, carcinoma cells, adenocarcinoma cells, ductal carcinoma cells, leukemia cells, acute myelogenous leukemia cells, acute myeloid leukemia cells, acute T cell leukemia cells, acute lymphoblastic leukemia cells, hairy cell leukemia cells, acute promyelocytic leukemia cells, lymphoma cells, Burkitt's lymphoma cells, B cell chronic lymphocytic leukemia cells, non-Hodgkin's lymphoma cells, Hodgkin's lymphoma cells, or multiple myeloma cells. rhabdomyosarcoma cells, osteosarcoma cells, neuroblastoma cells, astrocytoma cells, or glioblastoma cells. In another embodiment, the tumor cell line is 5637 (Carcinoma), KHOS/NP (Osteosarcoma), MNNG/HOS (Osteosarcoma), Saos-2 (Osteosarcoma), U-2 OS (Osteosarcoma), SJSA-1 (Osteosarcoma), CCF-STTG1 (Astrocytoma), DBTRG-05MG (Glioblastoma), U87 MG (Glioblastoma), T98G (Glioblastoma), SK-N-SH (Neuroblastoma), SK-N-AS (Neuroblastoma), MCF-7 (Adenocarcinoma), MDA-MB-231 (Adenocarcinoma), MDA-MB-436 (Adenocarcinoma), SK-BR-3 (Adenocarcinoma), BT-20 (Carcinoma), BT-474 (Carcinoma), CAMA-1 (Carcinoma), HCC2218 (Carcinoma), SW527 (Carcinoma), MDA-MB-453 (Carcinoma), MDA-MB-435S (Carcinoma), T-47D (Carcinoma), ZR-75-1 (Carcinoma), UACC-812 (Carcinoma), HCC1419 (Carcinoma), HeLa (Adenocarcinoma), Caco-2 (Adenocarcinoma), COLO205 (Adenocarcinoma), COLO320/DM (Adenocarcinoma), DLD-1 (Adenocarcinoma), HCT-15 (Adenocarcinoma), SK-CO-1 (Adenocarcinoma), SW48 (Adenocarcinoma), SW480 (Adenocarcinoma), HCT-8 (Adenocarcinoma), RKO (Carcinoma), LS411N (Carcinoma), T84 (Carcinoma), AGS (Adenocarcinoma), KATO III (Carcinoma), NCI-N87 (Carcinoma), SNU-16 (Carcinoma), 769-P (Adenocarcinoma), 786-O (Adenocarcinoma), ACHN (Adenocarcinoma), A-498 (Carcinoma), Caki-1 (Carcinoma), G-402 (Leiomyoblastoma), CML-T1 (Leukemia), CTV-1 (Leukemia), JVM-2 (Leukemia), K562 (Leukemia), MHH-CALL2 (Leukemia), NALM-6 (Leukemia), 8E5 (Leukemia), CCRF-SB (Leukemia), CEM/C1 (Leukemia), CEM/C2 (Leukemia), CEM-CM3 (Leukemia), CCRF-HSB-2 (Leukemia), KG-1 (Leukemia), KG-1a (Leukemia), CCRF-CEM (Leukemia), MOLT-3 (Leukemia), SUP-B15 (Leukemia), TALL-104 (Leukemia), Loucy (Leukemia), RS4-11 (Leukemia), REH (Leukemia), AML-193 (Leukemia), THP-1 (Leukemia), MOLM-13 (Leukemia), Kasumi-1 (Leukemia), Kasumi-3 (Leukemia), BDCM (Leukemia), HL-60 (Leukemia), 12.1 (Leukemia), 19.2 (Leukemia), J.gamma1.WT (Leukemia), J.RT3-T3.5 (Leukemia), P116 (Leukemia), P116.cl39 [P116.c39] (Leukemia), D1.1 (Leukemia), J45.01 (Leukemia), MV-4-11 (Leukemia), Kasumi-4 (Leukemia), MEG-01 (Leukemia), KU812 (Leukemia), Mo (Leukemia), JM1 (Leukemia), GDM-1 (Leukemia), CESS (Leukemia), ARH-77 (Leukemia), SK-HEP-1 (Adenocarcinoma), Bel-7402 (Carcinoma), Bel-7404 (Carcinoma), HEP-3B (Carcinoma), HepG2 (Carcinoma), Calu-3 (Adenocarcinoma), NCI-H1395 (Adenocarcinoma), NCI-H1975 (Adenocarcinoma), SK-LU-1 (Adenocarcinoma), NCI-H2122 (Adenocarcinoma), NCI-H727 (Carcinoid), A-427 (Carcinoma), A549 (Carcinoma), SW1573 (Carcinoma), NCI-H358 (Carcinoma), NCI-H460 (Carcinoma), NCI-H292 (Carcinoma), NCI-H82 (Carcinoma), NCI-H226 (Carcinoma), NCI-H526 (Carcinoma), or MSTO-211H (Mesothelioma).

In certain embodiments, the sample used in the methods provided herein is from a diseased tissue, e.g., from an individual having cancer, inflammation or a hematopoietic disease or disorder. In some embodiments, the cancer is a solid tumor or blood cancer, as described above. In other embodiments, the hematopoietic disease or disorder is hemoglobinopathy, immunodeficiency or minimal residual disease. In certain embodiments, the methods provided herein are useful for detecting gene rearrangement in cells from a healthy individual. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

In one embodiment, the RNA (e.g., mRNA) or protein is purified from the tumor and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

6.2.4 Methods of Detecting mRNA Levels in a Sample

Several methods of detecting or quantitating mRNA levels are known in the art. Exemplary methods include but are not limited to northern blots, ribonuclease protection assays, PCR-based methods, and the like. The mRNA sequence, e.g., the mRNA of CRBN or CRBN-associated proteins, or a fragment thereof, can be used to prepare a probe that is at least partially complementary. The probe can then be used to detect the mRNA sequence in a sample, using any suitable assay, such as PCR-based methods, Northern blotting, a dipstick assay, and the like.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA that has altered expression during an immunomodulatory treatment in a patient, such as the mRNA of CRBN or CRBN-associated proteins. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of the mRNA in a sample. For example, an assay may be in the form of a dipstick, a membrane, a chip, a disk, a test strip, a filter, a microsphere, a slide, a multiwell plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology*, 3rd ed., Wiley & Sons 1995 and Sambrook et al., *Molecular Cloning: A Laboratory Manual*, Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

In some embodiments, the mRNA sequences comprise at least one mRNA selected from the group consisting of the mRNA of DDB1, PABPC1, HNRNPR, RPL19, SYNCRIP, H2AFX, HSPA8, ALDOA, H1ST1H2AA, HSPA1A, XRCC6, RPL12, RPL18A, RPL4, HNRNPA2B1, HNRNPC, RPS2, SEC24C, RPL9, USP15, SEC24A, CTPS, ABCE1, EEF1A1, IPO5, CPSF6, KCNAB2, C7ORF42, SMC4, GNB3, H2AFZ, HIST1H1C, HIST1H1D, HIST1H1E, ACTB, CSNK2A1, CRBN, DDX21, DHX9, DNAJC1, G3BP1, HSPA1B, IGF2BP2, RPL10A, RPL13A, RPL14, RPL15, RPL21, RPL3, RPL30, RPL7, RPL7A, RPLP1, RPLP2, MYH10, ILF3, NCL, RPS13, RPS16, RPS19, RPS6, SND1, EIF2S2, HNRNPH2, UBB, EEF1G, TBL1XR1, NACA, EIF4A1, FASN, PPAT, G3BP2, TUBA1A, UBAP2L, MCM2, UAP1, TUBA1C, EIF2S1, EIF3J, PRKDC, MCM7, RPL11, TUBA1B, STAT3, PTRH2, PABPC4, PTPRC, MACF1, UBE2O, DUT, GNB2L1, NUP88, H2AFJ, SEC23B, PDXK, ACLY, ARID1A, GBE1, HSPA9, DDX17, FUBP1, FBXO21, EWSR1, IFI16, YWHAE, UBA52, COPS6, GNAS, UBE2Q1, FERMT3, NAP1L2, TPD52, VAPA, EEF1AL3, DDIT4, NEDD8, HIST1H1A, HIST1H1B, PCM1 or IKZF3, or a fragment thereof. The nucleic acids may be present in specific, addressable locations on a solid support; each corresponding to at least a portion of mRNA sequences that are differentially expressed upon treatment of an immunomodulatory compound in a cell or a patient.

A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al. *Meth. Enzymol.*, 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to follow the expression of CRBN or CRB-associated proteins. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, Real-Time Reverse Transcription-PCR (qRT-PCR) can be used for both the detection and quantification of RNA targets (Bustin, et al., 2005, *Clin. Sci.*, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, real-time PCR gives quantitative results. An additional advantage of real-time PCR is the relative ease and convenience of use. Instruments for real-time PCR, such as the Applied Biosystems 7500, are available commercially, as are the reagents, such as TaqMan Sequence Detection chemistry. For example, TagMan® Gene Expression Assays can be used, following the manufacturer's instructions. These kits are pre-formulated gene expression assays for rapid, reliable detection and quantification of human, mouse and rat mRNA transcripts. An exemplary PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

6.2.5 Methods of Detecting Polypeptide or Protein Levels in a Sample

Several protein detection and quantitation methods can be used to measure the level of CRBN or CRBN-associated proteins. Any suitable protein quantitation method can be used. In some embodiments, antibody-based methods are used. Exemplary methods that can be used include but are not limited to immunoblotting (western blot), enzyme-linked immunosorbent assay (ELISA), immunohistochemistry, flow cytometry, cytometric bead array, mass spectroscopy, and the like. Several types of ELISA are commonly used, including direct ELISA, indirect ELISA, and sandwich ELISA.

6.3 Compounds

Compounds for the methods provided herein include, but are not limited to, the immunomodulatory compounds, including compounds known as "IMiDs®" (Celgene Corporation), a group of compounds that can be useful to treat several types of human diseases, including certain cancers.

As used herein and unless otherwise indicated, the term "immunomodulatory compound" can encompass certain small organic molecules that inhibit LPS induced monocyte TNF-α, IL-1β, IL-12, IL-6, MIP-1α, MCP-1, GM-CSF, G-CSF, and COX-2 production. These compounds can be prepared synthetically, or can be obtained commercially.

Exemplary immunomodulating compounds include but are not limited to N-{[2-(2,6-dioxo(3-piperidyl)-1,3-dioxoisoindolin-4-yl]methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (−)-3-(3,4-Dimethoxyphenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-propionamide; (−)-{2-[1-(3-ethoxy-4-methoxy-phenyl)-2-methylsulfonylethyl]-4-acetylaminoisoindoline-1,3-dione}; (+)-{2-[1-(3-ethoxy-4-methoxyphenyl)-2-methylsulfonylethyl]-4-acetylaminoisoindoline-1,3-dione}; Difluoro-methoxy SelCIDs; 1-phthalimido-1-(3,4-diethoxyphenyl)ethane; 3-(3,4-dimethoxyphenyl)-3-(3,5-dimethoxyphenyl)acrylo nitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropionamide; 1-oxo-2-(2,6-dioxopiperidin-3-yl)-4-methylisoindoline; Cyclopropyl-N-{2-[(1S)-1-(3-ethoxy-4-methoxyphenyl)-2-(methylsulfonyl)ethyl]-3-oxoisoindoline-4-yl}carboxamide; Substituted 2-(3-hydroxy-2,6-dioxopiperidin-5-yl)isoindoline; N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3S)-3-methyl-2,6-dioxo-piperidin-3-yl]-1,3-dioxo-2,3-dihydro-1H-isoindol-5-ylmethyl]-amide; (S)—N-((2-(3-methyl-2,6-dioxopiperidin-3-yl)-1,3-dioxoisoindolin-5-yl)methyl)-4-(trifluoromethyl)benzamide; 3-(2,5-dimethyl-4-oxo-4H-quinazolin-3-yl)-piperidine-2,6-dione, and the like.

The inflammatory cytokine TNF-α, which is produced by macrophages and monocytes during acute inflammation, causes a diverse range of signaling events within cells. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA.

Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Specific examples of immunomodulatory compounds include cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl)isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl)isoindolines (e.g., 4-methyl derivatives of thalidomide), substituted 2-(2,6-dioxopiperidin-3-yl)phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds such as those described in U.S. patent publication no. 2003/0045552 published on Mar. 6, 2003, U.S. patent publication no. 2003/0096841 published on May 22, 2003, and International Application No. PCT/US01/50401 (International Publication No. WO 02/059106). US patent publication no. 2006/0205787 describes 4-amino-2-(3-methyl-2,6-dioxopiperidin-3-yl)-isoindole-1,3-dione compositions. US patent publication no. 2007/0049618 describes isoindole-imide compounds. The entireties of each of the patents and patent applications identified herein are incorporated by reference. In one embodiment, immunomodulatory compounds do not include thalidomide.

Various immunomodulatory compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

Immunomodulatory compounds provided herein include, but are not limited to, 1-oxo- and 1,3 dioxo-2-(2,6-dioxopiperidin-3-yl)isoindolines substituted with amino in the benzo ring as described in U.S. Pat. No. 5,635,517 which is incorporated herein by reference.

These compounds have the structure I:

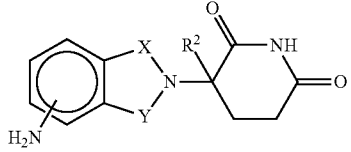

in which one of X and Y is C=O, the other of X and Y is C=O or CH$_2$, and R$^2$ is hydrogen or lower alkyl, in particular methyl. Specific immunomodulatory compounds include, but are not limited to:

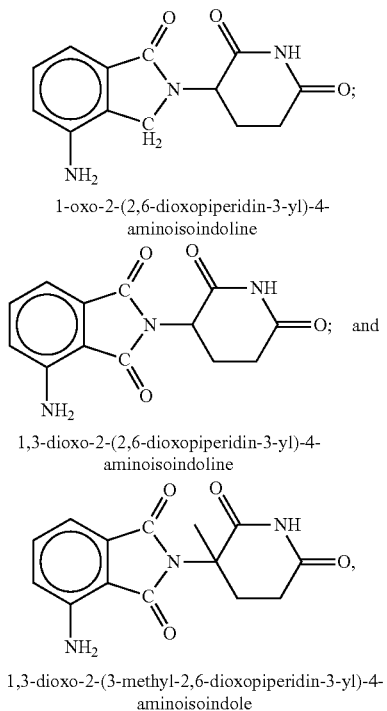

1-oxo-2-(2,6-dioxopiperidin-3-yl)-4-aminoisoindoline 1,3-dioxo-2-(2,6-dioxopiperidin-3-yl)-4-aminoisoindoline 1,3-dioxo-2-(3-methyl-2,6-dioxopiperidin-3-yl)-4-aminoisoindole and optically pure isomers thereof.

The compounds can be obtained via standard, synthetic methods (see e.g., U.S. Pat. No. 5,635,517, incorporated herein by reference). The compounds are also available from Celgene Corporation, Warren, N.J.

Other specific immunomodulatory compounds belong to a class of substituted 2-(2,6-dioxopiperidin-3-yl)phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

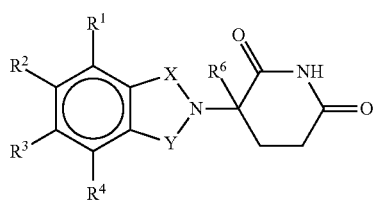

in which:
one of X and Y is C=O and the other of X and Y is C=O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

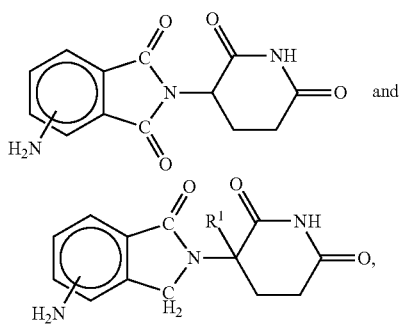

wherein R$^1$ is hydrogen or methyl. In a separate embodiment, provided herein is the use of enantiomerically pure forms (e.g. optically pure (R) or (S) enantiomers) of these compounds.

Still other specific immunomodulatory compounds disclosed herein belong to a class of isoindole-imides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula II:

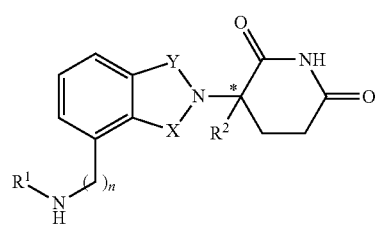

and pharmaceutically acceptable salts, hydrates, solvates, clathrates, enantiomers, diastereomers, racemates, and mixtures of stereoisomers thereof, wherein:
one of X and Y is C=O and the other is CH$_2$ or C=O;
R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)2, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^3$', C(S)NR$^3$R$^3$' or (C$_1$-C$_8$)alkyl-O(CO)R$^5$;
R$^2$ is H, F, benzyl, (C$_1$-C$_8$)alkyl, (C$_2$-C$_8$)alkenyl, or (C$_2$-C$_8$) alkynyl;
R$^3$ and R$^3$' are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)

heteroaryl, $(C_0-C_8)$alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)2$; $(C_0-C_8)$alkyl-NH—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

[structure: ~CH₂-furan]

In another embodiment of the compounds of formula II, $R^1$ is

[structures: ~CH₂-furan, ~CH₂-thiophene, or ~CH(R⁷)-furan with Q, R⁷ substituents]

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_8)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O)NHC(O) can be replaced with $(C_1-C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino)carboxamide.

Still other specific immunomodulatory compounds disclosed herein belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

[Structure III: isoindoline fused with piperidine-2,6-dione, with substituents $R^1, R^2, R^3, R^4$ on the benzene ring, $R^6$ on the ring carbon, X, Y as carbonyl/CH₂, and R on the imide nitrogen]

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1, R^2, R^3$, or $R^4$, independently of the others, is halo, alkyl of 1 to 4 carbon atoms, or alkoxy of 1 to 4 carbon atoms or (ii) one of $R^1, R^2, R^3$, or $R^4$ is nitro or —$NHR^5$ and the remaining of $R^1, R^2, R^3$, or $R^4$ are hydrogen;

$R^5$ is hydrogen or alkyl of 1 to 8 carbons
$R^6$ hydrogen, alkyl of 1 to 8 carbon atoms, benzo, chloro, or fluoro;
R' is $R^7$—$CHR^{10}$—$N(R^8R^9)$;
$R^7$ is m-phenylene or p-phenylene or —($CnH2n$)— in which n has a value of 0 to 4;
each of $R^8$ and $R^9$ taken independently of the other is hydrogen or alkyl of 1 to 8 carbon atoms,
or $R^8$ and $R^9$ taken together are tetramethylene, pentamethylene, hexamethylene,
or —$CH_2CH_2X^1CH_2CH_2$— in which $X^1$ is —O—, —S—, or —NH—;
$R^{10}$ is hydrogen, alkyl of to 8 carbon atoms, or phenyl; and
* represents a chiral-carbon center.
Other representative compounds are of formula:

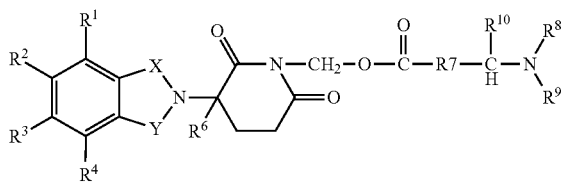

wherein:
one of X and Y is C=O and the other of X and Y is C=O or $CH_2$;
(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen or alkyl of 1 to 8 carbon atoms;
$R^6$ is hydrogen, alkyl of 1 to 8 carbon atoms, benzo, chloro, or fluoro;
$R^7$ is m-phenylene or p-phenylene or —($CnH2n$)— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S—, or —NH—; and
$R^{10}$ is hydrogen, alkyl of to 8 carbon atoms, or phenyl.
Other representative compounds are of formula:

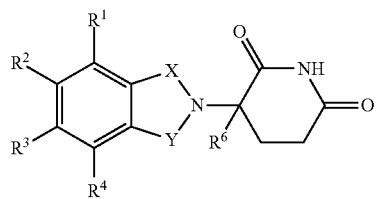

in which
one of X and Y is C=O and the other of X and Y is C=O or $CH_2$;
each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is nitro or protected amino and the remaining of $R^1$, $R^2$, $R^3$, and $R^4$ are hydrogen; and
$R^6$ is hydrogen, alkyl of 1 to 8 carbon atoms, benzo, chloro, or fluoro.

Other representative compounds are of formula:

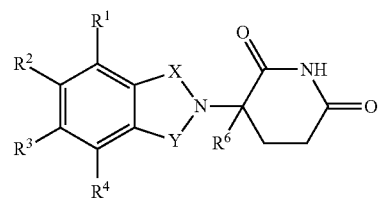

in which:
one of X and Y is C=O and the other of X and Y is C=O or $CH_2$;
(i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is —$NHR^5$ and the remaining of $R^1$, $R^2$, $R^3$, and $R^4$ are hydrogen;
$R^5$ is hydrogen, alkyl of 1 to 8 carbon atoms, or CO—$R^7$—CH($R^{10}$)$NR^8R^9$ in which each of $R^7$, $R^8$, $R^9$, and $R^{10}$ is as herein defined; and
$R^6$ is alkyl of 1 to 8 carbon atoms, benzo, chloro, or fluoro.
Specific examples of the compounds are of formula:

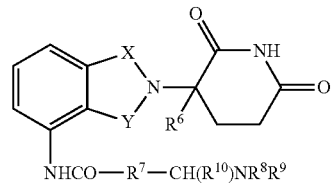

in which:
one of X and Y is C=O and the other of X and Y is C=O or $CH_2$;
$R^6$ is hydrogen, alkyl of 1 to 8 carbon atoms, benzyl, chloro, or fluoro;
$R^7$ is m-phenylene, p-phenylene or —($CnH2n$)— in which n has a value of 0 to 4;
each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X^1CH_2CH_2$— in which $X^1$ is —O—, —S— or —NH—; and
$R^{10}$ is hydrogen, alkyl of 1 to 8 carbon atoms, or phenyl.
Other specific immunomodulatory compounds are 1-oxo-2-(2,6-dioxo-3-fluoropiperidin-3yl) isoindolines and 1,3-dioxo-2-(2,6-dioxo-3-fluoropiperidine-3-yl)isoindolines such as those described in U.S. Pat. Nos. 5,874,448 and 5,955,476, each of which is incorporated herein by reference. Representative compounds are of formula:

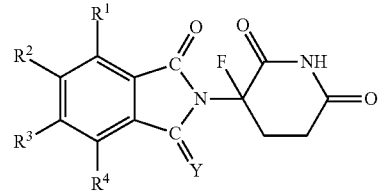

wherein:
Y is oxygen or $H_2$ and
each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds are the tetra substituted 2-(2,6-dioxopiperidin-3-yl)-1-oxoisoindolines described in U.S. Pat. No. 5,798,368, which is incorporated herein by reference. Representative compounds are of formula:

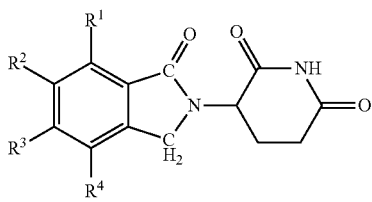

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl)isoindolines disclosed in U.S. Pat. No. 6,403,613, which is incorporated herein by reference. Representative compounds are of formula:

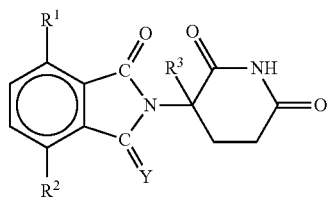

in which
Y is oxygen or $H_2$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and
$R^3$ is hydrogen, alkyl, or benzyl.
Specific examples of the compounds are of formula:

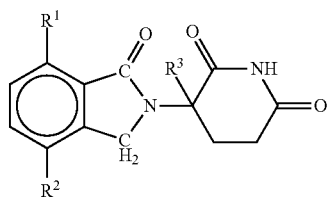

wherein
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

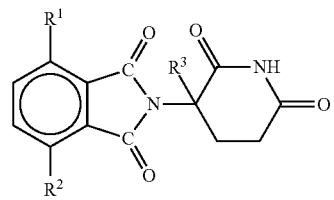

wherein:
a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and
$R^3$ is hydrogen, alkyl of from 1 to 4 carbon atoms, or benzyl.

Other specific immunomodulatory compounds disclosed herein are 1-oxo and 1,3-dioxoisoindolines substituted in the 4- or 5-position of the indoline ring described in U.S. Pat. No. 6,380,239 and U.S. Pat. No. 7,244,759, both of which are incorporated herein by reference. Representative compounds are of formula:

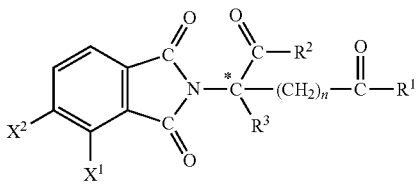

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

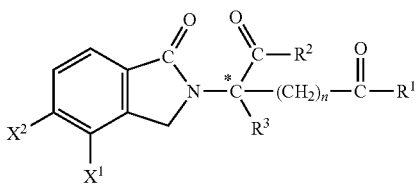

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, prodrugs, and stereoisomers thereof:

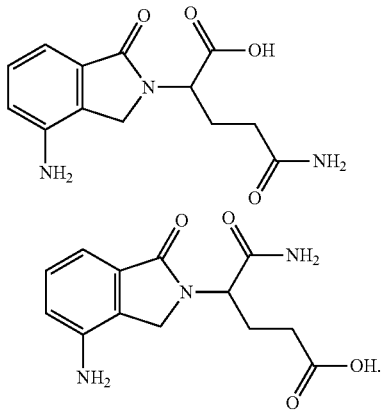

Other representative compounds are of formula:

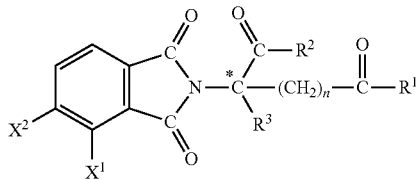

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

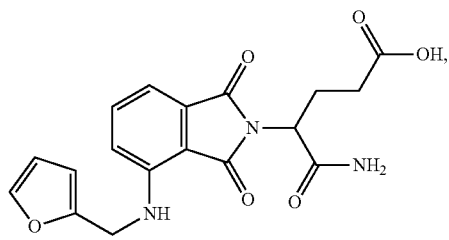

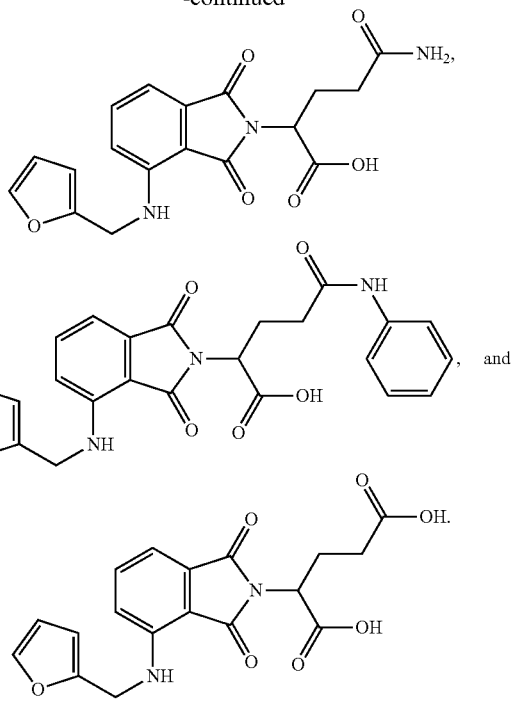

Other specific examples of the compounds are of formula:

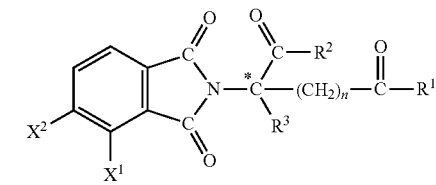

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —COR$^2$ and —(CH$_2$)$_n$COR$^1$ are different, the carbon atom designated C* constitutes a center of chirality.

Other representative compounds are of formula:

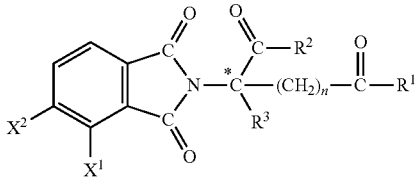

wherein:
one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —COR$^2$ and —(CH$_2$)$_n$COR$^1$ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

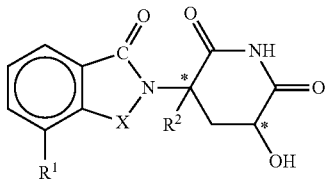

wherein:
the carbon atoms designated * constitute centers of chirality;
X is —C(O)— or —CH$_2$—;
R$^1$ is alkyl of 1 to 8 carbon atoms or —NHR$^3$;
R$^2$ is hydrogen, alkyl of 1 to 8 carbon atoms, or halogen; and
R$^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —COR$^4$ in which
R$^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

Other specific compounds provided herein are of formula:

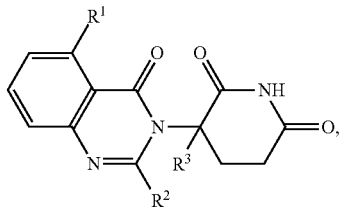

and pharmaceutically acceptable salts, solvates, and stereoisomers thereof, wherein:
R$^1$ is: hydrogen; halo; —(CH$_2$)$_n$OH; (C$_1$-C$_6$)alkyl, optionally substituted with one or more halo; (C$_1$-C$_6$)alkoxy, optionally substituted with one or more halo; or
—(CH$_2$)$_n$NHR$^a$, wherein R$^a$ is:
hydrogen;
(C$_1$-C$_6$)alkyl, optionally substituted with one or more halo;
—(CH$_2$)$_n$-(6 to 10 membered aryl);
—C(O)—(CH$_2$)$_n$-(6 to 10 membered aryl) or —C(O)—(CH$_2$)$_n$-(6 to 10 membered heteroaryl), wherein the aryl or heteroaryl is optionally substituted with one or more of: halo; —SCF$_3$; (C$_1$-C$_6$) alkyl, itself optionally substituted with one or more halo; or (C$_1$-C$_6$)alkoxy, itself optionally substituted with one or more halo;
—C(O)—(C$_1$-C$_8$)alkyl, wherein the alkyl is optionally substituted with one or more halo;
—C(O)—(CH$_2$)$_n$—(C$_3$-C$_{10}$-cycloalkyl);
—C(O)—(CH$_2$)$_n$—NR$^b$R$^c$, wherein R$^b$ and R$^c$ are each independently: hydrogen;
(C$_1$-C$_6$)alkyl, optionally substituted with one or more halo;
(C$_1$-C$_6$)alkoxy, optionally substituted with one or more halo; or
6 to 10 membered aryl, optionally substituted with one or more of: halo;
(C$_1$-C$_6$)alkyl, itself optionally substituted with one or more halo; or
(C$_1$-C$_6$)alkoxy, itself optionally substituted with one or more halo;
—C(O)—(CH$_2$)$_n$—O—(C$_1$-C$_6$)alkyl; or
—C(O)—(CH$_2$)$_n$—O—(CH$_2$)$_n$-(6 to 10 membered aryl);
R$^2$ is: hydrogen; —(CH$_2$)$_n$OH; phenyl; —O—(C$_1$-C$_6$)alkyl; or (C$_1$-C$_6$)alkyl, optionally substituted with one or more halo;
R$^3$ is: hydrogen; or (C$_1$-C$_6$)alkyl, optionally substituted with one or more halo; and
n is 0, 1, or 2.

Specific examples include, but are not limited to, 3-(5-amino-2-methyl-4-oxo-4H-quinazolin-3-yl)-piperidine-2,6-dione ("Compound A"), which has the following structure:

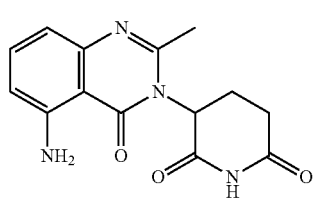

or an enantiomer or a mixture of enantiomers thereof; or a pharmaceutically acceptable salt, solvate, hydrate, co-crystal, clathrate, or polymorph thereof.

Compound A can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Provisional Pat. App. No. 61/451,995, filed Mar. 11, 2011, which is incorporated herein by reference in its entirety.

Other specific compounds provided herein are of formula:

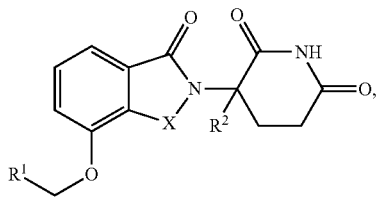

or a pharmaceutically acceptable salt, solvate or stereoisomer thereof, wherein:
X is C=O or CH$_2$;
R$^1$ is —Y—R$^3$;
R$^2$ is H or (C$_1$-C$_6$)alkyl;
Y is: 6 to 10 membered aryl, heteroaryl or heterocycle, each of which may be optionally substituted with one or more halogen; or a bond;
R$^3$ is: —(CH$_2$)$_n$-aryl, —O—(CH$_2$)$_n$-aryl or —(CH$_2$)$_n$—O-aryl, wherein the aryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen;
—(CH$_2$)$_n$-heterocycle, —O—(CH$_2$)$_n$-heterocycle or —(CH$_2$)$_n$—O-heterocycle, wherein the heterocycle is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; or
—(CH$_2$)$_n$-heteroaryl, —O—(CH$_2$)$_n$-heteroaryl or —(CH$_2$)$_n$—O-heteroaryl, wherein the heteroaryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; and
n is 0, 1, 2 or 3.
Specific examples include, but are not limited to, 3-(4-((4-(morpholinomethyl)benzyl)oxy)-1-oxoisoindolin-2-yl)piperidine-2,6-dione. In one embodiment, provided herein is the (S) stereoisomer of 3-(4-((4-(morpholinomethyl)benzyl)oxy)-1-oxoisoindolin-2-yl)piperidine-2,6-dione ("Compound B") e.g., for use in the methods described herein. Racemic 3-(4-((4-(morpholinomethyl)benzyl)oxy)-1-oxoisoindolin-2-yl)piperidine-2,6-dione and methods of preparing the same have been reported in U.S. Patent Publication No. 2011/0196150, which is incorporated herein by reference in its entirety. Compound B has the following structure:

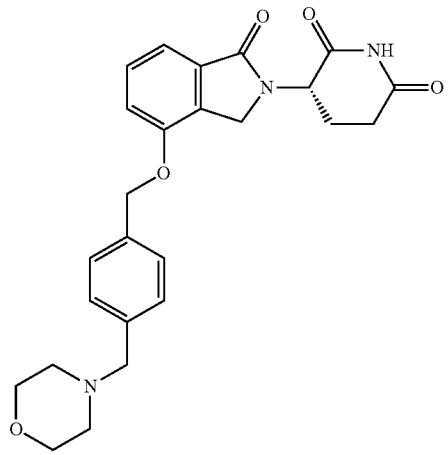

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. US20060188475, US20060205787, and US20070049618, each of which is incorporated by reference herein in its entirety.

The compounds may be small organic molecules having a molecular weight less than about 1,000 g/mol, and are not proteins, peptides, oligonucleotides, oligosaccharides or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

6.4 Kits

Kits and compositions for carrying out the methods provided herein are also contemplated. In certain embodiments, provided herein are kits useful for determining the efficacy of an immunomodulatory compound. In certain embodiments, provided herein are kits useful for determining whether a compound is immunomodulatory. In certain embodiments, provided herein are kits useful for assessing the efficacy of a compound in treating a disease or disorder. In some embodiments, provided herein are kits useful for determining the effect of an immunomodulatory compound. In certain embodiments, provided herein are kits useful for predicting the likelihood of an effective lymphoma, leukemia, multiple myeloma, a solid tumor, non-Hodgkin's lymphoma, diffuse large B-cell lymphoma, mantle cell lymphoma, follicular lymphoma, acute myeloblastic leukemia, chronic lymphocytic leukemia, myelodysplastic syndrome or melanoma treatment or for monitoring the effectiveness of a treatment with one or more compounds (e.g., drugs). The kit comprises a solid support, and a means for detecting the protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In still other embodiments, the kits provided herein are useful for predicting the likelihood of an effective treatment of a disease or disorder selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis and fibrotic conditions such as systemic sclerosis.

In one embodiment a kit provided herein comprises a compound provided herein, or a pharmaceutically acceptable salt, solvate or hydrate thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support and the like, are also contemplated in relation to any of the various methods and/or kits provided herein.

7 EXAMPLES

Certain embodiments of the invention are illustrated by the following non-limiting examples.

7.1 Procedures

7.1.1 Conjugation and Testing of Aiolos Antibody

This example demonstrates the conjugation of the Aiolos antibodies with Alexa Fluor 647 used in certain embodiments of the methods provided herein and the testing of the conjugated antibodies. Briefly, Aiolos 0-21 rabbit polyclonal antibodies (SantaCruz Cat# sc-101982) or other suitable poly or monoclonal antibodies are directly conjugated to Alexa Fluor 647 and then tested for specificity on a positive (peripheral blood) and negative control cell line. The cells are fixed by BD Lyse/Fix followed by BD Perm Buffer I. The specificity of the antibodies is performed with and without testing compounds.

First, 100 µg of purified antibodies are conjugated with 5 molar excess (ME) and 10 ME of Alexa Fluor 647 to determine the optimal conjugation conditions. Post-conjugation specificity is determined by incubating 0.5 µg of each test conjugate and purified antibody with a specific peptide blocker separately. Normal whole blood cells (positive control) and HEK-293 cells (negative control) are processed and stained with the conjugated and purified antibodies (with and without blockers) separately. Purified reagents are developed with appropriate anti-species Alexa Fluor 647 secondary. Signal to noise ratio and the specific fluorescence percentage are determined. If the signal to noise ratio and the specific fluorescence percentage for the conjugated antibodies and purified antibodies are comparable, then the optimal molar ratio of fluorescent dye and antibody is determined. The reminder of the purified antibodies are conjugated at the optimal molar ratio. Complete titration of conjugated antibodies for saturation determination is performed on normal whole blood cells treated or untreated with testing compounds.

7.1.2 Fixation Determination for Cells

Purpose:

To determine an optimum method for detection of all markers of interest while maintaining surface marker expression in PBMCs. PBMCs or fresh normal donor whole blood are treated with either a carrier control or Compound B at 1 micromolar for 2 hours and then processed below. Untreated MM-BMMCs are also used.

Frozen PBMCs (control and treated), fresh normal donor whole blood (control and treated), and frozen MM-BMMCs (untreated only) are thawed and then fixed by one of following fixation/permeabilization methods: (1) BD Lyse/Fix+Perm Buffer I; (2) BD Lyse/Fix+Perm Buffer II; or (3) Esoterix Proprietary fixative.

7.1.3 Assay Stability

The stability of fresh normal donor whole blood samples is examined. Five (5) normal donor whole blood samples (basal expression only) are drawn and fixed by the method determined by the previous example. The fixed samples are split into two aliquots. One aliquot is placed at 4° C. at 1 hour and another placed at −20° C. for 1 hour. These samples are tested immediately (Day 0). Remaining aliquots are stored at 4° C. or −20° C. and tested on 1 day ex-vivo, 2 days ex-vivo and 3 days ex-vivo.

The samples are tested for biological variability by analysis of the basal difference of Aiolos in normal whole blood from 5 different donors.

7.1.4 Intra-Assay Reproducibility and Inter-Operator Precision

To determine the repeatability of the assays, the same 5-NWB samples tested for stability from above are tested in triplicate at one time point. These samples were tested in triplicate in the Day 0, 4° C. prepped samples. To test the Inter-operator precision, the same samples are processed by a second operator on the same day. The analysis includes Aiolos quantitative expression levels in CD19+ a, CD3+ and total CD45+ Lymphocyte population and in (reported in MEFL). The Mean, Standard Deviation and % CV are calculated between replicates and between operators.

7.1.5 Aiolos Determination by FACS Analysis in Cell Lines and PBMCs

This Example demonstrates the determination of Aiolos in cell lines and PBMCs using FACS analysis.

Materials:

BD Fix buffer I (cat#55870); BD Perm Buffer III (cat#558050); BD Stain Buffer (cat#554657); Anti-IKZF3 antibody (Santa Cruz lot #B1612) and secondary antibody (BD FITC Goat Anti-Rabbit Ig cat#554020).

Assay Procedure

The Fix buffer I was warmed up to 37° C. in an incubator or water bath prior to use. The Perm Buffer III was chilled in a −20° C. freezer prior to use. The cells were collected at the end of treatment with testing compounds. One volume of the pre-warmed Fix Buffer I was mixed with one volume of cell suspension. If the volume of the cell suspension is greater than 100 μL, the cells were spun and resuspended in 100 μL medium or PBS. The buffer and the cell suspension were mixed well and incubated in a 37° C. water bath for 10 min. The cells were spun down at 250×g for 10 min and the supernatant was aspirated. The cells were washed once with BD Stain Buffer. The pellet was spun and the supernatant was removed. The cells were vortexed to be loosened, and permeabilized by slowly adding cold Perm Buffer III while vortexing or mixing. Subsequently, the cells were incubated on ice for 30 min. The cells were then spun down and washed twice with Stain Buffer. The supernatant was spun and aspirated. The cells were resuspended in a small volume of Stain buffer (50 or 100 μL containing from 200,000 to 1 million cells). Anti-IKFZ3 antibody was added to the cell suspension at 1:1000 dilution and incubated for 45 min at 4° C. The cells were then spun down and washed once with stain buffer. Secondary antibody was added to the cells at 1:5000 dilution and incubated at room temperature for 20 min in the dark. The cells were washed once with stain buffer prior to analysis by FACS.

7.1.6 Procedure for Cynomolgus Blood Processing for Protein and mRNA Analysis

Cynomolgus (*M. fascicularis*) blood yields approximately 10 million ($10 \times 10^6$) mononuclear cells (PBMCs) per 2.5 ml whole blood (according to protocol by Non Human Primate Reagent Source, Boston). After isolating PBMCs from Cynomolgus blood, approximately $7 \times 10^6$ cells were aliquoted for protein analysis, while $3 \times 10^6$ cells were used for mRNA analysis.

Processing PBMCs for Protein Analysis

The following steps were performed on ice and any centrifugation was performed in a 4° C. refrigerated centrifuge. RIPA lysis buffer (Pierce, cat#89900) was first prepared by adding 10 μL proteinase inhibitors (Pierce, cat#78443) to 1 mL of RIPA buffer. Subsequently, PBMCs were washed once in ice-cold phosphate buffered saline (PBS). The PBMCs were then lysed with 0.25 mL RIPA lysis buffer. The PBMCs were placed on ice for 30 minutes and vortexed every 10 minutes. Lysates were frozen and stored at −80° C. prior to further processing.

Lysates were placed in a QIAshredder tube (QIAGEN, cat#79656) and spun down 30 sec, top speed (13200 rpm) in an Eppendorf benchtop centrifuge (Model 5415 R). The lysate was then transferred to a 1.5 mL clear Eppendorf tube and spin down 10 min at top speed. The supernatent was collected without disturbing the cell debris pellet. The supernatent was dry ice frozen and stored at −80° C. prior to analysis.

The protein concentration in supernatent was measured using BCA assay and the expected protein yield was about 0.5-5 μg/μL, or 125-1250 μg total. Approximately ≥10 μg protein per lane was loaded for western blotting (IRF4, IKZF3, etc.) using antibodies against the human proteins.

Processing PBMCs for mRNA Analysis

The PBMCs were lysed in 0.35 mL of RLT buffer (Qiagen cat #79216) and vortexed to homogeneity. Lysates were frozen and stored at −20° C. until further processing. Lysates were thawed at room temperature. RNA was isolated using Qiagen Rneasy Mini Kit (cat #74104) manual or using QIAcube. RNA concentrations were obtained with Nanodrop. RNA needed or cDNA preparation was about 500-1000 ng of RNA in a total volume of about 38.5 μL.

cDNA preparation was done by first preparing a master mix solution of Tagman Reverse Transcription Reagents (Applied Biosys #N808-0234). 61.5 μL of master mix was added to the 38.5 μL RNA (total volume=100 μL). The RNA/master mix was put immediately into the thermal cycler.

Preparation of qRT-PCR plate IRF4, BLIMP-1, BCL-6, IgJ etc. using the Cynomolgus cDNA cDNA and cynomolgus sequence-specific primers was performed by first preparing the Tagman Master mix, water and Tagman gene expression assay. 5 μL of a cDNA sample was added in triplicate in plate. 45 μL of master mix was added. The plate was spun and put into the RT-PCR for a run.

7.1.7 PD Sampling in Compound B Non-Human Primate Dose Regimen Study

Figure 4:
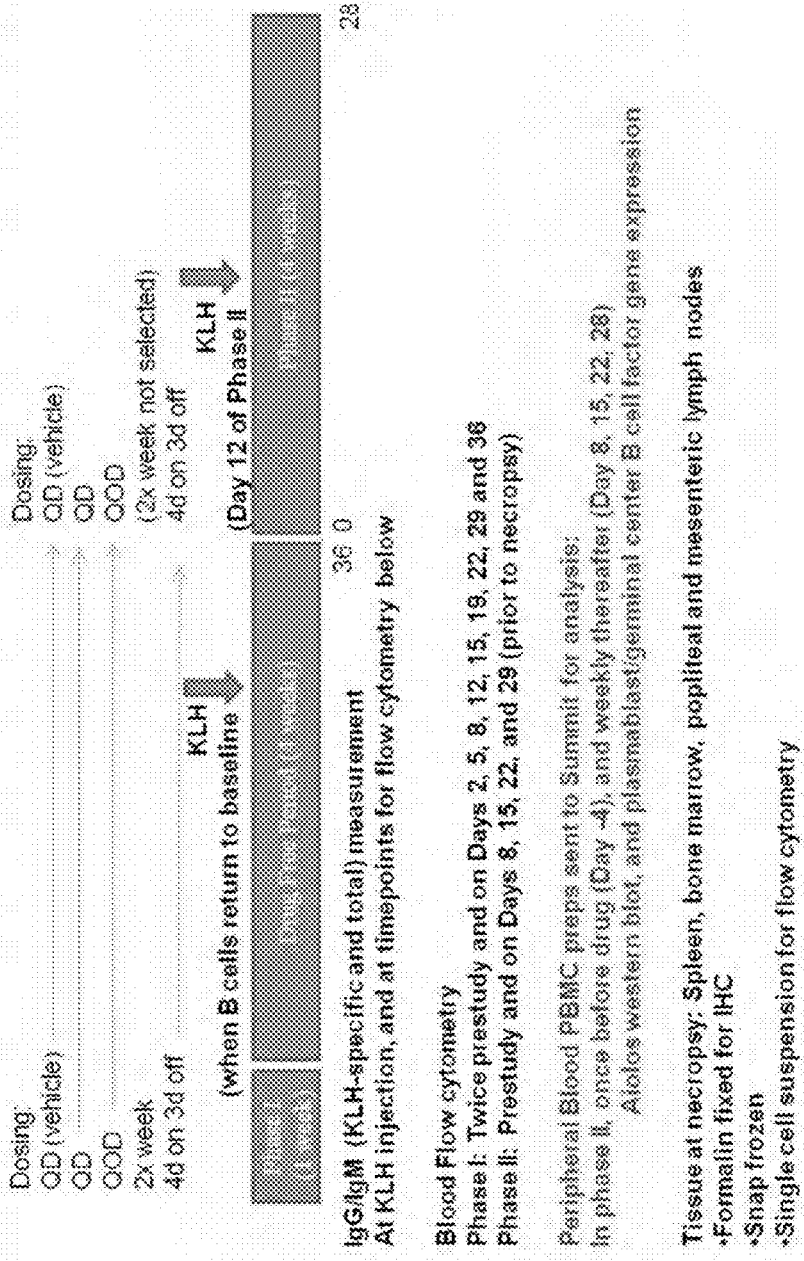
FIG. 4 shows PD sampling in Compound B non human primate dose regimen study.

As depicted in FIG. 4, the study in Cynomolgus monkeys was divided in two phases: Phase I (7 days of oral doing with test article, Compound B hydrochloride) followed by 28 day test article free period and finally Phase II (28 days of oral dosing with test article). The objective of the Phase I of this study was to determine the onset and duration of pharmacodynamic effect of Compound B. The objective of the Phase II of this study was to explore the relationship the pharmacodynamic effects and safety/tolerability of Compound B. In addition, the toxicokinetic characteristics of Compound B were determined. Doses of Compound B tested were 0.75 mg/kg QD, every other day, or 4 days on, 3 days off. The test and control articles were administered to the appropriate animals by gavage from Days 1 to 7 for Phase I and from Days 1 to 28 in Phase II following dose regimens as described above. Phase I and Phase II were separated by at least a 28 day dose free session. The dose volume for each animal was based on the most recent body weight measurement. A naso/orogastric tube was inserted through a nostril (nasogastric) or through the mouth (orogastric) and advanced into the lower esophagus to the stomach. The animals were temporarily restrained (e.g., manually) for dose administration, and were not sedated. Disposable sterile syringes and naso/orogastric tubes were used for each animal/dose. Each dose were followed by a tap water flush of approximately 5 mL. The dosing formulations were stirred continuously during dose administration. Peripheral blood mononuclear cell subsets analyzed by flow cytometry were: CD45$^+$/CD3$^+$/CD20$^+$/CD16$^+$, CD45$^+$/CD20$^+$, CD45$^+$/CD3$^+$, CD45$^+$/CD3$^+$/CD4$^+$, CD45$^+$/CD3$^+$/CD8$^+$, CD45$^+$/CD3$^-$/CD16$^+$, CD45$^+$/CD3$^-$/CD14$^+$. Anti-KLH antibody titers were assayed by ELISA (FIG. 5).

The protein levels of Aiolos/IKZF3 were measured in the peripheral blood mononuclear cells as follows. Cynomolgus (*M. fascicularis*) blood yielded approximately 10 million ($10 \times 10^6$) mononuclear cells (PBMC) per 2.5 ml whole blood (according to protocol by Non Human Primate Reagent Source, Boston). After the cyno PBMC isolation, each sample was divided into two portions: $7 \times 10^6$ cells for protein analysis and $3 \times 10^6$ cells for mRNA analysis. All steps were done on ice, all centrifugation in a 4° C. refrigerated centrifuge. RIPA lysis buffer (Pierce, cat#89900) was prepared by adding 10 µL proteinase inhibitors (Pierce, cat#78443) to 1 mL of RIPA buffer. The PBMC was washed once in ice-cold phosphate buffered saline (PBS). Lysis buffer (use 0.25 mL RIPA lysis buffer per $7 \times 10^6$ PBMC) was added. The tube was placed on ice for 30 minutes, vortexed every 10 min. The lysate was frozen and store at −80° C. until analysis. The lysate was placed into a QIAshredder tube (QIAGEN, cat#79656) and spun down 30 sec at top speed (13200 rpm) in an Eppendorf benchtop centrifuge (Model 5415 R). The lysate was transferred to a 1.5 mL clear Eppendorf tube and spun down 10 min at top speed (QIAshredder collection tubes are milky in color and hard to see the cell debris pellet, hence the transfer to the new tubes). The supernatant was collected without disturbing cell debris pellet (RIPA reagent enables the extraction of membrane, nuclear and cytoplasmic proteins that will remain in the supernatant). The protein lysate was frozen on dry ice and stored at −80° C. until analysis. The protein concentration was measured using BCA assay. The protein yield was expected to be 0.5-5 µg/µL, or 125-1250 µg total. ≥10 µg protein was loaded per lane for western for IKZF3/Aiolos using antibodies against the human proteins.

7.1.8 U266, DF15 B and T Cell Western Blots

U266 cells were obtained from ATCC (American Type Culture Collection, Manassas, Va., USA). DF15 cells were obtained from John Shaughnessy (University of Arkansas, Little Rock, Ark., USA). CD19+ B cells were purchased from HemaCare BioResearch Products (Van Nuys, Calif.). Cells were grown in RPMI-1640 medium (Cellgro, Manassas, Va.) containing 10% (V/V) heat-inactivated fetal bovine serum (Gibco, Grand Island, N.Y., USA) supplemented with 2 mM glutamine. U266 and DF15 cells ($8 \times 10^5$/well) or B cells ($4 \times 10^5$ cells/well) were plated into 6-well plates and either lenalidomide or pomalidomide treated for various times and concentrations. Primary T cells were isolated from human leukocytes (Blood Center of New Jersey, East Orange, N.J.) by centrifugation through FICOLL® centrifugation medium following the ROSETETTESEP™ protocol (Stem Cell Technologies, Vancouver, Canada). Purified T cells were stimulated with anti-CD3 Antibody (Ebioscience, San Diego, Calif.) and treated with either lenalidomide or pomalidomide for various times and concentrations. Dexamethasone (Sigma, St. Louis, Mo.), melphalan (Sigma, St. Louis, Mo.) and bortezomib (Selleck Chemicals, Houston, Tex.) treated was for 6 hours. The final DMSO concentration is 0.1%. Cells were pre-treated with 10 µM MG-132 (Calbiochem Biochemicals, Billerica, Mass.) for 30 minutes prior to drug addition. Cells were harvested, washed in PBS and cell lysates separated on SDS-PAGE gels (Bio-Rad, Hercules, Calif.). Membranes were immunoblotted with anti-Aiolos (Santa Cruz Biotechnology, Dallas, Tex.), anti-Ikaros (Millipore, Billerica, Mass.) and anti-Actin (Sigma, St. Louis, Mo.; or LI-COR Biosciences, Lincoln, Nebr.) and secondary antibodies (LI-COR Biosciences, Lincoln, Nebr.). The blots were analyzed on ODESSEY® imager (LI-COR Biosciences, Lincoln, Nebr.).

7.1.9 Cycloheximide Experiment Methods

Two and a half million U266 multiple myeloma cells (ATCC) were plated per well in 6-well dishes, incubated with 100 mg/mL cycloheximide (Sigma, C4859), and treated with either DMSO, 10 µM lenalidomide or 1 µM pomalidomide for 0, 1.5, 3 or 6 hours. Cell lysates were separated on a 10% TGX SDS-PAGE gel (Bio-Rad) and blotted for Aiolos (Santa Cruz, sc-10198), Ikaros (Millipore, ABD16) and Actin (Sigma, AC15).

7.1.10 CRBN and Aiolos siRNA Transfection in T Cells

Primary T cells were isolated from human leukocytes (Blood Center of New Jersey, East Orange, N.J.) by centrifugation through FICOLL® centrifugation medium following the ROSETETTESEP™ protocol (Stem Cell Technologies, Vancouver, Canada). Purified T cells were treated with 1 µg/mL PHA-L (Sigma, St. Louis, Mo.) at 37° C. for 24 hours then transfected with either siCRBN or siAiolos (Invitrogen) (200 nM siRNA/100 µL T buffer/$8 \times 10^6$ cells/shot$\times$5 shots) using NEON® Transfection System (Invitrogen, Grand Island, N.Y.) with program 2100 voltage+15 width+2 pulse. Low GC content siRNA (Invitrogen, Grand Island, N.Y.) was transfected as negative control. Transfected cells were pooled and cultured in OKT3 (3 µg/mL, eBioscience, San Diego, Calif.) coated 10 cm dish with 20 ml RPMI containing 10% FBS at 37° C. for 24 hours. Cells were collected for measuring CRBN or Aiolos knockdown efficiency by western blot (anti-Aiolos: Santa Cruz, sc-10198, lot.C-0212) and qRT-PCR (Applied Biosystem, gene expression CRBN Hs00372271_ml; IKZF3 ID#: Hs00232635_ml). Cells were also collected for measuring IL-2 RNA by qRT-PCR (Applied Biosystem, gene expression ID#: Hs00174114_ml). For Aiolos expression in the siCRBN transfected cells, the remaining siCRBN transfected cells were seeded on OKT3 prebound (3 µg/mL) 12-well TC plates at $15 \times 10^6$ cells/3 mL/well and treated with DMSO or drug at 37° C. for 24 hours then harvested for western analysis. Aiolos and Ikaros protein expression was determined by immunoblot analysis using antibodies against Aiolos (Santa Cruz, Dallas, Tex.) and Ikaros (Millipore, Billerica, Mass.). For IL-2 production in the siAiolos transfected cells, the remaining transfected cells were seeded on OKT3 prebound (3 µg/mL) 96-well TC plates at $2 \times 10^6$ cells per well and treated with DMSO or drug at 37° C. for 2 days. Supernatants were harvested and IL-2 protein detected by ELISA (Thermo Scientific, Lafayette, Colo.).

7.1.11 H929 e211 Xenograft Methods

Female SCID mice (Fox Chase SCID®, C.B-17/Icr-Prkd-cscid, Charles River) (Wilmington, Mass.) were injected subcutaneously in the right flank with total of $1 \times 10^7$ NCI-H929 tumor cells in 50% matrigel (BD Biosciences). Once the tumors reached an average size of 100-150 mg, 10 mice in each group were treated with either vehicle (0.5% carboxymethyl cellulose: 0.25% Tween 80 in deionized $H_2O$), or indicated doses of oral lenalidomide daily for 19 days. Mice were monitored daily for health status as well as tumor growth. Tumors of all mice were measured with a digital caliper, and volumes were calculated with the following formula: tumor volume $(mm^3)$=length (mm)×width $(mm)^2$. In a satellite group, mice (3 per group) were treated for 7 days with either vehicle or indicated doses of oral daily lenalidomide the tumors were excised and snap frozen for immunohistochemical analysis.

7.1.12 Immunohistochemistry

Four micron thick formalin fixed paraffin-embedded xenograft tumour sections were stained with antibodies to CRBN (rabbit monoclonal Celgene CRBN65), Aiolos (rabbit polyclonal antibody; Santa Cruz, Dallas, Tex.), and Ikaros (rabbit polyclonal antibody; Millipore, Billerica, Mass.) using the Bond-Max automated slide strainer (Leica Microsystems, Buffalo Grove, Ill.) and the associated Bond Polymer Refine Detection Kit. Antigen retrieval was performed with Epitope Retrieval 2 (pH 9.0) for 20 min at 100° C. on the instrument. The slides were blocked for endogenous peroxidase activity with Peroxide Block for 5 min at room temperature. Sections were then incubated with primary antibodies to CRBN at 1:4000, Aiolos at 1:1000, and Ikaros at 1:1000 for 15 minutes at room temperature. Since these primary antibodies are rabbit host species, the Post Primary step was removed from the protocol to avoid cross-reactivity to the mouse xenograft components. Negative control slides received Bond Primary Antibody Diluent instead of primary antibody. Horseradish peroxidase (HRP) labelled Polymer was applied at the instrument's default conditions and diaminobenzidine tetrahydrochloride (DAB) was used as the enzyme substrate to visualize specific antibody localization. Slides were counterstained with hematoxylin. IHC staining intensity was scored on a scale of 0-3 (0=negative, 1=weak, 2=intermediate, 3=strong). Range of cells with specific immunoreactivity (<1%=0, 1-25%=1, 26-75%=2, and >75%=3) were recorded. Total score of the immunoreactivity intensity was calculated as product of intensity and range of positive cells.

7.1.13 Aiolos Inhibition by Cohort

Cancer patients were administered Compound A at doses of 0.5 mg, 1 mg, 1.5 mg, 2 mg, 2.5 mg, 3 or 3.5 mg. Blood samples were drawn immediately prior to dosing and 1.5 hr and 5 hr post single dose of Compound A. Peripheral blood mononuclear cells were FICOLL®-isolated from whole blood samples and viably frozen in DMSO. The cells were washed twice with 2 mL of cold phosphate buffer saline (PBS), then permeabilized by adding 2 mL of cold BD CYTOFIX/CYTOPERM™ buffer and incubated on ice for 15 minutes. The cells were centrifuged then washed twice with BD PERM/WASH™ buffer, then resuspended in 40 µl of BD PERM/WASH™ buffer. Cells were stained with anti-CD3 or anti-CD19 antibody, and 20 µl of anti-Aiolos Ab (Santa Cruz Santa Cruz, rabbit polyclonal IgG, cat#sc-101982 at 1:200 dilution with staining buffer), or 20 µL of appropriate isotype controls to cells. Cells were mixed thoroughly and incubated at room temperature for 30 minutes in the dark, washed once with BD perm/wash buffer, then resuspended in 80 µA of BD PERM/WASH™ buffer, and 20 µL of secondary antibody was added before analysis on a flow cytometer.

7.1.14 Drug Treatment in T Cells

Primary T cells from up to 3 donors were isolated from human leukocytes (Blood Center of New Jersey, East Orange, N.J.) by centrifugation through FICOLL® following the ROSETETTESEP™ protocol (Stem Cell Technologies, Vancouver, Canada). Purified T cells were stimulated with anti-CD3 Antibody (Ebioscience, San Diego, Calif.), drug treated for six hours, harvested and Aiolos and Ikaros protein expression was determined by immunoblot analysis using antibodies against Aiolos (Santa Cruz, Dallas, Tex.) and Ikaros (Millipore, Billerica, Mass.) with our without blocking peptide.

7.1.15 Aiolos Protein Degradation in Jurkat Cells

Jurkat cells were transfected with wildtype full length Aiolos and different lysine mutated full length Aiolos DNA (Origene, 5 µg DNA/100 µL R buffer/$2 \times 10^6$ cells/shot) using Neon Transfection System (Invitrogen, Grand Island, N.Y.) with program 1350 voltage+10 width+3 pulse. GFP control DNA (Lonza) was also transfected. Transfected cells were cultured in 24-well plate with 1 mL RPMI+10% FBS at 37° C. for 6 hrs and then treated with DMSO or drug for another 48 hrs, Drug treated cells were collected for measuring Aiolos and Ikaros protein expression by western blot with antibodies against Aiolos (Santa Cruz, Dallas, Tex.) and Ikaros (Millipore, Billerica, Mass.).

7.1.16 Aiolos Flow Cytometry in B and T Cells

Healthy volunteers were administered placebo (n=10) or Compound B at doses of 0.03 mg, 0.1 mg, 0.3 mg, 1 mg, or 2 mg (N=6 each). Blood samples were drawn prior to dosing, or 3 hr, 12 hr, and 24 hr after dosing. 1. Blood samples were lysed and fixed immediately by mixing 1 volume of blood with 20 volumes of 1× Lyse/Fix buffer (BD Biosciences, cat#558049) and mixing thoroughly by inverting the tube several times. This sample mix was incubated in a 37° C. water bath for 10 minutes, and the cells were pelleted by centrifugation at 800×g for 5 minutes to remove the supernatant by aspiration. The cells were washed twice with 2 mL of cold phosphate buffer saline (PBS), then permeabilized by adding 2 mL of cold BD Cytofix/cytoperm buffer and incubated on ice for 15 minutes. The cells were centrifuged then washed twice with BD perm/wash buffer, then resuspended in 40 µL of BD perm/wash buffer. Cells were stained with anti-CD3 or anti-CD19 antibody, and 20 µL of anti-Aiolos Ab (Santa Cruz Santa Cruz, rabbit polyclonal IgG, cat#sc-101982 at 1:200 dilution with staining buffer), or 20 µL of appropriate isotype controls to cells. Cells were mixed thoroughly and incubated at room temperature for 30 minutes in the dark, washed once with BD perm/wash buffer, then resuspended in 80 µL of BD perm/wash buffer, and 20 µL of secondary antibody was added before analysis on a flow cytometer.

7.1.17 SimpleWestern Electropherograms from Normal Human CD19+ B Cells

Human B cells were isolated from 3 donors of whole bloods from the New Jersey Blood Center using B cell isolation kits from StemCell Technologies. IKZF family proteins were quantified using the automated capillary-based SimpleWestern System Sally (ProteinSimple). 100 ng of cell lysate protein or serial dilutions of recombinant proteins were mixed in reducing buffer with fluorescent Molecular Weight (MW) standards. After these samples were heated to 95° C. for 5 min, samples were loaded into each capillary tubes and proteins were separated based on MW sizes through stacking and separation matrices for 40 minutes at 250 Volts. Proteins were then immobilized to capillary walls using optimal photoactivated capture chemistry. Following protein immobilization, capillaries were incubated with a blocking reagent for 23 min and target proteins were probed with a specific primary antibody and horseradish peroxidase-conjugated anti-rabbit secondary antibody (ProteinSimple). A mixture of luminol and peroxide (ProteinSimple) was added, the resulting chemiluminescent signal was captured by a CCD camera, and the signal intensities were quantified and analyzed using Compass Software for Sally (ProteinSimple). The Ikaros family proteins in each sample were then calculated based on standard curve of human recombinant proteins. B-Actin was also used as an internal normalization control.

7.1.18 Procedure for mRNA Analysis

PBMCs were isolated from whole bloods of normal volunteers and patients with indicated inflammation diseases (Conversant Bio, Huntsville, Ala.). Cells were then cultured for 24 hours in RPMI-1640 medium supplemented with 5% autologous serum and antibiotics. Following incubation, $1 \times 10^6$ cells were collected, washed with cold PBS and lysed with 350 µL RLT buffer (Qiagen). Cell lysates were transferred to barcoded tubes for RNA QC and gene expression analysis with microarray. Affymetrix HG-U133 Plus 2.0 array experiments were performed at The Covance Genomics Laboratory (Covance).

7.1.19 Procedure for Cynomolgus PBMC Samples 32 cynomolgus monkeys were randomly divided into 4 groups. Each group had 4 female and 4 male monkeys (n=8). The 3 groups of monkeys were orally administered with Compound B at the dose of 0.04, 0.15, 0.75 mg/kg respectively. The left group was used as the vehicle control (0.5% carboxymethyl cellulose: 0.25% Tween 80 in deionised $H_2O$). Following dosing with drugs for 1 month, whole bloods from each monkey were sampled and PBMCs isolated. Ikaros levels in PBMCs were quantified using the automated capillary-based SimpleWestern System Sally (ProteinSimple) as previously mentioned. Analyses for multiple group comparisons were performed with 1-way analysis of variance, followed by the Dunnett post-test, using GraphPad Prism® version 5.01 (GraphPad Software, Inc., La Jolla, Calif., USA). A value of $P<0.05$ was considered significant in all analyses.

7.1.20 B-CLL Cell Culture Materials

Human primary B-CLL cells viably frozen from patient samples were obtained from AllCells (Emeryville, Calif., USA) and maintained in Roswell Park Memorial Institute (RPMI)-1640 medium with 10% fetal bovine serum (FBS) (Invitrogen, Carlsbad, Calif.). CD40L expressing fibroblasts (gift from Angela Piperno, Rockefeller University, NY, N.Y.) were maintained in DMEM medium supplied with 20% FBS. Prior to co-cultures CD40L fibroblasts were pre-treated for 3 hours with 10 µg/mL Mytomicin C followed by a wash with PBS and Accutase dissociation. Cells were then re-plated at a density of $6 \times 10^5$ cells per well (24 well per plate format) and grown overnight to allow formation of monolayer. Defrosted viable primary B-CLL patient cells were pre-stained with CFSE reagent (Vibrant CFDA SE Cell Tracer Kit, Invitrogen, Carlsbad, Calif., USA) according to a manufacturer's supplied protocol and plated at $0.8-1 \times 10^6$ cells per well on the pre-formed monolayer of CD40L fibroblasts in RPMI 1640 medium supplemented with 10% FBS, 5 ng/mL rh-IL4 and 10 ng/mL rh-IL10 (Peprotech, USA). For long term cultures, half of the culture media was renewed every three days. Alternatively, for other assays, B-CLL cells were co-cultured on CD40L without being pre-stained.

7.2 Effects on Aiolos Expression

Figure 1:
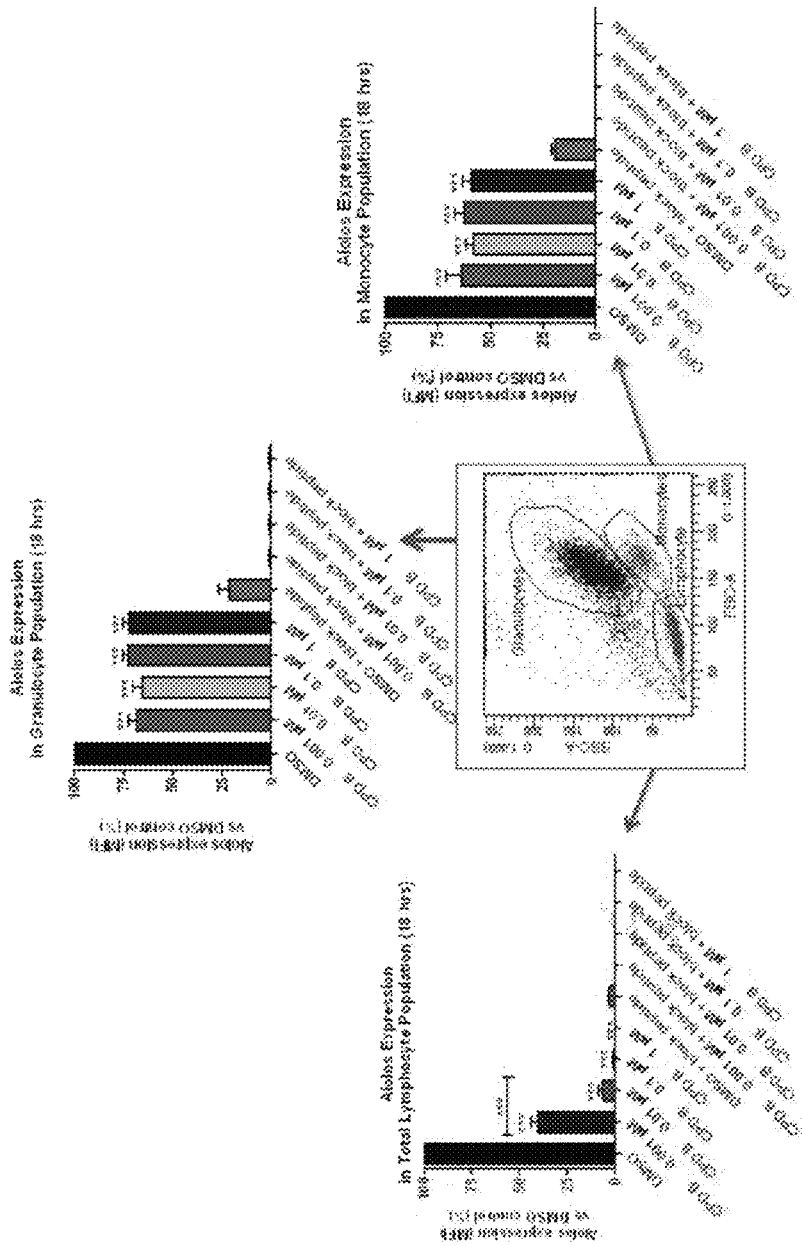
FIG. 1 shows the effect of Compound B in the inhibition of Aiolos expression in lymphocyte (Left panel) granulocyte (Top panel) and monocyte (Right panel) populations presented as a percentage of DMSO control, n=3.
Figure 2:
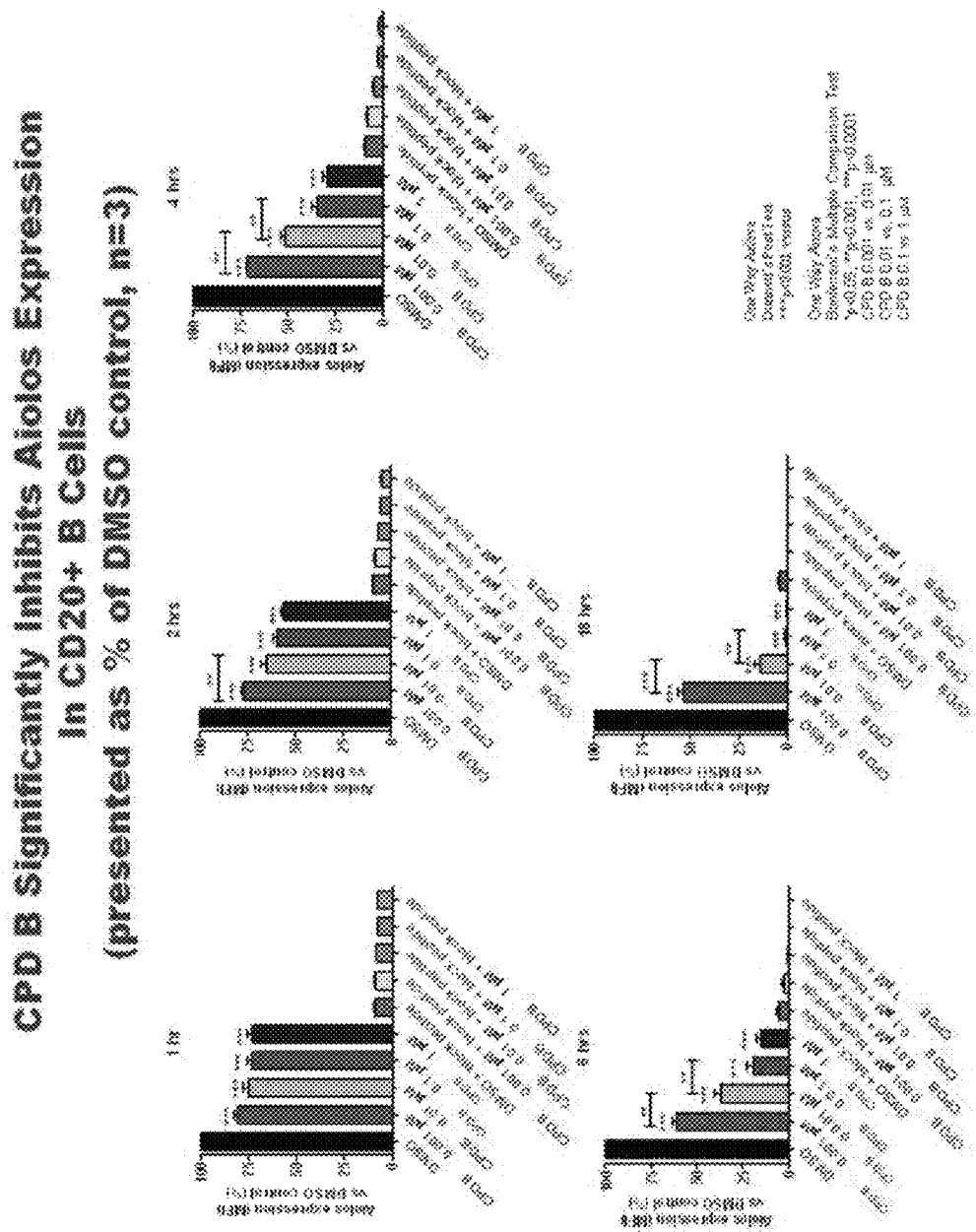
FIG. 2 shows Compound B significantly inhibiting Aiolos expression in CD20+ B cells as a percentage of DMSO control, n=3.
Figure 3:
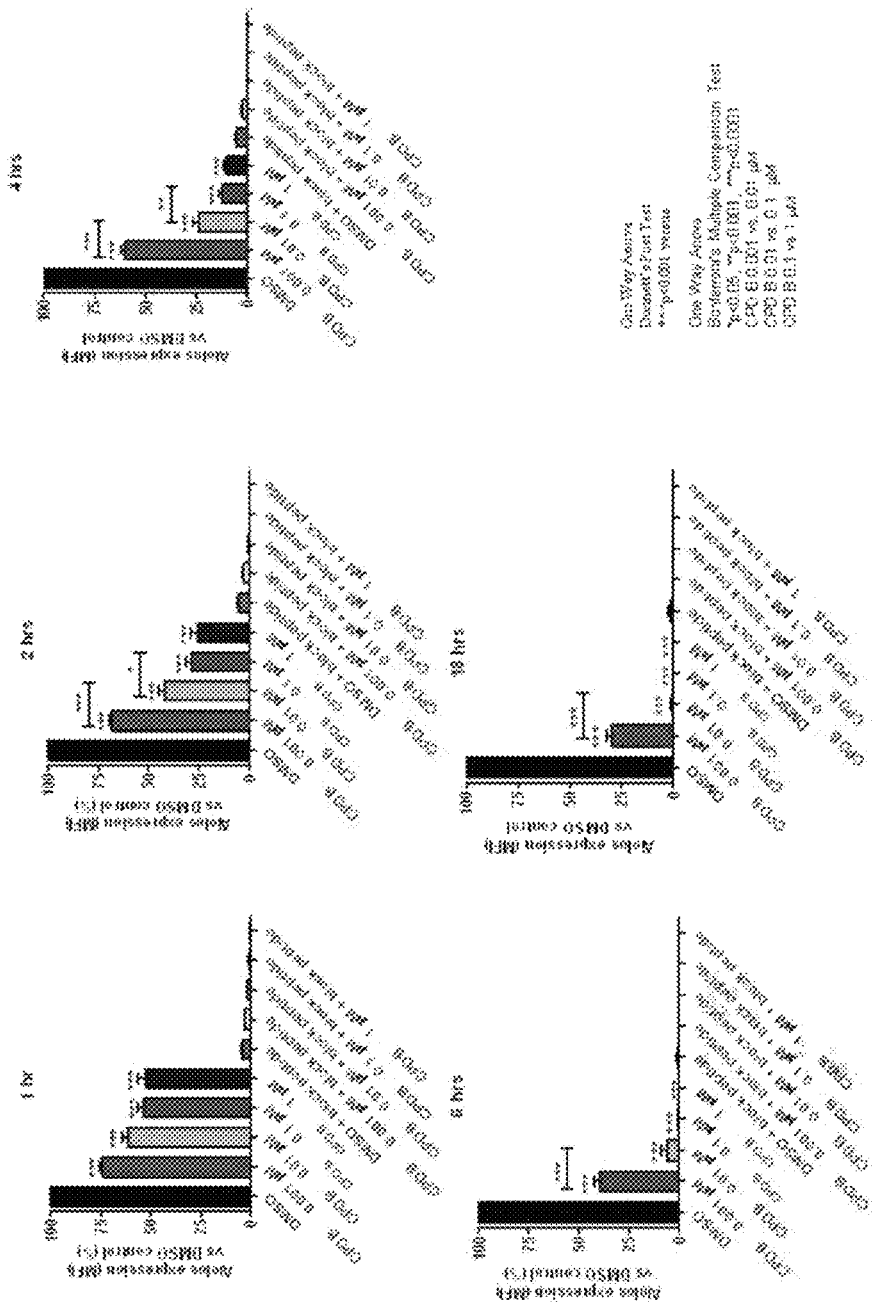
FIG. 3 shows Compound B significantly inhibiting Aiolos expression in CD3+ T cells as a percentage of DMSO control, n=3.

The effect of Compound B in the inhibition of Aiolos expression in lymphocyte (left panel) granulocyte (top panel) and monocyte (right panel) is shown in FIG. 1. As shown in FIGS. 2 and 3, respectively, Compound B significantly inhibited Aiolos expression in CD20+ B cells and CD3+ T cells. As shown in FIGS. 51 A and B, while some inhibition of Aiolos has been observed in CD19+ B cells and CD3+ T cells upon treatment by Compound B, it was found that doses greater than 0.3 mg of Compound B inhibited Aiolos expression at significant levels.

Western blot analysis of human whole blood, treated with the compounds as specified at 250 nM for 18 hours, is shown in FIG. 7, and the same for Mauritius Monkey PMBCs is shown in FIG. 8. As show in FIG. 8, Compound B, at 18 hours after the treatment, inhibited the expression of Aiolos.

Studies on Cyno Monkeys using Compound B were conducted according to the treatment regimen summarized in FIG. 6. Briefly, four treatment groups were assigned, each of which received the treatment by Compound B according to the dosing schedule and doses specified in FIG. 6. The results from each of the groups are shown in FIGS. 9-16, which show that effects of Compound B on Aiolos expression may vary according to the dosing regimen, but Compound B generally inhibits the expression of Aiolos.

The effects of Compounds A and B, lenalidomide ("len") and pomalidomide ("pom") on Aiolos expression were also assessed. As shown in FIG. 17, Compound A was shown to inhibit the expression of Aiolos in the absence of a proteasome inhibitor, but little inhibition was observed when a proteasome inhibitor was present. As shown in FIG. 18, all of len, pom, Compound A and Compound B showed inhibitory effect on Aiolos expression. It appeared that the inhibitory effect correlates with compound's anti-proliferative activity in Myeloma cells. As shown in FIG. 43 A-D, Aiolos is a negative regulator of IL-2 in T cells and silencing Aiolos mimics IMiD treatment. As shown in FIG. 50 A-D, lenalidomide, pomalidomide, Compound A, and Compound B showed an inhibitory effect on Aiolos expression in primary T cells.

Studies on Aiolos expression were conducted in various leukemia cells. It was found that the level of Aiolos is higher in B cells obtained from CLL patients than that in B cells obtained from healthy subjects (FIG. 22). It was also shown that len, pom, Compound A and Compound B inhibit Aiolos expression in B cells obtained from CLL patients as well as healthy subjects (FIG. 22). Similar effects were also shown in lymphoma cells MCL and DLBCL (FIG. 23). Notably, it was shown that little or no inhibition of Aiolos expression occurs in cells with low cereblon expression (FIG. 19), and similarly, loss of cereblon was shown to prevent the down-regulation of Aiolos expression (FIG. 20), implying the involvement of cereblon in this process. Finally, it was shown that knock-down of Aiolos induces p21 expression, decreases IRF4, and decreases number of cells in S phase (FIGS. 21 and 24).

7.3 Identification of Cereblon-Associated Proteins

Mass spectrometry of ubiquitylated proteins (Ubiscan™): Cell Signaling Technology's UbiScan™ proteomics platform was used to identify and quantify differences in ubiquitination in primary human T cells untreated (Treatment 1) or treated with Treatment 2 or Treatment 3, and in MM cell lines treated with immunomodulatory compounds in the presence or absence of the proteasome inhibitor MG132. The UbiScan™ method combines the isolation of ubiquitinated peptides from protease digested protein extracts using CST's proprietary immunoaffinity purification method with the identification and quantitation of peptides by liquid chromatography, tandem mass spectrometry (LC-MS/MS). The quantification of ubiquitination is based on the abundance of the ubiquitinated peptides recovered by antibody immunoprecipitation. The abundance or intensity information for each ubiquitinated peptide is based on the peak height of that peptide measured in the MS1 channel. The confidence in the calculated fold change is dependent on a number of factors, an important one being the intensity or peak height of the ubiquitinated peptide. Samples were analyzed by LC-MS/MS on an ORBITRAP VELOS™ mass spectrometer. Chromatographic peak apex intensities of peptide ions in each sample were derived from their corresponding extracted ion chromatograms. Label-free quantitation was performed by comparing peak intensities of the same peptide ion in each sample to generate their corresponding fold-changes. Qualitative data assessment was primarily an automated process. Peptide assignments that satisfied specific scoring criteria from the SORCERER platform and fell within established experimental parameters were retained in the final results of the study. Further confidence in the assignment was obtained if the particular peptide contained multiple lines of evidence from the redundant SORCERER resulted to support the same site identification, such as overlapping sequences due to incomplete protease digestion, the presence of a methionine residue in the reduced and/or oxidized form, or the presence of the ubiquitinated peptide in multiple charge states. Peptides that have been independently identified multiple times have a greater likelihood of being correctly assigned compared to peptides with a count of 1. However, those peptide assignments with low counts should also be considered confidently identified if they have sufficient experimental evidence as indicated by their corresponding SORCERER scores and data quality metrics (XCorr, DeltaCn, PP Probability, and mass error). As shown in FIG. 38, it was found that pomalidomide and lenalidomide enhance the ubiquitination of Aiolos peptide containing lysine 203. The result shows that lenalidomide and pomalidomide promote the degradation of Aiolos.

7.4 Identification of Compound Binding Proteins Using Covalent Cross-Linking with Reactive Pharmacophores (Caprotec)

Lenalidomide and optionally one (1) precursor molecule nitro-lenalidomide were synthesized using three (3) different linkers and one (1) capture scaffold to synthesize six (6) Capture Compounds™ in total. The capture compounds might contain a biotin or a fluorescence residue as pull-out function. This required approximately 24 synthetic steps. 4 steps were of medium risk to be optimized. 20 steps were routine transformation and at low risk to be optimized. All Capture Compounds were purified and analyzed to confirm structural identity, purity and stability. The photochemistry of the Capture Compounds were critically investigated. Multiple myeloma cell line lysates were incubated with the Capture Compounds using the optimized capture conditions to perform the profiling of all Capture Compounds from Step 3 within the specified biological material. Selective interactions were confirmed by appropriate control and competition experiments employing lenalidomide and possibly inactive analogues provided in sufficient amounts. The number of MS samples in this step was approximately 100. Step 6, Step 4 and Step 5 were accompanied by mass spectrometry analysis followed by statistical and quantitative LC-MSn data analysis of the captured proteins. On this basis the optimization of the assay in Step 4 was judged and list of all proteins that specifically interact with the small molecule in Step 5 will be generated.

7.5 Effects of Compound A on Endogenous Aiolos in Breast Cancer Cells

Cell lines (AU565, ZR 75-1, BT-474, EFM-192A, HCC1954, HCC70, MB436 and BT549) were maintained using standard cell culture techniques. For endogenous Aiolos expression, cells were seeded in a 6 well plate at $0.5 \times 10^6$ cells per well in a 3 mL volume of media. Cells were allowed to adhere to the plate overnight. Cells were exposed to 0, 1, and 10 µM Compound A for the specified amounts of time.

In some experiments, cell lines were transfected with an Aiolos overexpression vector using Lipofectamine reagent in a batch method. Cells were seeded in a 12 well plate at $1 \times 10^5$ cells in a 3 mL volume per well. Where specified, cells were pretreated with MG132 at 10 uM for 1 hour, or DMSO was added as a control. Following the pretreatment, Compound A was added directly to the cell culture media at the specified concentration.

Cells were harvested and lysed in Pierce #89900 Ripa buffer containing 2× protease inhibitor cocktail from Pierce #78442. The lysate was applied to a QiaShredder to remove DNA. Total protein yield was measured using BioRad DC protein determination kit (Cat#500-0112). Lysates were stored at −80° C. until use. Samples were applied to BioRad Criterion PreCast gels, 10% (Bio-Rad#345-0010) and transferred to Bio-Rad Nitrocellulose/Filter Paper Sandwiches (#162-0233) for western blot analysis.

As shown in FIG. 25, it was found that, at 24 hours after the treatment, Compound A reduced the levels of Aiolos (a band appearing around 60 kD) in both ZR 75-1 and AU565 cell lines. In certain experiments, flag-Aiolos-myc fusion protein was overexpressed in AU565 cells, and the cells were treated with Compound A. In such cases, it was found that western blot analysis using anti-myc antibody provided one Aiolos band around 65 KD, while the same analysis anti-flag antibody provided multiple bands (FIG. 26). Further, it was found that the reduction of overexpressed Aiolos begins to show at about 5 hours after the treatment by Compound A (FIG. 27), and inhibition of Aiolos by Compound A was rescued by the addition of proteasome inhibitor MG-132 (FIGS. 26 and 27). Finally, it was shown that endogenous Aiolos is inhibited by Compound A in Her2+ cells (AU565, BT-474, EFM-192A and HCC1954), but not in triple negative cells (HCC70, MB436 and BT549). These results suggest that Aiolos is inhibited by Compound A, and thus, can be used as a biomarker for the treatment by Compound A.

7.6 Expression of Aiolos in Lymphoma Cells

Xenografts from lymphoma OCI-LY10 cells were used for the following experiments. Immunohistochemistry was performed on the Bond-Max automated slide stainer (Leica Microsystems) using the associated Bond Polymer Refine Detection Kit. Four micron thick FFPE sections were deparaffinized on the instrument. Antigen retrieval was performed with Epitope Retrieval 2 (pH 9.0) for 20 minutes at 100° C. The slides were blocked for endogenous peroxidase activity with Peroxide Block for 5 minutes at room temperature. Sections were then incubated with rabbit polyclonal antibody to Aiolos (Santa Cruz, sc-101982) at a 1/1000 dilution for 15 minutes at room temperature, followed by incubation with HRP labeled Polymer for 8 minutes at room temperature. Enzymatic detection of anti-Aiolos antibody was accomplished with hydrogen peroxide substrate and diaminobenzidine tetrahydrochloride (DAB) chromogen at room temperature for 10 minutes. Slides were counterstained with Hematoxylin for 5 minutes at room temperature.

As shown in FIGS. 29-32, it shown that all of lenalidomide (FIG. 29), Compound A (FIG. 30), R-isomer of Compound A (FIG. 31), and S-isomer of Compound A (FIG. 32)

inhibited the expression of Aiolos in lymphoma cells. Approximate Aiolos levels in compound treated tumors were: S-isomer of Compound A<Compound A<R-isomer of Compound A<lenalidomide, but tumors treated with any of these compounds showed lower Aiolos levels than vehicle or vincristine treated tumors. The results suggest that Aiolos expression can be a good biomarker in connection with the treatment by any of the tested compounds.

7.7 Effects of Compound A or Compound B on Aiolos Expression in Lymphocytes 7.7.1 Effects in Whole Blood as Determined by FACS Assay Pre-weighed test compound was dissolved in 100% DMSO to make 100 mM or 10 mM stock concentrations. The compound in 100% DMSO was diluted to 10 mM, 1 mM, 0.1 mM, 0.01 mM, 0.001 mM stock concentrations as appropriate. Compounds were directly added to heparinized human whole blood (1:1000 dilution) for final concentrations of 10 µM, 1 µM, or 0.1 µM as appropriate. Ten (10) ml of whole blood was transferred to a 50 mL conical tube and treated with test compound. The final DMSO concentration was 0.1%. The blood was incubated for 1.5 or 5 hours at 37° C., 5% $CO_2$. After each time point, the blood was lysed/fixed, permeabilized, washed and stained with Aiolos as described below.

BD Lyse/Fix Buffer was diluted 5× with distilled (or deionized) water. The Lyse/Fix buffer was pre-warmed in a 37° C. water bath for 10 minutes before use. The cells were lyzed and fixed immediately by mixing 1 volume of whole blood with 20 volumes of 1× Lyse/Fix buffer (for the 1 mL of blood+compound, add 20 mL of 1× Lyse/Fix buffer) and mixed thoroughly by inverting the tube several times. The cell lyse/fix and blood mixture was incubated in a 37° C. water bath for 10 minutes. Cells were pelleted by centrifugation at 500×g for 5 minutes and removed the supernatant by aspiration. Cells were suspended with 5 mL of cold PBS, and then pelleted by centrifugation at 500×g for 5 minutes, and the supernatant was aspirated off. Two hundred (200) µL of PBS was added to cells. Cells were transferred to polystyrene U-bottom 96-well plates (BD, Cat. No. 353910) for use with the FACSCanto HTS. Cells were washed with 200 µL of cold PBS and spun at 500×g for 5 minutes, and the plate was flicked and gently dapped on a paper towel to remove excess buffer. The cells were resuspended and permeabilized by adding 200 µL of cold BD Perm/Wash Buffer I and incubated on ice for 30 minutes. The cells were pelleted by centrifugation at 500×g for 5 minutes and the buffer removed. The cells were washed once with 200 µL BD perm/wash buffer and repelleted, and the buffer was removed.

The cell pellet was resuspended in 40 µL of BD perm/wash buffer. Twenty (20) µL each of anti-CD3-PE, anti-CD20-APC, and anti-Aiolos Rabbit antibodies, or 20 µL of appropriate isotype controls, or 20 µL of 1:400 of normal Rabbit IgG (control for Aiolos) were added to the cells. The mixture was mixed thoroughly and incubated at room temperature for 45 minutes in the dark. The mixture was centrifuged and washed once with BD perm/wash buffer at 500×g for 5 minutes. The cell pellet was resuspended in 80 µL of BD perm/wash buffer, and 20 µL of secondary Goat Anti-Rabbit IgG AF488 antibody (at 1:400 dilution in Perm/Wash Buffer) was added, and the mixture was incubated at RT for 30 min in the dark. Secondary antibody was not added to the isotype controls. The mixture was washed once with 200 µL BD Stain Buffer and centrifuged at 500×g for 5 minutes, and the pelleted cells were resuspended in 200 µL of staining buffer. The cells were analyzed on the BD FACSCanto using the HTS platform. The cells were analyzed using the standard method. If the cells cannot be read right away, the plates were covered in foil to protect from light and stored at 4° C. for up to 2 days. Data analysis was carried out using FlowJo from Tree Star, Inc. to assess mean fluorescence intensity and percent inhibition of Aiolos in cell population.

As shown in FIG. 33A, Compound A and Compound B both significantly inhibited the expression of Aiolos in lymphocytes at 1.5 hours after the treatment, but no significant effect was observed in non-lymphocytes. In lymphocytes, the inhibitory effect was observed in both T and B cell populations (FIG. 33B). Substantively similar pattern was observed at 5 hour after the treatment, albeit the degree of inhibition was more significant than that observed at 1.5 hours (FIGS. 34A and 34B).

7.7.2 Effects on Viably Frozen PBMCs

Pre-weighed test compound was dissolved in 100% DMSO to make 100 mM or 10 mM stock concentrations. The compound in 100% DMSO was diluted to 10 mM, 1 mM, or 0.1 stock concentrations as appropriate. Compounds were directly added to heparinized human whole blood (1:1000 dilution) for final concentrations of 10 µM, 1 µM, or 0.1 µL as appropriate. Seven (7) ml of whole blood was transferred to a 50 mL conical tube and treated with test compound. The blood was incubated for 1.5 or 5 hours at 37° C., 5% $CO_2$. After each time point, 3.5 ml blood was transferred to BD Vacutainer CPT cell preparation tube, and the tube was genetically inverted 10 times and centrifuged at RT, 1800 RCF for 20 minutes. Mononuclear layer was collected and transferred to 15 ml conical tube (3×3.5 ml DMSO controls were added to three CPT tubes, and mononuclear layers were collected and combined for following steps). The tube was filled up with cold PBS and centrifuged at 4° C., 300 RCF for 15 minutes. Supernatant was discarded and cell pellet was resuspended in 2 ml freezing medium (10% DMSO+90% FBS). The cell suspension was transferred to cryovial and was placed in Mr. Frosty (Fisher, cat. 15-350-50) and left at −80° C. freezer O/N.

The cells were thawed in 37° C. water bath and centrifuged, and the freezing medium was removed. The cell pellet was washed 1× with cold PBS. The cells were lyzed and fixed by adding 1× Lyse/Fix buffer and mixed thoroughly by inverting the tube several times. The cell lyse/fix and blood mixture was incubated in a 37° C. water bath for 10 minutes. Cells were pelleted by centrifugation at 500×g for 5 minutes and removed the supernatant by aspiration. Cells were suspended with 1 mL of cold PBS, and then pelleted by centrifugation at 500×g for 5 minutes, and the supernatant was aspirated off. Two hundred (200) µL of PBS was added to cells. Cells were transferred to polystyrene U-bottom 96-well plates (BD, Cat. No. 353910) for use with the FACSCanto HTS. Cells were washed with 200 µL of cold PBS and spun at 500×g for 5 minutes, and the plate was flicked and gently dapped on a paper towel to remove excess buffer. The cells were resuspended and permeabilized by adding 200 µL of cold BD Perm/Wash Buffer I and incubated on ice for 30 minutes. The cells were pelleted by centrifugation at 500×g for 5 minutes and the buffer removed. The cells were washed once with 200 µL BD perm/wash buffer and repelleted, and the buffer was removed.

The cell pellet was resuspended in 40 µL of BD perm/wash buffer. Twenty (20) µL each of anti-CD3-PE, anti-CD20-APC, and anti-Aiolos Rabbit antibodies, or 20 µL of appropriate isotype controls, or 20 μL of 1:400 of normal Rabbit IgG (control for Aiolos) were added to the cells. The mixture was mixed thoroughly and incubated at room temperature for 45 minutes in the dark. The mixture was centrifuged and washed once with BD perm/wash buffer at 500×g for 5 minutes. The cell pellet was resuspended in 80 μL of BD perm/wash buffer, and 20 μL of secondary Goat Anti-Rabbit IgG AF488 antibody (at 1:400 dilution in Perm/Wash Buffer) was added, and the mixture was incubated at RT for 30 min in the dark. Secondary antibody was not added to the isotype controls. The mixture was washed once with 200 μL BD Stain Buffer and centrifuged at 500×g for 5 minutes, and the pelleted cells were resuspended in 200 μL of staining buffer. The cells were analyzed on the BD FACSCanto using the HTS platform. The cells were analyzed using the standard method. If the cells cannot be read right away, the plates were covered in foil to protect from light and stored at 4° C. for up to 2 days. Data analysis was carried out using FlowJo from Tree Star, Inc. to assess mean fluorescence intensity and percent inhibition of Aiolos in cell population.

Figure 35B:
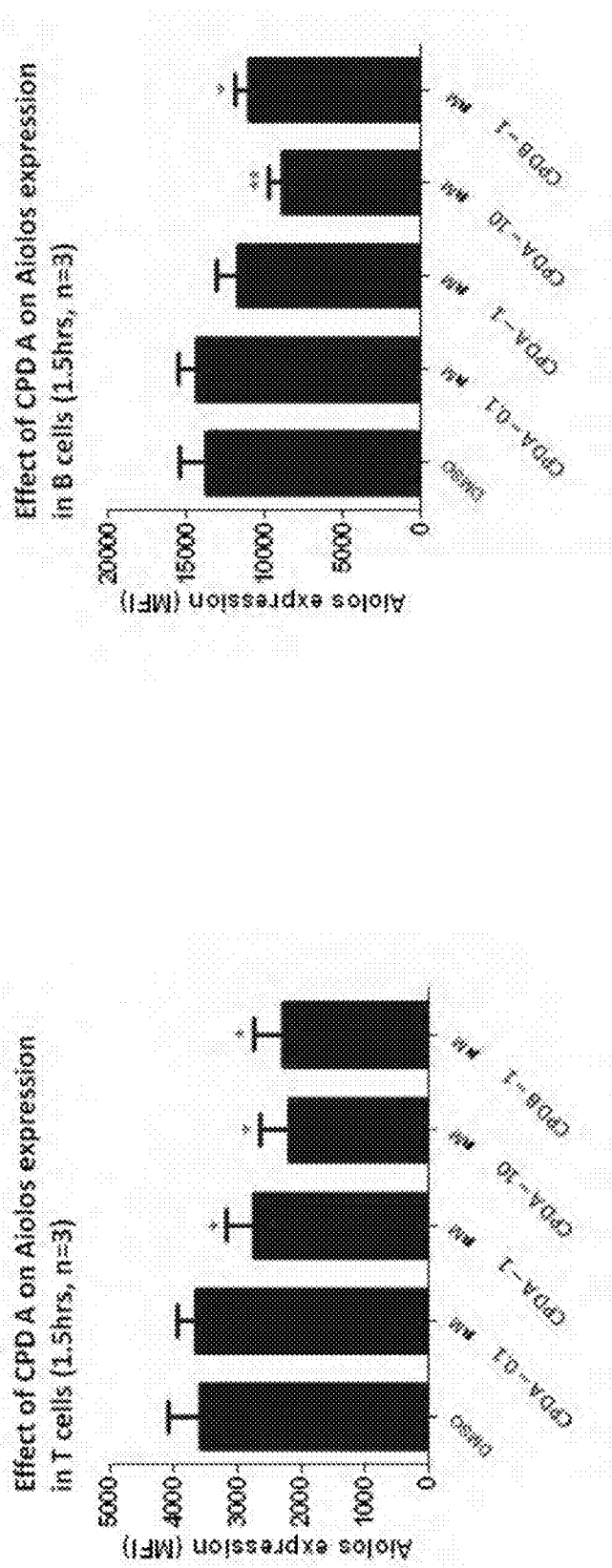

As shown in FIG. 35A, Compound A and Compound B show some inhibitory effects on the expression of Aiolos in lymphocytes frozen at 1.5 hours after the treatment, but no effect was observed in non-lymphocytes. In lymphocytes, the inhibitory effect was observed in both T and B cell populations (FIG. 35B). In lymphocyte cells frozen at 5 hours after the treatment, it was observed that both Compound A and Compound B exhibited significant inhibitory effects, while no such effects were observed in non-lymphocytes (FIGS. 36A and 36B). The results indicate that the cells can be frozen before the actual testing on the Aiolos levels can take place, and thus, imply that freezing the cells may be a viable method where storage of cells for a period of time is required before the testing.

7.8 Effects of Compounds on Aiolos and Ikaros Expression

Effects of test compounds (pomalidomide, lenalidomide, Compound A and Compound B) on expression of Aiolos and Ikaros expression were assessed by western blot analysis at 6 hours after the treatment by the compounds, using procedures similar to those use in connection with western blotting described in FIG. 7, above. As shown in FIG. 37, it was shown that all of the compounds, with varying degrees, inhibited the expression of both Aiolos and Ikaros.

7.8.1 Lenalidomide and Pomalidomide

The effect of lenalidomide and pomalidomide in the inhibition of Aiolos and Ikaros expression in U266, primary CD3+ T cells, and primary CD19+ B cells is shown in FIG. 39A. As shown in FIGS. 39 B and C, various concentrations of lenalidomide and pomalidomide significantly inhibited Aiolos and Ikaros expression in six MM cell lines (OPM-2, RPMI-8226, LP-1, U266, H929 and JJN3). Each bar represents the mean of 6 cell lines tested in duplicate and error bars represent one standard deviation.

The effect of 10 μM lenalidomide and 1 μM pomalidomide in the inhibition of Aiolos and Ikaros expression in U266, DF15 MM cells, primary CD3+ T cells, and primary CD19+ B cells is shown in FIG. 40. The effect of cycloheximide treated U266 cells treated with 10 μM lenalidomide and 1 μM pomalidomide is shown in FIG. 41. The results showed that lenalidomide and pomalidomide reduced the expression of Aiolos and Ikaros in all of the respective cells tested.

It was also found that the reduction of Aiolos and Ikaros levels by lenalidomide and pomalidomide is CRBN-dependent. Primary human CD3+ T cells were transfected with siControl or siCRBN for 24 hours then treated with lenalidomide or pomalidomide at indicated concentrations for 6/24 hours. Cell lysates were separated on SDS-PAGE gels and immunoblotted for Aiolos, Ikaros and Actin protein expression. As shown in FIGS. 42 A and B, in cells where CRBN is knocked-down, the effect of lenalidomide and pomalidomide in reducing or inhibiting the expression of Aiolos and Ikaros was significantly reduced as compared to the control cells with no CRBN knock-down.

Figure 44:
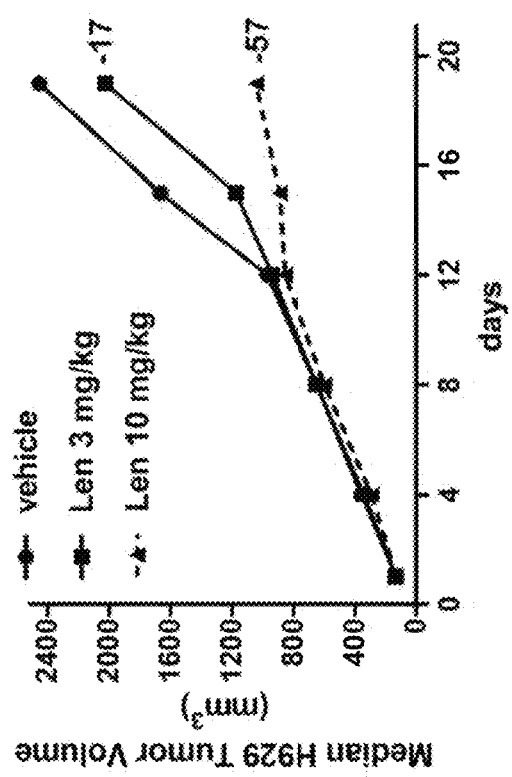

FIG. 44 A shows the in vivo antitumor activity of lenalidomide, while FIGS. 44 B and C show the reduction in expression Aiolos and Ikaros by the same doses of lenalidomide. As can be seen form these two figures, it was found that in vivo antitumor activity of lenalidomide correlates with reduction of Aiolos and Ikaros levels. In addition, as shown in FIG. 46, this correlation also extended to the antitumor activity of lenalidomide shown in DLBCL xenograft models. Further, other treatment compounds for multiple myeloma (MM) were tested along with lenalidomide and pomalidomide for their ability to reduce the levels of Aiolos and Ikaros. Interestingly, it was found that the reduction of Aiolos and Ikaros levels in MM cells is unique to immunomodulatory compounds provided herein, i.e., lenalidomide and pomalidomide (FIG. 45).

7.8.2 Compound A and Compound B

The effect of Compound A on Aiolos expression in B and T cells is shown in FIGS. 47 A and B. The effect of various compounds provided herein, including Compound A and Compound B, on Aiolos and Ikaros is shown in FIGS. 48 A and B. The results show that Compound A and Compound B reduced the expression of Aiolos and Ikaros in all of the respective cells tested.

The effects of Compound A on endogenous and overexpressed Aiolos in Jurkat cells were also assessed. As shown in FIG. 49, ubiquitination of multiple lysines are required for Compound A mediated Aiolos degradation. It was found that Aiolos degradation induced by the compound is due to Aiolos ubiquitination, and Compound A-induced Ikaros degradation is Aiolos-independent in Jurkat cells.

Western blot analysis (electropherograms of lysates) of normal human CD19+ B cells, treated with Compound B at specified concentrations, is shown in FIG. 52. As shown in the figure, Compound B inhibited the expression of Ikaros and Aiolos at various concentrations without affecting Helios, Pegasus, or β-Actin.

The relative mRNA levels corresponding to various proteins in cells obtained from a variety of disease sources are shown in FIG. 53 A-G. As shown in the figures, Ikaros and Aiolos are overexpressed in systemic sclerosis (SSc) and systemic lupus erythematosus (SLE).

Studies on 32 Cyno Monkeys using Compound B were conducted. Briefly, four treatment groups were assigned, each of which received treatment by Compound B according to the doses specified in FIG. 54. The results in FIGS. 54 and 55 A-C show that Compound B generally reduces the levels of Ikaros.

7.9 Effects Compounds on Protein Levels Measured by Western Blot

B-CLL cells were co-cultured with CD40L fibroblasts as described earlier followed 72 hours of treatment with DMSO, 10 μM lenalidomide, 1 μM pomalidomide, 0.1 μM Compound A, and 0.1 μM Compound B. Cells were harvested and analyzed by Western blot. Effects of compound treatment on CRBN, Aiolos, p21$^{WAF-1}$ and IRF4 were evaluated in 3 different patient cell samples (FIG. 56A). The three patient samples show similar expression levels of CRBN protein (compare lane 1 of the 3 Western blots in FIG. 56A; samples were run in same membrane even though gels are presented as 3 independent pictures in the figure). Treatments with compounds do not affect CRBN protein levels or in some samples induce slight increased of CRBN levels. Protein levels of transcription factors Aiolos and IRF4, proposed targets of IMiDs downstream of CRBN, were down regulated (FIG. 56A) and p21$^{WAF-1}$ protein level upregulated by treatment with lenalidomide, pomalidomide, Compound A and Compound B in the three patient samples evaluated. The effect of compounds on Aiolos decrease was dose dependent as demonstrated by flow cytometry (FIG. 56B) using an Aiolos specific antibody (Santa Cruz) in three different B-CLL patient co-cultures. The effects on p21, IRF4 and Aiolos are consistent with the cell cycle arrest and inhibition of proliferation observed with compound treatment.

7.10 CRBN Knockdown Abrogates Effect of IMiD Compounds on Aiolos and Ikaros in B-CLL Cells B-CLL cells transfected for 48 hours with negative control siRNA or CRBN specific siRNA were co-cultured with CD40L fibroblasts and treated with compounds. After 5 days of treatment Aiolos and Ikaros protein levels were measured by Western blot of Flow cytometry. CRBN knockdown reduced significantly the effect of IMiD compounds on Aiolos and Ikaros protein levels preventing its degradation in three different B-CLL patient samples (FIG. 57). As shown in FIG. 57, it was found that CRBN knockdown decrease the inhibitory effects of the compounds on Aiolos and Ikaros protein levels the most proximal targets of the compounds downstream of CRBN. These results are in agreement with similar data in myeloma and T cells. Aiolos is overexpressed in B-CLL patients and it is required for B-CLL viability suggesting that Aiolos and other members of the Ikaros family of transcription factors might be good therapeutic targets in B-CLL cells.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of assessing the efficacy of a compound in treating a disease or disorder, comprising:
   (a) administering a compound to a subject having a disease or disorder;
   (b) obtaining a first cell sample from the subject after administering the compound;
   (c) determining the level of IKZF1 and/or IKZF3 in the first cell sample by measuring the protein level of IKZF1 and/or IKZF3; and
   (d) comparing the level of IKZF1 and/or IKZF3 from step (c) to the level of the same protein obtained from a reference cell sample,
   wherein a decrease in the level of IKZF1 and/or IKZF3 as compared to the reference is indicative of the efficacy of the compound in treating the disease or disorder;
   wherein the disease or disorder is a blood cancer; and
   wherein the compound is thalidomide, lenalidomide, pomalidomide, 3-(5-amino-2-methyl-4-oxo-4H-quinazolin-3-yl)-piperidine-2,6-dione or 3-(4-((4-(morpholinomethyl)benzyl)oxy)-1-oxoisoindolin-2-yl)piperidine-2,6-dione, or a pharmaceutically acceptable salt-thereof.

2. The method of claim 1, wherein the first cell sample is obtained from a tumor biopsy, node biopsy, or a biopsy from bone marrow, spleen, liver, brain or breast.

3. The method of claim 1, wherein the reference is prepared by using a second cell sample obtained from the subject prior to administration of the compound to the subject; and wherein the second cell sample is from the same source as the first cell sample.

4. The method of claim 1, wherein the reference is prepared by using a second cell sample obtained from a healthy subject not having the disease or disorder; and wherein the second cell sample is from the same source as the first cell sample.

5. The method of claim 1, wherein the blood cancer is multiple myeloma, chronic lymphocytic leukemia, non-Hodgkin's Lymphoma, or mantle cell lymphoma.

6. The method of claim 5, wherein the blood cancer is multiple myeloma.

7. The method of claim 5, wherein the blood cancer is chronic lymphocytic leukemia.

8. The method of claim 5, wherein the blood cancer is non-Hodgkin's Lymphoma.

9. The method of claim 5, wherein the blood cancer is mantle cell lymphoma.

10. A method of assessing the efficacy of a compound in treating a disease or disorder, comprising:
    (a) administering a compound to a subject having a disease or disorder;
    (b) obtaining a first cell sample from the subject after administering the compound;
    (c) determining the level of IKZF1 and/or IKZF3 in the first cell sample by measuring the protein level of IKZF1 and/or IKZF3; and
    (d) comparing the level of IKZF1 and/or IKZF3 from step (c) to the level of the same protein obtained from a reference cell sample,
    wherein a decrease in the level of IKZF1 and/or IKZF3 as compared to the reference is indicative of the efficacy of the compound in treating the disease or disorder;
    wherein the disease or disorder is an inflammatory disease selected from the group consisting of: systemic lupus erythematosus, Sjogren syndrome and systemic sclerosis; and
    wherein the compound is thalidomide, lenalidomide, pomalidomide, 3-(5-amino-2-methyl-4-oxo-4H-quinazolin-3-yl)-piperidine-2,6-dione or 3-(4-((4-(morpholinomethyl)benzyl)oxy)-1-oxoisoindolin-2-yl)piperidine-2,6-dione, or a pharmaceutically acceptable salt-thereof.

11. The method of claim 10, wherein the reference is prepared by using a second cell sample obtained from the subject prior to administration of the compound to the subject; and wherein the second cell sample is from the same source as the first cell sample.

12. The method of claim 10, wherein the reference is prepared by using a second cell sample obtained from a healthy subject not having the disease or disorder; and wherein the second cell sample is from the same source as the first cell sample.

13. The method of claim 10, wherein the disease or disorder is systemic lupus erythematosus.

14. The method of claim 10, wherein the disease or disorder is Sjogren syndrome.

15. The method of claim 10, wherein the disease or disorder is systemic sclerosis.

* * * * *